United States Patent
Merritt et al.

(10) Patent No.: US 11,642,209 B2
(45) Date of Patent: May 9, 2023

(54) SYSTEM FOR TREATING EMBOLISM AND ASSOCIATED DEVICES AND METHODS

(71) Applicant: Inari Medical, Inc., Irvine, CA (US)

(72) Inventors: Ben Merritt, San Clemente, CA (US); Jacqueline Macias, Fullerton, CA (US); Brian Michael Strauss, San Clemente, CA (US); Thomas Tu, Louisville, KY (US)

(73) Assignee: Inari Medical, Inc., Irvine, CA (US)

( * ) Notice: Subject to any disclaimer, the term of this patent is extended or adjusted under 35 U.S.C. 154(b) by 0 days.

(21) Appl. No.: 17/865,315

(22) Filed: Jul. 14, 2022

(65) Prior Publication Data

US 2022/0346801 A1    Nov. 3, 2022

Related U.S. Application Data

(63) Continuation of application No. 16/536,185, filed on Aug. 8, 2019, now Pat. No. 11,559,382.
(Continued)

(51) Int. Cl.
*A61F 2/01* (2006.01)
*A61B 17/12* (2006.01)
(Continued)

(52) U.S. Cl.
CPC .......... *A61F 2/01* (2013.01); *A61B 17/12109* (2013.01); *A61M 1/815* (2021.05);
(Continued)

(58) Field of Classification Search
CPC ............ A61B 17/12109; A61B 17/221; A61B 2017/22034; A61B 2017/22079;
(Continued)

(56) References Cited

U.S. PATENT DOCUMENTS

| 2,846,179 A | 8/1958 | Monckton |
| 2,955,592 A | 10/1960 | Maclean |

(Continued)

FOREIGN PATENT DOCUMENTS

| AU | 2015210338 | 8/2015 |
| CN | 102186427 | 9/2011 |

(Continued)

OTHER PUBLICATIONS

European Patent Application No. 13838945.7, Extended European Search Report, 9 pages, dated Apr. 15, 2016.
(Continued)

*Primary Examiner* — Susan S Su
*Assistant Examiner* — Eric Rassavong
(74) *Attorney, Agent, or Firm* — Perkins Coie LLP

(57) ABSTRACT

Systems and methods for the intravascular treatment of clot material within a blood vessel of a human patient are disclosed herein. A method in accordance with embodiments of the present technology can include, for example, positioning a distal portion of a catheter proximate to the clot material within the blood vessel. The method can further include coupling a pressure source to the catheter via a tubing subsystem including a valve or other fluid control device and, while the valve is closed, activating the pressure source to charge a vacuum. The valve can then be opened to apply the vacuum to the catheter to thereby aspirate at least a portion of the clot material from the blood vessel and into the catheter.

18 Claims, 38 Drawing Sheets

Related U.S. Application Data

(60) Provisional application No. 62/718,248, filed on Aug. 13, 2018, provisional application No. 62/718,269, filed on Aug. 13, 2018.

(51) Int. Cl.
    *A61M 1/00*           (2006.01)
    *A61B 17/22*          (2006.01)
    *A61B 17/221*         (2006.01)
    *A61M 25/10*         (2013.01)

(52) U.S. Cl.
CPC .............. *A61M 1/84* (2021.05); *A61B 17/221* (2013.01); *A61B 2017/22034* (2013.01); *A61B 2017/22079* (2013.01); *A61B 2217/005* (2013.01); *A61M 1/79* (2021.05); *A61M 25/10* (2013.01)

(58) Field of Classification Search
CPC .......... A61B 17/005; A61F 2/01; A61M 1/84; A61M 25/10
See application file for complete search history.

(56) References Cited

U.S. PATENT DOCUMENTS

| | | |
|---|---|---|
| 3,088,363 A | 5/1963 | Sparks |
| 3,197,173 A | 7/1965 | Taubenheim |
| 3,435,826 A | 4/1969 | Fogarty |
| 3,515,137 A | 6/1970 | Santomieri |
| 3,675,657 A | 7/1972 | Gauthier |
| 3,892,161 A | 7/1975 | Sokol |
| 3,923,065 A | 12/1975 | Nozick et al. |
| 4,030,503 A | 6/1977 | Clark, III |
| 4,034,642 A | 7/1977 | Iannucci et al. |
| 4,222,380 A | 9/1980 | Terayama |
| 4,243,040 A | 1/1981 | Beecher |
| 4,287,808 A | 9/1981 | Leonard et al. |
| 4,324,262 A | 4/1982 | Hall |
| 4,393,872 A | 7/1983 | Reznik et al. |
| 4,469,100 A | 9/1984 | Hardwick |
| 4,523,738 A | 6/1985 | Raftis et al. |
| 4,551,862 A | 11/1985 | Haber |
| 4,604,094 A | 8/1986 | Shook |
| 4,611,594 A | 9/1986 | Grayhack et al. |
| 4,643,184 A | 2/1987 | Mobin-Uddin |
| 4,646,736 A | 3/1987 | Auth et al. |
| 4,650,466 A | 3/1987 | Luther |
| 4,776,337 A | 10/1988 | Palmaz |
| 4,790,812 A | 12/1988 | Hawkins, Jr. et al. |
| 4,863,440 A | 9/1989 | Chin et al. |
| 4,870,953 A | 10/1989 | DonMichael et al. |
| 4,883,458 A | 11/1989 | Shiber |
| 4,886,062 A | 12/1989 | Wiktor |
| 4,890,611 A | 1/1990 | Monfort et al. |
| 4,898,575 A | 2/1990 | Fischell et al. |
| 4,946,440 A | 8/1990 | Hall |
| 4,960,259 A | 10/1990 | Sunnanvader et al. |
| 4,978,341 A | 12/1990 | Niederhauser |
| 5,059,178 A | 10/1991 | Ya |
| 5,100,423 A | 3/1992 | Fearnot |
| 5,127,626 A | 7/1992 | Hilal et al. |
| 5,129,910 A | 7/1992 | Phan et al. |
| 5,135,484 A | 8/1992 | Wright |
| 5,154,724 A | 10/1992 | Andrews |
| 5,158,564 A | 10/1992 | Schnepp-Pesch et al. |
| 5,192,274 A | 3/1993 | Bierman |
| 5,192,286 A | 3/1993 | Phan et al. |
| 5,192,290 A | 3/1993 | Hilal |
| 5,197,485 A | 3/1993 | Grooters |
| 5,329,923 A | 7/1994 | Lundquist |
| 5,360,417 A | 11/1994 | Gravener et al. |
| 5,364,345 A | 11/1994 | Lowery et al. |
| 5,376,101 A | 12/1994 | Green et al. |
| 5,383,887 A | 1/1995 | Nadal |
| 5,389,100 A | 2/1995 | Bacich et al. |
| 5,419,774 A | 5/1995 | Willard et al. |
| 5,421,824 A | 6/1995 | Clement et al. |
| 5,443,443 A | 8/1995 | Shiber |
| 5,456,667 A | 10/1995 | Ham et al. |
| 5,476,450 A | 12/1995 | Ruggio |
| 5,490,859 A | 2/1996 | Mische et al. |
| 5,496,365 A | 3/1996 | Sgro |
| 5,527,326 A | 6/1996 | Hermann et al. |
| 5,549,626 A | 8/1996 | Miller et al. |
| 5,591,137 A | 1/1997 | Stevens |
| 5,653,684 A | 8/1997 | Laptewicz et al. |
| 5,662,703 A | 9/1997 | Yurek et al. |
| 5,746,758 A | 5/1998 | Nordgren et al. |
| 5,749,858 A | 5/1998 | Cramer |
| 5,769,816 A | 6/1998 | Barbut et al. |
| 5,782,817 A | 7/1998 | Franzel et al. |
| 5,800,457 A | 9/1998 | Gelbfish |
| 5,827,229 A | 10/1998 | Auth et al. |
| 5,846,251 A | 12/1998 | Hart |
| 5,860,938 A | 1/1999 | Lafontaine et al. |
| 5,873,866 A | 2/1999 | Kondo et al. |
| 5,873,882 A | 2/1999 | Straub et al. |
| 5,876,414 A | 3/1999 | Straub |
| 5,895,406 A | 4/1999 | Gray et al. |
| 5,908,435 A | 6/1999 | Samuels |
| 5,911,710 A | 6/1999 | Barry et al. |
| 5,911,733 A | 6/1999 | Parodi |
| 5,911,754 A | 6/1999 | Kanesaka et al. |
| 5,941,869 A | 8/1999 | Patterson et al. |
| 5,947,985 A | 9/1999 | Imram |
| 5,954,737 A | 9/1999 | Lee |
| 5,971,938 A | 10/1999 | Hart et al. |
| 5,972,019 A | 10/1999 | Engelson et al. |
| 5,974,938 A | 11/1999 | Lloyd |
| 5,989,233 A | 11/1999 | Yoon |
| 5,993,483 A | 11/1999 | Gianotti |
| 6,030,397 A | 2/2000 | Moneti et al. |
| 6,066,158 A | 5/2000 | Engelson et al. |
| 6,068,645 A | 5/2000 | Tu |
| 6,126,635 A | 10/2000 | Simpson et al. |
| 6,142,987 A | 11/2000 | Tsugita |
| 6,146,396 A | 11/2000 | Konya et al. |
| 6,146,403 A | 11/2000 | St. Germain |
| 6,152,946 A | 11/2000 | Broome et al. |
| 6,156,055 A | 12/2000 | Ravenscroft |
| 6,159,230 A | 12/2000 | Samuels |
| 6,165,196 A | 12/2000 | Stack et al. |
| 6,168,579 B1 | 1/2001 | Tsugita |
| 6,179,859 B1 | 1/2001 | Bates et al. |
| 6,221,006 B1 | 4/2001 | Dubrul et al. |
| 6,228,060 B1 | 5/2001 | Howell |
| 6,238,412 B1 | 5/2001 | Dubrul et al. |
| 6,245,078 B1 | 6/2001 | Ouchi |
| 6,245,089 B1 | 6/2001 | Daniel et al. |
| 6,254,571 B1 | 7/2001 | Hart |
| 6,258,115 B1 | 7/2001 | Dubrul |
| 6,264,663 B1 | 7/2001 | Cano |
| 6,306,163 B1 | 10/2001 | Fitz |
| 6,322,572 B1 | 11/2001 | Lee |
| 6,350,271 B1 | 2/2002 | Kurz et al. |
| 6,361,545 B1 | 3/2002 | Macoviak et al. |
| 6,364,895 B1 | 4/2002 | Greenhalgh |
| 6,368,339 B1 | 4/2002 | Amplatz |
| 6,383,205 B1 | 5/2002 | Samson et al. |
| 6,402,771 B1 | 6/2002 | Palmer et al. |
| 6,413,235 B1 | 7/2002 | Parodi |
| 6,423,032 B2 | 7/2002 | Parodi |
| 6,432,122 B1 | 8/2002 | Gilson et al. |
| 6,451,036 B1 | 9/2002 | Heitzmann et al. |
| 6,458,103 B1 | 10/2002 | Albert et al. |
| 6,475,236 B1 | 11/2002 | Roubin et al. |
| 6,485,502 B2 | 11/2002 | Don Michael |
| 6,508,782 B1 | 1/2003 | Evans et al. |
| 6,511,492 B1 | 1/2003 | Rosenbluth et al. |
| 6,514,273 B1 | 2/2003 | Voss et al. |
| 6,530,923 B1 | 3/2003 | Dubrul et al. |
| 6,530,935 B2 | 3/2003 | Wensel et al. |
| 6,544,276 B1 | 4/2003 | Azizi |

(56) References Cited

U.S. PATENT DOCUMENTS

| | | | |
|---|---|---|---|
| 6,544,278 B1 | 4/2003 | Vrba et al. |
| 6,544,279 B1 | 4/2003 | Hopkins et al. |
| 6,551,342 B1 | 4/2003 | Shen et al. |
| 6,564,828 B1 | 5/2003 | Ishida |
| 6,569,181 B1 | 5/2003 | Burns |
| 6,575,995 B1 | 6/2003 | Huter et al. |
| 6,589,263 B1 | 7/2003 | Hopkins et al. |
| 6,596,011 B2 | 7/2003 | Johnson et al. |
| 6,602,271 B2 | 8/2003 | Adams et al. |
| 6,605,074 B2 | 8/2003 | Zadno-azizi et al. |
| 6,605,102 B1 | 8/2003 | Mazzocchi et al. |
| 6,610,077 B1 | 8/2003 | Hancock et al. |
| 6,620,148 B1 | 9/2003 | Tsugita |
| 6,620,179 B2 | 9/2003 | Brook et al. |
| 6,620,182 B1 | 9/2003 | Khosravi et al. |
| 6,623,460 B1 | 9/2003 | Heck |
| 6,635,068 B1 | 10/2003 | Dubrul et al. |
| 6,645,222 B1 | 11/2003 | Parodi et al. |
| 6,660,013 B2 | 12/2003 | Rabiner et al. |
| 6,660,014 B2 | 12/2003 | Demarais et al. |
| 6,663,650 B2 | 12/2003 | Sepetka et al. |
| 6,692,504 B2 | 2/2004 | Kurz et al. |
| 6,699,260 B2 | 3/2004 | Dubrul et al. |
| 6,702,830 B1 | 3/2004 | Demarais et al. |
| 6,719,717 B1* | 4/2004 | Johnson .............. A61M 1/34 604/9 |
| 6,755,847 B2 | 6/2004 | Eskuri |
| 6,767,353 B1 | 7/2004 | Shiber |
| 6,790,204 B2 | 9/2004 | Zadno-azizi et al. |
| 6,800,080 B1 | 10/2004 | Bates |
| 6,818,006 B2 | 11/2004 | Douk et al. |
| 6,824,545 B2 | 11/2004 | Sepetka et al. |
| 6,824,550 B1 | 11/2004 | Noriega et al. |
| 6,824,553 B1 | 11/2004 | Gene et al. |
| 6,830,561 B2 | 12/2004 | Jansen et al. |
| 6,846,029 B1 | 1/2005 | Ragner et al. |
| 6,902,540 B2 | 6/2005 | Dorros et al. |
| 6,939,361 B1 | 9/2005 | Kleshinski |
| 6,942,682 B2 | 9/2005 | Vrba et al. |
| 6,945,977 B2 | 9/2005 | Demarais et al. |
| 6,960,189 B2* | 11/2005 | Bates ................ A61M 1/7413 604/35 |
| 6,960,222 B2 | 11/2005 | Vo et al. |
| 7,004,931 B2* | 2/2006 | Hogendijk .......... A61M 1/7413 604/129 |
| 7,004,954 B1 | 2/2006 | Voss et al. |
| 7,036,707 B2 | 5/2006 | Aota et al. |
| 7,041,084 B2 | 5/2006 | Fotjik |
| 7,052,500 B2 | 5/2006 | Bashiri et al. |
| 7,056,328 B2 | 6/2006 | Arnott |
| 7,063,707 B2 | 6/2006 | Bose et al. |
| 7,069,835 B2 | 7/2006 | Nishri et al. |
| 7,094,249 B1 | 8/2006 | Thomas et al. |
| 7,179,273 B1 | 2/2007 | Palmer et al. |
| 7,223,253 B2* | 5/2007 | Hogendijk .............. A61M 1/81 604/9 |
| 7,232,432 B2 | 6/2007 | Fulton, III et al. |
| 7,244,243 B2 | 7/2007 | Lary |
| 7,285,126 B2 | 10/2007 | Sepetka et al. |
| 7,300,458 B2 | 11/2007 | Henkes et al. |
| 7,306,618 B2 | 12/2007 | Demond et al. |
| 7,320,698 B2 | 1/2008 | Eskuri |
| 7,323,002 B2 | 1/2008 | Johnson et al. |
| 7,331,980 B2 | 2/2008 | Dubrul et al. |
| 7,534,234 B2 | 5/2009 | Fotjik |
| 7,578,830 B2 | 8/2009 | Kusleika et al. |
| 7,621,870 B2 | 11/2009 | Berrada et al. |
| 7,674,247 B2 | 3/2010 | Fotjik |
| 7,691,121 B2 | 4/2010 | Rosenbluth et al. |
| 7,695,458 B2 | 4/2010 | Belley et al. |
| 7,763,010 B2 | 7/2010 | Evans et al. |
| 7,766,934 B2 | 8/2010 | Pal et al. |
| 7,775,501 B2 | 8/2010 | Kees |
| 7,780,696 B2 | 8/2010 | Daniel et al. |
| 7,905,877 B1 | 3/2011 | Oscar et al. |
| 7,905,896 B2 | 3/2011 | Straub |
| 7,938,809 B2 | 5/2011 | Lampropoulos et al. |
| 7,938,820 B2 | 5/2011 | Webster et al. |
| 7,967,790 B2 | 6/2011 | Whiting et al. |
| 7,976,511 B2 | 7/2011 | Fotjik |
| 7,993,302 B2 | 8/2011 | Hebert et al. |
| 7,993,363 B2 | 8/2011 | Demond et al. |
| 8,043,313 B2 | 10/2011 | Krolik et al. |
| 8,052,640 B2 | 11/2011 | Fiorella et al. |
| 8,057,496 B2 | 11/2011 | Fischer, Jr. |
| 8,057,497 B1 | 11/2011 | Raju et al. |
| 8,066,757 B2 | 11/2011 | Ferrera et al. |
| 8,070,769 B2 | 12/2011 | Broome |
| 8,070,791 B2 | 12/2011 | Ferrera et al. |
| 8,075,510 B2 | 12/2011 | Aklog et al. |
| 8,088,140 B2 | 1/2012 | Ferrera et al. |
| 8,092,486 B2 | 1/2012 | Berrada et al. |
| 8,100,935 B2 | 1/2012 | Rosenbluth et al. |
| 8,109,962 B2 | 2/2012 | Pal |
| 8,118,829 B2 | 2/2012 | Carrison et al. |
| 8,197,493 B2 | 6/2012 | Ferrera et al. |
| 8,246,641 B2 | 8/2012 | Osborne et al. |
| 8,261,648 B1 | 9/2012 | Marchand et al. |
| 8,267,897 B2 | 9/2012 | Wells |
| 8,298,257 B2 | 10/2012 | Sepetka et al. |
| 8,317,748 B2 | 11/2012 | Fiorella et al. |
| 8,337,450 B2 | 12/2012 | Fotjik |
| RE43,902 E | 1/2013 | Hopkins et al. |
| 8,357,178 B2 | 1/2013 | Grandfield et al. |
| 8,361,104 B2 | 1/2013 | Jones et al. |
| 8,409,215 B2 | 4/2013 | Sepetka et al. |
| 8,486,105 B2 | 7/2013 | Demond et al. |
| 8,491,539 B2 | 7/2013 | Fotjik |
| 8,512,352 B2 | 8/2013 | Martin |
| 8,535,283 B2* | 9/2013 | Heaton ................ A61M 1/98 604/319 |
| 8,535,334 B2 | 9/2013 | Martin |
| 8,545,526 B2 | 10/2013 | Martin et al. |
| 8,568,432 B2 | 10/2013 | Straub |
| 8,574,262 B2 | 11/2013 | Ferrera et al. |
| 8,579,915 B2 | 11/2013 | French et al. |
| 8,585,713 B2 | 11/2013 | Ferrera et al. |
| 8,608,754 B2 | 12/2013 | Wensel et al. |
| 8,657,867 B2 | 2/2014 | Dorn et al. |
| 8,696,622 B2 | 4/2014 | Fiorella et al. |
| 8,715,314 B1 | 5/2014 | Janardhan et al. |
| 8,721,714 B2 | 5/2014 | Kelley |
| 8,753,322 B2* | 6/2014 | Hu ..................... A61M 1/912 604/319 |
| 8,771,289 B2 | 7/2014 | Mohiuddin et al. |
| 8,777,893 B2 | 7/2014 | Malewicz |
| 8,784,441 B2 | 7/2014 | Rosenbluth et al. |
| 8,784,442 B2 | 7/2014 | Jones et al. |
| 8,795,305 B2 | 8/2014 | Martin et al. |
| 8,795,345 B2 | 8/2014 | Grandfield et al. |
| 8,801,748 B2 | 8/2014 | Martin |
| 8,808,259 B2* | 8/2014 | Walton ................. A61M 1/915 604/319 |
| 8,814,927 B2 | 8/2014 | Shin et al. |
| 8,820,207 B2 | 9/2014 | Marchand et al. |
| 8,826,791 B2 | 9/2014 | Thompson et al. |
| 8,828,044 B2 | 9/2014 | Aggerholm et al. |
| 8,833,224 B2 | 9/2014 | Thompson et al. |
| 8,845,621 B2 | 9/2014 | Fotjik |
| 8,852,226 B2 | 10/2014 | Gilson et al. |
| 8,939,991 B2 | 1/2015 | Krolik et al. |
| 8,945,143 B2 | 2/2015 | Ferrera et al. |
| 8,945,172 B2 | 2/2015 | Ferrera et al. |
| 8,956,384 B2 | 2/2015 | Berrada et al. |
| 8,992,504 B2 | 3/2015 | Castella et al. |
| 9,005,172 B2 | 4/2015 | Chung |
| 9,028,401 B1 | 5/2015 | Bacich et al. |
| 9,078,682 B2 | 7/2015 | Lenker et al. |
| 9,101,382 B2 | 8/2015 | Krolik et al. |
| 9,125,683 B2 | 9/2015 | Farhangnia et al. |
| 9,126,016 B2 | 9/2015 | Fulton |
| 9,149,609 B2 | 10/2015 | Ansel et al. |
| 9,155,552 B2 | 10/2015 | Ulm, III |
| 9,161,766 B2 | 10/2015 | Slee et al. |

(56) References Cited

U.S. PATENT DOCUMENTS

| | | |
|---|---|---|
| 9,173,668 B2 | 11/2015 | Ulm, III |
| 9,186,487 B2 | 11/2015 | Dubrul et al. |
| 9,204,887 B2 | 12/2015 | Cully et al. |
| 9,216,277 B2 | 12/2015 | Myers |
| 9,358,037 B2 | 1/2016 | Farhangnia et al. |
| 9,259,237 B2 | 2/2016 | Quick et al. |
| 9,283,066 B2 | 3/2016 | Hopkins et al. |
| 9,351,747 B2 | 5/2016 | Kugler et al. |
| 9,439,664 B2 | 9/2016 | Sos |
| 9,439,751 B2 | 9/2016 | White et al. |
| 9,456,834 B2 | 10/2016 | Folk |
| 9,463,035 B1 | 10/2016 | Greenhalgh et al. |
| 9,463,036 B2 | 10/2016 | Brady et al. |
| 9,526,864 B2 | 12/2016 | Quick |
| 9,526,865 B2 | 12/2016 | Quick |
| 9,566,424 B2 | 2/2017 | Pessin |
| 9,579,116 B1 | 2/2017 | Nguyen et al. |
| 9,616,213 B2 | 4/2017 | Furnish et al. |
| 9,636,206 B2 | 5/2017 | Nguyen et al. |
| 9,643,035 B2 | 5/2017 | Mastenbroek |
| 9,700,332 B2 | 7/2017 | Marchand et al. |
| 9,717,514 B2 | 8/2017 | Martin et al. |
| 9,717,519 B2 | 8/2017 | Rosenbluth et al. |
| 9,744,024 B2 | 8/2017 | Nguyen et al. |
| 9,757,137 B2 | 9/2017 | Krolik et al. |
| 9,827,084 B2 | 11/2017 | Bonnette et al. |
| 9,844,386 B2 | 12/2017 | Nguyen et al. |
| 9,844,387 B2 | 12/2017 | Marchand et al. |
| 9,848,975 B2 | 12/2017 | Hauser |
| 9,849,014 B2 | 12/2017 | Kusleika |
| 9,962,178 B2 | 5/2018 | Greenhalgh et al. |
| 9,980,813 B2 | 5/2018 | Eller |
| 9,999,493 B2 | 6/2018 | Nguyen et al. |
| 10,004,531 B2 | 6/2018 | Rosenbluth et al. |
| 10,010,335 B2 | 7/2018 | Greenhalgh et al. |
| 10,016,266 B2 | 7/2018 | Hauser |
| 10,028,759 B2 | 7/2018 | Wallace et al. |
| 10,045,790 B2 | 8/2018 | Cox et al. |
| 10,098,651 B2 | 10/2018 | Marchand et al. |
| 10,130,385 B2 | 11/2018 | Farhangnia et al. |
| 10,226,263 B2 | 3/2019 | Look et al. |
| 10,238,406 B2 | 3/2019 | Cox et al. |
| 10,271,864 B2 | 4/2019 | Greenhalgh et al. |
| 10,327,883 B2 | 6/2019 | Yachia |
| 10,335,186 B2 | 7/2019 | Rosenbluth et al. |
| 10,342,571 B2 | 7/2019 | Marchand et al. |
| 10,349,960 B2 | 7/2019 | Quick |
| 10,383,644 B2 | 8/2019 | Molaei et al. |
| 10,478,535 B2 * | 11/2019 | Ogle ................ A61M 25/0074 |
| 10,524,811 B2 | 1/2020 | Marchand et al. |
| 10,588,655 B2 | 3/2020 | Rosenbluth et al. |
| 10,695,159 B2 | 6/2020 | Hauser |
| 10,709,471 B2 | 7/2020 | Rosenbluth et al. |
| 10,799,331 B2 | 10/2020 | Hauser |
| 10,912,577 B2 | 2/2021 | Marchand et al. |
| 11,000,682 B2 | 5/2021 | Merritt et al. |
| 11,013,523 B2 | 5/2021 | Arad Hadar |
| 11,058,445 B2 | 7/2021 | Cox et al. |
| 11,058,451 B2 | 7/2021 | Marchand et al. |
| 11,147,571 B2 | 10/2021 | Cox et al. |
| 11,154,314 B2 | 10/2021 | Quick |
| 11,259,821 B2 | 3/2022 | Buck et al. |
| 11,406,801 B2 | 8/2022 | Fojtik et al. |
| 11,433,218 B2 | 9/2022 | Quick et al. |
| 11,439,799 B2 | 9/2022 | Buck et al. |
| 11,457,936 B2 | 10/2022 | Buck et al. |
| 11,529,158 B2 | 12/2022 | Hauser |
| 11,554,005 B2 | 1/2023 | Merritt et al. |
| 11,559,382 B2 | 1/2023 | Merritt et al. |
| 2001/0004699 A1 | 6/2001 | Gittings et al. |
| 2001/0041909 A1 | 11/2001 | Tsugita et al. |
| 2001/0049486 A1 * | 12/2001 | Evans ................ A61M 1/3621 604/35 |
| 2001/0051810 A1 | 12/2001 | Dubrul et al. |
| 2002/0022858 A1 | 2/2002 | Demond et al. |
| 2002/0022859 A1 | 2/2002 | Hogendijk |
| 2002/0026211 A1 | 2/2002 | Khosravi et al. |
| 2002/0032455 A1 | 3/2002 | Boock et al. |
| 2002/0049452 A1 | 4/2002 | Kurz et al. |
| 2002/0095161 A1 | 7/2002 | Dhindsa |
| 2002/0095171 A1 | 7/2002 | Belef |
| 2002/0111648 A1 | 8/2002 | Kusleika et al. |
| 2002/0120277 A1 | 8/2002 | Hauschild et al. |
| 2002/0147458 A1 | 10/2002 | Hiblar et al. |
| 2002/0151918 A1 | 10/2002 | Lafontaine et al. |
| 2002/0156457 A1 | 10/2002 | Fisher |
| 2002/0161392 A1 | 10/2002 | Dubrul |
| 2002/0169474 A1 | 11/2002 | Kusleika |
| 2002/0173819 A1 | 11/2002 | Leeflang et al. |
| 2002/0188276 A1 | 12/2002 | Evans et al. |
| 2003/0083693 A1 | 5/2003 | Daniel et al. |
| 2003/0100919 A1 | 5/2003 | Hopkins et al. |
| 2003/0114875 A1 | 6/2003 | Sjostrom |
| 2003/0116731 A1 | 6/2003 | Hartley |
| 2003/0125663 A1 | 7/2003 | Coleman et al. |
| 2003/0135230 A1 | 7/2003 | Massey et al. |
| 2003/0135258 A1 | 7/2003 | Andreas et al. |
| 2003/0153873 A1 | 8/2003 | Luther et al. |
| 2003/0153973 A1 | 8/2003 | Soun et al. |
| 2003/0168068 A1 | 9/2003 | Poole et al. |
| 2003/0176884 A1 | 9/2003 | Berrada et al. |
| 2003/0191516 A1 | 10/2003 | Weldon et al. |
| 2003/0208224 A1 | 11/2003 | Broome |
| 2003/0216774 A1 | 11/2003 | Larson |
| 2004/0039412 A1 | 2/2004 | Isshiki et al. |
| 2004/0068288 A1 | 4/2004 | Palmer et al. |
| 2004/0073243 A1 | 4/2004 | Sepetka et al. |
| 2004/0098033 A1 | 5/2004 | Leeflang et al. |
| 2004/0122359 A1 | 6/2004 | Wenz et al. |
| 2004/0127936 A1 | 7/2004 | Salahieh et al. |
| 2004/0133232 A1 | 7/2004 | Rosenbluth et al. |
| 2004/0138525 A1 | 7/2004 | Saadat et al. |
| 2004/0138692 A1 | 7/2004 | Phung et al. |
| 2004/0167567 A1 | 8/2004 | Cano et al. |
| 2004/0199201 A1 | 10/2004 | Kellett et al. |
| 2004/0199202 A1 | 10/2004 | Dubrul et al. |
| 2004/0260344 A1 | 12/2004 | Lyons et al. |
| 2004/0267272 A1 | 12/2004 | Henniges et al. |
| 2005/0033172 A1 | 2/2005 | Dubrul et al. |
| 2005/0038468 A1 | 2/2005 | Panetta et al. |
| 2005/0054995 A1 | 3/2005 | Barzell et al. |
| 2005/0055047 A1 | 3/2005 | Greenhalgh |
| 2005/0085769 A1 | 4/2005 | MacMahon et al. |
| 2005/0085826 A1 | 4/2005 | Nair et al. |
| 2005/0085846 A1 | 4/2005 | Carrison et al. |
| 2005/0085849 A1 | 4/2005 | Sepetka et al. |
| 2005/0119668 A1 | 6/2005 | Teague et al. |
| 2005/0177132 A1 | 8/2005 | Lentz et al. |
| 2005/0187570 A1 | 8/2005 | Nguyen et al. |
| 2005/0283165 A1 | 12/2005 | Gadberry |
| 2005/0283166 A1 | 12/2005 | Greenhalgh et al. |
| 2005/0283186 A1 | 12/2005 | Berrada et al. |
| 2006/0020286 A1 | 1/2006 | Niermann |
| 2006/0042786 A1 | 3/2006 | West |
| 2006/0047286 A1 | 3/2006 | West |
| 2006/0074401 A1 | 4/2006 | Ross |
| 2006/0089533 A1 | 4/2006 | Ziegler et al. |
| 2006/0100662 A1 | 5/2006 | Daniel et al. |
| 2006/0155305 A1 | 7/2006 | Freudenthal et al. |
| 2006/0173525 A1 | 8/2006 | Behl et al. |
| 2006/0195137 A1 | 8/2006 | Sepetka et al. |
| 2006/0200221 A1 | 9/2006 | Malewicz |
| 2006/0217664 A1 | 9/2006 | Hattler et al. |
| 2006/0224177 A1 | 10/2006 | Finitsis |
| 2006/0229645 A1 | 10/2006 | Bonnette et al. |
| 2006/0247500 A1 | 11/2006 | Voegele et al. |
| 2006/0253145 A1 | 11/2006 | Lucas |
| 2006/0276874 A1 | 12/2006 | Wilson et al. |
| 2006/0282111 A1 | 12/2006 | Morsi |
| 2006/0293696 A1 | 12/2006 | Fahey et al. |
| 2007/0010787 A1 * | 1/2007 | Hackett ............ A61B 17/22032 604/96.01 |
| 2007/0038225 A1 | 2/2007 | Osborne |
| 2007/0093744 A1 | 4/2007 | Elmaleh |

(56) References Cited

U.S. PATENT DOCUMENTS

| | | |
|---|---|---|
| 2007/0112374 A1 | 5/2007 | Paul, Jr. et al. |
| 2007/0118165 A1 | 5/2007 | DeMello et al. |
| 2007/0149996 A1 | 6/2007 | Coughlin |
| 2007/0161963 A1 | 7/2007 | Smalling |
| 2007/0179513 A1 | 8/2007 | Deutsch |
| 2007/0191866 A1 | 8/2007 | Palmer et al. |
| 2007/0198028 A1 | 8/2007 | Miloslavski et al. |
| 2007/0208361 A1 | 9/2007 | Okushi et al. |
| 2007/0208367 A1 | 9/2007 | Fiorella et al. |
| 2007/0213753 A1 | 9/2007 | Waller |
| 2007/0213765 A1 | 9/2007 | Adams et al. |
| 2007/0255252 A1 | 11/2007 | Mehta |
| 2007/0288054 A1 | 12/2007 | Tanaka et al. |
| 2008/0015541 A1 | 1/2008 | Rosenbluth et al. |
| 2008/0088055 A1 | 4/2008 | Ross |
| 2008/0157017 A1 | 7/2008 | Macatangay et al. |
| 2008/0167678 A1 | 7/2008 | Morsi |
| 2008/0183136 A1 | 7/2008 | Lenker et al. |
| 2008/0228209 A1 | 9/2008 | DeMello et al. |
| 2008/0234715 A1 | 9/2008 | Pesce et al. |
| 2008/0234722 A1 | 9/2008 | Bonnette et al. |
| 2008/0262528 A1 | 10/2008 | Martin |
| 2008/0269798 A1 | 10/2008 | Ramzipoor et al. |
| 2008/0300466 A1 | 12/2008 | Gresham |
| 2009/0018566 A1 | 1/2009 | Escudero et al. |
| 2009/0054918 A1 | 2/2009 | Henson |
| 2009/0062841 A1 | 3/2009 | Amplatz et al. |
| 2009/0069828 A1 | 3/2009 | Martin et al. |
| 2009/0076417 A1 | 3/2009 | Jones |
| 2009/0160112 A1 | 6/2009 | Ostrovsky |
| 2009/0163846 A1 | 6/2009 | Aklog et al. |
| 2009/0182362 A1 | 7/2009 | Thompson et al. |
| 2009/0192495 A1 | 7/2009 | Ostrovsky et al. |
| 2009/0281525 A1 | 11/2009 | Harding et al. |
| 2009/0292307 A1 | 11/2009 | Razack |
| 2009/0299393 A1 | 12/2009 | Martin et al. |
| 2010/0016837 A1 | 1/2010 | Howat |
| 2010/0030256 A1 | 2/2010 | Dubrul et al. |
| 2010/0042136 A1 | 2/2010 | Berrada et al. |
| 2010/0087844 A1 | 4/2010 | Fischer, Jr. |
| 2010/0087850 A1 | 4/2010 | Razack |
| 2010/0114113 A1 | 5/2010 | Dubrul et al. |
| 2010/0121312 A1 | 5/2010 | Gielenz et al. |
| 2010/0137846 A1 | 6/2010 | Desai et al. |
| 2010/0190156 A1 | 7/2010 | Van Wordragen et al. |
| 2010/0204712 A1 | 8/2010 | Mallaby |
| 2010/0217276 A1* | 8/2010 | Garrison ............ A61M 1/3613 604/9 |
| 2010/0249815 A1 | 9/2010 | Jantzen et al. |
| 2010/0268264 A1 | 10/2010 | Bonnette et al. |
| 2010/0318178 A1 | 12/2010 | Rapaport et al. |
| 2011/0034986 A1 | 2/2011 | Chou et al. |
| 2011/0034987 A1 | 2/2011 | Kennedy |
| 2011/0054405 A1 | 3/2011 | Whiting et al. |
| 2011/0060212 A1 | 3/2011 | Slee et al. |
| 2011/0118817 A1 | 5/2011 | Gunderson et al. |
| 2011/0125181 A1 | 5/2011 | Brady et al. |
| 2011/0144592 A1 | 6/2011 | Wong et al. |
| 2011/0152823 A1 | 6/2011 | Mohiuddin et al. |
| 2011/0152993 A1 | 6/2011 | Marchand et al. |
| 2011/0160742 A1 | 6/2011 | Ferrera et al. |
| 2011/0160763 A1 | 6/2011 | Ferrera et al. |
| 2011/0190806 A1 | 8/2011 | Wittens |
| 2011/0196309 A1* | 8/2011 | Wells ................ A61M 5/14216 604/173 |
| 2011/0196414 A1 | 8/2011 | Porter et al. |
| 2011/0213290 A1 | 9/2011 | Chin et al. |
| 2011/0213403 A1 | 9/2011 | Aboytes |
| 2011/0224707 A1 | 9/2011 | Miloslavski et al. |
| 2011/0245807 A1 | 10/2011 | Sakata et al. |
| 2011/0251629 A1 | 10/2011 | Galdonik et al. |
| 2011/0264133 A1 | 10/2011 | Hanlon et al. |
| 2011/0265681 A1 | 11/2011 | Allen et al. |
| 2011/0288529 A1 | 11/2011 | Fulton |
| 2011/0288572 A1 | 11/2011 | Martin |
| 2011/0319917 A1 | 12/2011 | Ferrera et al. |
| 2012/0059309 A1 | 3/2012 | di Palma et al. |
| 2012/0059356 A1 | 3/2012 | di Palma et al. |
| 2012/0083824 A1 | 4/2012 | Berrada et al. |
| 2012/0083868 A1 | 4/2012 | Shrivastava |
| 2012/0089216 A1 | 4/2012 | Rapaport et al. |
| 2012/0101480 A1 | 4/2012 | Ingle et al. |
| 2012/0101510 A1 | 4/2012 | Lenker et al. |
| 2012/0138832 A1 | 6/2012 | Townsend |
| 2012/0143239 A1 | 6/2012 | Aklog et al. |
| 2012/0165919 A1 | 6/2012 | Cox et al. |
| 2012/0172918 A1 | 7/2012 | Fifer et al. |
| 2012/0179181 A1 | 7/2012 | Straub et al. |
| 2012/0197277 A1 | 8/2012 | Stinis |
| 2012/0232655 A1 | 9/2012 | Lorrison et al. |
| 2012/0271105 A1 | 10/2012 | Nakamura et al. |
| 2012/0271231 A1 | 10/2012 | Agrawal |
| 2012/0277788 A1 | 11/2012 | Cattaneo |
| 2012/0310166 A1 | 12/2012 | Huff |
| 2013/0030460 A1 | 1/2013 | Marks et al. |
| 2013/0035628 A1 | 2/2013 | Garrison et al. |
| 2013/0046332 A1 | 2/2013 | Jones et al. |
| 2013/0066348 A1 | 3/2013 | Fiorella et al. |
| 2013/0092012 A1 | 4/2013 | Marchand et al. |
| 2013/0096571 A1 | 4/2013 | Massicotte et al. |
| 2013/0102996 A1 | 4/2013 | Strauss |
| 2013/0116708 A1 | 5/2013 | Ziniti et al. |
| 2013/0116721 A1 | 5/2013 | Takagi et al. |
| 2013/0126559 A1 | 5/2013 | Cowan et al. |
| 2013/0144326 A1 | 6/2013 | Brady et al. |
| 2013/0165871 A1 | 6/2013 | Fiorella et al. |
| 2013/0184703 A1 | 7/2013 | Shireman et al. |
| 2013/0197454 A1 | 8/2013 | Shibata et al. |
| 2013/0197567 A1 | 8/2013 | Brady et al. |
| 2013/0226196 A1 | 8/2013 | Smith |
| 2013/0281788 A1* | 10/2013 | Garrison ............... A61B 17/221 606/127 |
| 2013/0289608 A1 | 10/2013 | Tanaka et al. |
| 2013/0317589 A1 | 11/2013 | Martin et al. |
| 2013/0345739 A1 | 12/2013 | Brady et al. |
| 2014/0005712 A1 | 1/2014 | Martin |
| 2014/0005713 A1 | 1/2014 | Bowman |
| 2014/0005715 A1 | 1/2014 | Castella et al. |
| 2014/0005717 A1 | 1/2014 | Martin et al. |
| 2014/0025048 A1 | 1/2014 | Ward |
| 2014/0031856 A1 | 1/2014 | Martin |
| 2014/0046133 A1 | 2/2014 | Nakamura et al. |
| 2014/0046243 A1 | 2/2014 | Ray et al. |
| 2014/0052161 A1 | 2/2014 | Cully et al. |
| 2014/0121672 A1 | 5/2014 | Folk |
| 2014/0155830 A1* | 6/2014 | Bonnette ........... A61M 25/0026 604/150 |
| 2014/0155980 A1 | 6/2014 | Turjman |
| 2014/0180397 A1 | 6/2014 | Gerberding et al. |
| 2014/0155908 A1 | 7/2014 | Rosenbluth et al. |
| 2014/0188143 A1 | 7/2014 | Martin et al. |
| 2014/0236219 A1 | 8/2014 | Dubrul et al. |
| 2014/0243882 A1 | 8/2014 | Ma |
| 2014/0257253 A1 | 9/2014 | Jemison |
| 2014/0257363 A1* | 9/2014 | Lippert ............ A61B 17/12031 606/200 |
| 2014/0276403 A1 | 9/2014 | Follmer et al. |
| 2014/0296868 A1* | 10/2014 | Garrison ................ A61B 17/22 606/127 |
| 2014/0303658 A1 | 10/2014 | Bonnette et al. |
| 2014/0318354 A1 | 10/2014 | Thompson et al. |
| 2014/0324091 A1 | 10/2014 | Rosenbluth |
| 2014/0330286 A1 | 11/2014 | Wallace et al. |
| 2014/0336691 A1 | 11/2014 | Jones et al. |
| 2014/0343593 A1 | 11/2014 | Chin et al. |
| 2014/0364896 A1 | 12/2014 | Consigny |
| 2014/0371779 A1 | 12/2014 | Vale et al. |
| 2015/0005781 A1 | 1/2015 | Lund-Clausen et al. |
| 2015/0005792 A1 | 1/2015 | Ahn |
| 2015/0018859 A1 | 1/2015 | Quick |
| 2015/0018860 A1 | 1/2015 | Quick |
| 2015/0018929 A1 | 1/2015 | Martin et al. |
| 2015/0025555 A1 | 1/2015 | Sos |
| 2015/0032144 A1 | 1/2015 | Holloway |

(56) References Cited

U.S. PATENT DOCUMENTS

| | | |
|---|---|---|
| 2015/0059908 A1 | 3/2015 | Mollen |
| 2015/0088190 A1 | 3/2015 | Jensen |
| 2015/0127035 A1 | 5/2015 | Trapp et al. |
| 2015/0133990 A1* | 5/2015 | Davidson ............ A61B 17/221 606/200 |
| 2015/0150672 A1 | 6/2015 | Ma |
| 2015/0164523 A1 | 6/2015 | Brady et al. |
| 2015/0164666 A1 | 6/2015 | Johnson et al. |
| 2015/0173782 A1* | 6/2015 | Garrison ........... A61M 25/0662 606/127 |
| 2015/0190155 A1 | 7/2015 | Ulm, III |
| 2015/0190156 A1 | 7/2015 | Ulm, III |
| 2015/0196380 A1 | 7/2015 | Berrada et al. |
| 2015/0196744 A1 | 7/2015 | Aboytes |
| 2015/0209058 A1 | 7/2015 | Ferrera et al. |
| 2015/0209165 A1 | 7/2015 | Grandfield et al. |
| 2015/0238207 A1 | 8/2015 | Cox et al. |
| 2015/0250578 A1 | 9/2015 | Cook et al. |
| 2015/0265299 A1 | 9/2015 | Cooper et al. |
| 2015/0305756 A1 | 10/2015 | Rosenbluth |
| 2015/0305859 A1 | 10/2015 | Eller |
| 2015/0352325 A1 | 12/2015 | Quick |
| 2015/0360001 A1 | 12/2015 | Quick |
| 2015/0374391 A1 | 12/2015 | Quick |
| 2016/0022293 A1 | 1/2016 | Dubrul et al. |
| 2016/0058540 A1 | 3/2016 | Don Michael |
| 2016/0074627 A1 | 3/2016 | Cottone |
| 2016/0106448 A1 | 4/2016 | Brady et al. |
| 2016/0106449 A1 | 4/2016 | Brady et al. |
| 2016/0113663 A1 | 4/2016 | Brady et al. |
| 2016/0113664 A1 | 4/2016 | Brady et al. |
| 2016/0113665 A1 | 4/2016 | Brady et al. |
| 2016/0113666 A1 | 4/2016 | Quick |
| 2016/0143721 A1 | 5/2016 | Rosenbluth |
| 2016/0151605 A1 | 6/2016 | Welch et al. |
| 2016/0206344 A1 | 7/2016 | Bruzzi et al. |
| 2016/0008014 A1 | 8/2016 | Rosenbluth |
| 2016/0220741 A1* | 8/2016 | Garrison ................ A61B 17/22 |
| 2016/0228134 A1 | 8/2016 | Martin et al. |
| 2016/0262774 A1 | 9/2016 | Honda |
| 2016/0262790 A1 | 9/2016 | Rosenbluth et al. |
| 2016/0287276 A1 | 10/2016 | Cox et al. |
| 2016/0367285 A1 | 12/2016 | Sos |
| 2017/0014560 A1 | 1/2017 | Minskoff et al. |
| 2017/0037548 A1 | 2/2017 | Lee |
| 2017/0042571 A1 | 2/2017 | Levi |
| 2017/0049942 A1 | 2/2017 | Conlan et al. |
| 2017/0056032 A1* | 3/2017 | Look ........................ A61M 1/74 |
| 2017/0058623 A1 | 3/2017 | Jaffrey et al. |
| 2017/0079672 A1 | 3/2017 | Quick |
| 2017/0086864 A1 | 3/2017 | Greenhalgh et al. |
| 2017/0100142 A1 | 4/2017 | Look et al. |
| 2017/0105743 A1 | 4/2017 | Vale et al. |
| 2017/0105745 A1 | 4/2017 | Rosenbluth et al. |
| 2017/0112514 A1 | 4/2017 | Marchand et al. |
| 2017/0112513 A1 | 7/2017 | Marchand et al. |
| 2017/0189041 A1 | 7/2017 | Cox et al. |
| 2017/0196576 A1* | 7/2017 | Long .................... A61M 3/0208 |
| 2017/0233908 A1 | 8/2017 | Kroczynski et al. |
| 2017/0252057 A1 | 9/2017 | Bonnette et al. |
| 2017/0265878 A1 | 9/2017 | Marchand et al. |
| 2017/0303939 A1 | 10/2017 | Greenhalgh et al. |
| 2017/0303942 A1 | 10/2017 | Greenhalgh et al. |
| 2017/0303947 A1 | 10/2017 | Greenhalgh et al. |
| 2017/0303948 A1 | 10/2017 | Wallace et al. |
| 2017/0319221 A1* | 11/2017 | Chu ........................ A61B 17/22 |
| 2017/0325839 A1 | 11/2017 | Rosenbluth et al. |
| 2017/0340867 A1 | 11/2017 | Accisano, II |
| 2017/0348014 A1 | 12/2017 | Wallace et al. |
| 2018/0042623 A1 | 2/2018 | Batiste |
| 2018/0042624 A1 | 2/2018 | Greenhalgh et al. |
| 2018/0042626 A1 | 2/2018 | Greenhalgh et al. |
| 2018/0064453 A1 | 3/2018 | Garrison et al. |
| 2018/0064454 A1 | 3/2018 | Losordo et al. |
| 2018/0070968 A1 | 3/2018 | Wallace et al. |
| 2018/0092652 A1 | 4/2018 | Marchand et al. |
| 2018/0104404 A1* | 4/2018 | Ngo-Chu ............... A61M 29/02 |
| 2018/0105963 A1 | 4/2018 | Quick |
| 2018/0125512 A1 | 5/2018 | Nguyen et al. |
| 2018/0184912 A1 | 7/2018 | Al-Ali |
| 2018/0193043 A1 | 7/2018 | Marchand et al. |
| 2018/0236205 A1 | 8/2018 | Krautkremer et al. |
| 2018/0256177 A1 | 9/2018 | Cooper et al. |
| 2018/0256178 A1 | 9/2018 | Cox et al. |
| 2018/0296240 A1 | 10/2018 | Rosenbluth et al. |
| 2018/0344339 A1 | 12/2018 | Cox et al. |
| 2018/0361116 A1 | 12/2018 | Quick et al. |
| 2019/0000492 A1 | 1/2019 | Casey et al. |
| 2019/0046219 A1 | 2/2019 | Marchand et al. |
| 2019/0070401 A1 | 3/2019 | Merritt et al. |
| 2019/0117244 A1 | 4/2019 | Wallace et al. |
| 2019/0133622 A1 | 5/2019 | Wallace et al. |
| 2019/0133623 A1 | 5/2019 | Wallace et al. |
| 2019/0133624 A1 | 5/2019 | Wallace et al. |
| 2019/0133625 A1 | 5/2019 | Wallace et al. |
| 2019/0133626 A1 | 5/2019 | Wallace et al. |
| 2019/0133627 A1 | 5/2019 | Wallace et al. |
| 2019/0150959 A1 | 5/2019 | Cox et al. |
| 2019/0231373 A1 | 8/2019 | Quick |
| 2019/0239910 A1 | 8/2019 | Brady et al. |
| 2019/0321071 A1 | 10/2019 | Marchand et al. |
| 2019/0336142 A1 | 11/2019 | Torrie et al. |
| 2019/0336148 A1 | 11/2019 | Greenhalgh et al. |
| 2020/0046368 A1 | 2/2020 | Merritt et al. |
| 2020/0113412 A1 | 4/2020 | Jensen |
| 2021/0022843 A1 | 1/2021 | Hauser |
| 2021/0113224 A1 | 4/2021 | Dinh |
| 2021/0137667 A1 | 5/2021 | Sonnette et al. |
| 2021/0186541 A1 | 6/2021 | Thress |
| 2021/0290925 A1 | 9/2021 | Merritt et al. |
| 2021/0315598 A1 | 10/2021 | Buck et al. |
| 2021/0330344 A1 | 10/2021 | Rosenbluth et al. |
| 2021/0378694 A1 | 12/2021 | Thress et al. |
| 2022/0000505 A1 | 1/2022 | Hauser |
| 2022/0000506 A1 | 1/2022 | Hauser |
| 2022/0000507 A1 | 1/2022 | Hauser |
| 2022/0015798 A1 | 1/2022 | Marchand et al. |
| 2022/0022898 A1 | 1/2022 | Cox et al. |
| 2022/0039815 A1 | 2/2022 | Thress et al. |
| 2022/0125451 A1 | 4/2022 | Hauser |
| 2022/0142638 A1 | 5/2022 | Enright et al. |
| 2022/0151647 A1 | 5/2022 | Dolendo et al. |
| 2022/0152355 A1 | 5/2022 | Dolendo et al. |
| 2022/0160381 A1 | 5/2022 | Hauser |
| 2022/0160382 A1 | 5/2022 | Hauser |
| 2022/0160383 A1 | 5/2022 | Hauser |
| 2022/0211400 A1 | 7/2022 | Cox et al. |
| 2022/0211992 A1 | 7/2022 | Merritt et al. |
| 2022/0240959 A1 | 8/2022 | Quick |
| 2022/0346800 A1 | 11/2022 | Merritt et al. |
| 2022/0346813 A1 | 11/2022 | Quick |
| 2022/0346814 A1 | 11/2022 | Quick |
| 2022/0347455 A1 | 11/2022 | Merritt et al. |
| 2022/0362512 A1 | 11/2022 | Quick et al. |

FOREIGN PATENT DOCUMENTS

| | | |
|---|---|---|
| CN | 103764049 | 4/2014 |
| CN | 103932756 | 7/2014 |
| CN | 104068910 | 10/2014 |
| CN | 108348319 | 7/2018 |
| CN | 110652645 | 1/2020 |
| CN | 111281482 | 6/2020 |
| DE | 102017004383 | 7/2018 |
| EP | 1254634 | 11/2002 |
| EP | 1867290 | 2/2013 |
| GB | 1588072 | 4/1981 |
| GB | 2498349 | 7/2013 |
| JP | H6190049 | 7/1994 |
| JP | H07323090 A | 12/1995 |
| JP | 2001522631 | 5/1999 |
| JP | 2004097807 | 4/2004 |
| JP | 2005-095242 | 6/2005 |
| JP | 2005230132 | 9/2005 |

(56) References Cited

FOREIGN PATENT DOCUMENTS

| | | |
|---|---|---|
| JP | 2005323702 | 11/2005 |
| JP | 2006094876 | 4/2006 |
| JP | 2011526820 | 1/2010 |
| WO | WO1997017889 | 5/1997 |
| WO | WO9833443 | 8/1998 |
| WO | WO9838920 | 9/1998 |
| WO | WO9839053 | 9/1998 |
| WO | WO9851237 | 11/1998 |
| WO | WO1999044542 | 9/1999 |
| WO | WO0032118 | 6/2000 |
| WO | WO2000053120 | 9/2000 |
| WO | WO0202162 | 1/2002 |
| WO | WO03015840 | 2/2003 |
| WO | WO2004018916 | 3/2004 |
| WO | WO2004093696 | 11/2004 |
| WO | WO2005046736 | 5/2005 |
| WO | WO2006110186 | 10/2006 |
| WO | WO2007092820 | 8/2007 |
| WO | WO2009082513 | 7/2009 |
| WO | WO2009086482 | 7/2009 |
| WO | WO2009155571 | 12/2009 |
| WO | WO2010002549 | 1/2010 |
| WO | WO2010010545 | 1/2010 |
| WO | WO2010023671 | 3/2010 |
| WO | WO2010049121 | 5/2010 |
| WO | WO2010102307 | 9/2010 |
| WO | WO2011032712 | 3/2011 |
| WO | WO2011054531 | 5/2011 |
| WO | WO2011073176 | 6/2011 |
| WO | WO2012009675 | 1/2012 |
| WO | WO2012011097 | 1/2012 |
| WO | WO2012049652 | 4/2012 |
| WO | WO2012065748 | 5/2012 |
| WO | WO2012120490 | 9/2012 |
| WO | WO2012162437 | 11/2012 |
| WO | WO2014047650 | 3/2014 |
| WO | WO2014081892 | 5/2014 |
| WO | WO2015006782 | 1/2015 |
| WO | WO2015061365 | 4/2015 |
| WO | WO2015121424 | 8/2015 |
| WO | WO2015189354 | 12/2015 |
| WO | WO2015191646 | 12/2015 |
| WO | WO2017024258 | 2/2017 |
| WO | WO2017058280 | 4/2017 |
| WO | WO2017070702 | 4/2017 |
| WO | WO2017106877 | 6/2017 |
| WO | WO2017189535 | 11/2017 |
| WO | WO2017189550 | 11/2017 |
| WO | WO2017189591 | 11/2017 |
| WO | WO2017189615 | 11/2017 |
| WO | WO2017210487 | 12/2017 |
| WO | WO2018049317 | 3/2018 |
| WO | WO2018080590 | 5/2018 |
| WO | WO2018148174 | 8/2018 |
| WO | WO2019010318 | 1/2019 |
| WO | WO2019050765 | 3/2019 |
| WO | WO2019075444 | 4/2019 |
| WO | WO2019094456 | 5/2019 |
| WO | WO2019222117 | 11/2019 |
| WO | WO2019246240 | 12/2019 |
| WO | WO2020036809 | 2/2020 |
| WO | WO2021067134 | 4/2021 |
| WO | WO2021076954 | 4/2021 |
| WO | WO2021127202 | 6/2021 |
| WO | WO2021248042 | 12/2021 |
| WO | WO2022032173 | 2/2022 |
| WO | WO2022103848 | 5/2022 |
| WO | WO2022109021 | 5/2022 |
| WO | WO2022109034 | 5/2022 |

OTHER PUBLICATIONS

Gibbs, et al., "Temporary Stent as a bail-out device during percutaneous transluminal coronary angioplasty: preliminary clinical experience," British Heart Journal, 1994, 71:372-377, Oct. 12, 1993, 6 pgs.

Gupta, S. et al., "Acute Pulmonary Embolism Advances in Treatment", JAPI, Association of Physicians India, Mar. 2008, vol. 56, 185-191.

International Search Report and Written Opinion for International App. No. PCT/US13/61470, dated Jan. 17, 2014, 7 pages.

International Search Report and Written Opinion for International App. No. PCT/US2014/046567, dated Nov. 3, 2014, 13 pages.

International Search Report and Written Opinion for International App. No. PCT/US2014/061645, dated Jan. 23, 2015, 15 pages.

International Search Report for International App. No. PCT/US13/71101, dated Mar. 31, 2014, 4 pages.

Konstantinides, S. et al., "Pulmonary embolism hotline 2012—Recent and expected trials", Thrombosis and Haemostasis, Jan. 9, 2013:33; 43-50.

Konstantinides, S. et al., "Pulmonary embolism: risk assessment and management", European Society of Cardiology; European Heart Journal, Sep. 7, 2012:33, 3014-3022.

Kucher, N. et al., "Percutaneous Catheter Thrombectomy Device for Acute Pulmonary Embolism: In Vitro and in Vivo Testing", Circulation, Sep. 2005:112:e28-e32.

Kucher, N., "Catheter Interventions in Massive Pulmonary Embolism", Cardiology Rounds, Mar. 2006 vol. 10, Issue 3, 6 pages.

Kucher, N. et al., "Management of Massive Pulmonary Embolism", Radiology, Sep. 2005:236:3 852-858.

Kucher, N. et al., "Randomized, Controlled Trial of Ultrasound-Assisted Catheter-Directed Thrombolysis for Acute Intermediate-Risk Pulmonary Embolism." Circulation, 2014, 129, pp. 9 pages.

Kuo, W. et al., "Catheter-directed Therapy for the Treatment of Massive Pulmonary Embolism: Systematic Review and Meta-analysis of Modern Techniques", Journal of Vascular and Interventional Radiology, Nov. 2009:20:1431-1440.

Kuo, W. et al., "Catheter-Directed Embolectomy, Fragmentation, and Thrombolysis for the Treatment of Massive Pulmonary Embolism After Failure of Systemic Thrombolysis", American College of CHEST Physicians 2008: 134:250-254.

Kuo, W. MD, "Endovascular Therapy for Acute Pulmonary Embolism", Continuing Medical Education Society of Interventional Radiology ("CME"); Journal of Vascular and Interventional Radiology, Feb. 2012: 23:167-179.

Lee, L. et al, "Massive pulmonary embolism: review of management strategies with a focus on catheter-based techniques", Expert Rev. Cardiovasc. Ther. 8(6), 863-873 (2010).

Liu, S. et al, "Massive Pulmonary Embolism: Treatment with the Rotarex Thrombectomy System", Cardiovascular Interventional Radiology; 2011: 34:106-113.

Muller-Hulsbeck, S. et al. "Mechanical Thrombectomy of Major and Massive Pulmonary Embolism with Use of the Amplatz Thrombectomy Device", Investigative Radiology, Jun. 2001:36:6:317-322.

Reekers, J. et al., "Mechanical Thrombectomy for Early Treatment of Massive Pulmonary Embolism", Cardiovascular and Interventional Radiology, 2003: 26:246-250.

Schmitz-Rode et al., "New Mesh Basket for Percutaneous Removal of Wall-Adherent Thrombi in Dialysis Shunts," Cardiovasc Intervent Radiol 16:7-10 1993 4 pgs.

Schmitz-Rode et al., "Temporary Pulmonary Stent Placement as Emergency Treatment of Pulmonary Embolism," Journal of the American College of Cardiology, vol. 48, No. 4, 2006 (5 pgs.).

Schmitz-Rode, T. et al., "Massive Pulmonary Embolism: Percutaneous Emergency Treatment by Pigtail Rotation Catheter", JACC Journal of the American College of Cardiology, Aug. 2000:36:2:375-380.

Spiotta, A et al., "Evolution of thrombectomy approaches and devices for acute stroke: a technical review." J NeuroIntervent Surg 2015, 7, pp. 7 pages.

Svilaas, T. et al., "Thrombus Aspiration During Primary Percutaneous Coronary Intervention." The New England Journal of Medicine, 2008, vol. 358, No. 6, 11 pages.

Tapson, V., "Acute Pulmonary Embolism", The New England Journal of Medicine, Mar. 6, 2008:358:2037-52.

(56) References Cited

OTHER PUBLICATIONS

The Penumbra Pivotal Stroke Trial Investigators, "The Penumbra Pivotal Stroke Trial: Safety and Effectiveness of a New Generation of Mechanical Devices for Clot Removal in Intracranial Large Vessel Occlusive Disease." Stroke, 2009, 40: p. 9 pages.
Truong et al., "Mechanical Thrombectomy of Iliocaval Thrombosis Using a Protective Expandable Sheath," Cardiovasc Intervent Radiol27-254-258, 2004, 5 pgs.
Turk et al., "Adapt Fast study: a direct aspiration first pass technique for acute stroke thrombectomy." J NeuroIntervent Surg, vol. 6, 2014, 6 pages.
Uflacker, R., "Interventional Therapy for Pulmonary Embolism", Journal of Vascular and Interventional Radiology, Feb. 2001: 12:147-164.
Verma, R., MD et al. "Evaluation of a Newly Developed Percutaneous Thrombectomy Basket Device in Sheep With Central Pulmonary Embolisms", *Investigative Radiology*, Oct. 2006, 41, 729-734.
International Search Report and Written Opinion for International App. No. PCT/US2015/034987 filed Jun. 9, 2015, Applicant: Inceptus Medical, LLC, dated Sep. 17, 2015, 12 pages.
English translation of Japanese Office Action received for JP Application No. 2016-564210, Applicant: Inceptus Medical, LLC, dated Sep. 4, 2017, 4 pages.
Australian Exam Report received for AU Application No. 2015274704, Applicant: Inceptus Medical, LLC, dated Sep. 7, 2017, 3 pages.
European Search Report received for EP Application No. 15805810.7, Applicant: Inceptus Medical, LLC, dated Sep. 4, 2017, 6 pages.
International Search Report and Written Opinion for International App. No. PCT/US2016/067628 filed Dec. 19, 2016, Applicant: Inari Medical, Inc., dated Apr. 10, 2017, 11 pages.
Goldhaber, S. et al. "Percutaneous Mechanical Thrombectomy for Acute Pulmonary Embolism—A Double-Edged Sword," American College of CHEST Physicians, Aug. 2007, 132:2, 363-372.
Goldhaber, S., "Advanced treatment strategies for acute pulmonary embolism, including thrombolysis and embolectomy," Journal of Thrombosis and Haemostasis, 2009: 7 (Suppl. 1): 322-327.
International Search Report and Written Opinion for International App. No. PCT/US2017/029696, Date of Filing: Apr. 26, 2017, Applicant: Inari Medical, Inc., dated Sep. 15, 2017, 19 pages.
International Search Report and Written Opinion for International App. No. PCT/US2016/058536, Date of Filing: Oct. 24, 2016, Applicant: Inari Medical, Inc., dated Mar. 13, 2017, 14 pages.
European First Office Action received for EP Application No. 13838945.7, Applicant: Inari Medical, Inc., dated Oct. 26, 2018, 7 pages.
International Search Report and Written Opinion for International App. No. PCT/US2018/048786, Date of Filing: Aug. 30, 2018, Applicant: Inari Medical, Inc., dated Dec. 13, 2018, 12 pages.
International Search Report and Written Opinion for International App. No. PCT/US2018/055780, Date of Filing: Oct. 13, 2018, Applicant: Inceptus Medical LLC., dated Jan. 22, 2019, 8 pages.
European Search Report for European Application No. 16876941.2, Date of Filing: Dec. 19, 2016, Applicant: Inari Medical, Inc., dated Jul. 18, 2019, 7 pages.
Extended European Search Report for European Application No. 16858462.1, Date of Filing: Oct. 24, 2016, Applicant: Inari Medical, Inc., dated Jun. 3, 2019, 10 pages.
International Search Report and Written Opinion for International App. No. PCT/US2019/045794, Date of Filing: Aug. 8, 2019, Applicant: Inari Medical, Inc., dated Nov. 1, 2019, 17 pages.
Partial Supplementary European Search Report for European Application No. 17864818.4, Date of Filing: May 21, 2019, Applicant: Inari Medical, Inc., dated Apr. 24, 2020, 11 pages.
International Search Report and Written Opinion for International App. No. PCT/US2020/056067, Date of Filing: Oct. 16, 2020; Applicant: Inari Medical, Inc., dated Jan. 22, 2021, 8 pages.
Extended European Search Report for European Application No. 20191581.6, Applicant: Inari Medical, Inc., dated Mar. 31, 2021, 11 pages.
International Search Report and Written Opinion for International App. No. PCT/US2020/055645, Date of Filing: Dec. 17, 2020; Applicant: Inari Medical, Inc., dated Apr. 14, 2021, 12 pages.
Extended European Search Report for European Application No. 18853465.5, Applicant: Inari Medical, Inc., dated May 7, 2021, 2021, 7 pages.
Vorwerk, D. MD, et al., "Use of a Temporary Caval Filter to Assist Percutaneous Iliocaval Thrombectomy: Experimental Results." SCVIR, 1995, 4 pages.
Wikipedia; Embolectomy; retrieved from the internet: https://en.wikipedia.org/wiki/Embolectomy; 4 pgs.; retrieved/printed: Mar. 24, 2016.
O'Sullivan; Thrombolysis versus thrombectomy in acute deep vein thrombosis; Interventional Cardiology; 3(5); pp. 589-596; Oct. 2011.
Capture Vascular Systems; (company website); retrieved from the internet: http://www.capturevascular.com; 3 pgs.; retrieved/printed: Mar. 24, 2016.
Edwards Lifesciences; Fogarty® Occlusion Catheters (product brochure); retrieved from the internet: http://web.archive.org/web/20150228193218/http://www.edwards.com/products/vascular/atraumaticocclusion/pages/occlusioncatheter.aspx; © 2011; 2 pgs.; retrieved/printed: Mar. 24, 2011.
Boston Scientific; Fetch(TM) 2 Aspiration Catheter (product information);retrieved from the internet: http://www.bostonscientific.com/en-US/products/thrombectomy-systems/fetch2-aspiration-catheter.html; 2 pgs.; retrieved/printed: Mar. 24, 2016.
Penumbra, Inc.; Indigo® System (product information); retrieved from the internet: http://www.penumbrainc.com/peripherallpercutaneous-thromboembolectomy/indigo-system; 7 pgs.; retrieved/printed: Mar. 24, 2016.
Youtube; Merci Retrieval System X Series Animation; uploaded Mar. 16, 2009 (product information); posted on May 7, 2009 by SSMDePaul, time 1:09, retrieved from the internet: https://www.youtube.com/watch?v=MGX7deuFkhc; 3 pgs.; retrieved/printed: Mar. 24, 2016.
Covidien; Solitaire(TM) AS Neurovascular Remodeling Device (product information); retrieved from the internet: http://www.ev3.net/neuro/intl/remodeling-devices/solitaire-ab.htm; © 2015; 2 pgs.; retrieved/printed: Mar. 24, 2016.
International Search Report and Written Opinion for International App. No. PCT/US21/35965, Date of Filing: Jun. 4, 2021, Applicant: Inari Medical, Inc., dated Sep. 28, 2021, 12 pages.
International Search Report and Written Opinion for International App. No. PCT/US21/45072 Date of Filing: Aug. 6, 2021, Applicant: Inari Medical, Inc., dated Jan. 20, 2022, 10 pages.
International Search Report and Written Opinion for International App. No. PCT/US21/58793; Date of Filing: Nov. 10, 2021, Applicant: Inari Medical, Inc., dated Mar. 16, 2022, 13 pages.
International Search Report and Written Opinion for International App. No. PCT/US21/59718; Date of Filing: Nov. 17, 2021, Applicant: Inari Medical, Inc., dated Mar. 22, 2022, 13 pages.
International Search Report and Written Opinion for International App. No. PCT/US21/59735; Date of Filing: Nov. 17, 2021, Applicant: Inari Medical, Inc., dated Mar. 22, 2022, 11 pages.

\* cited by examiner

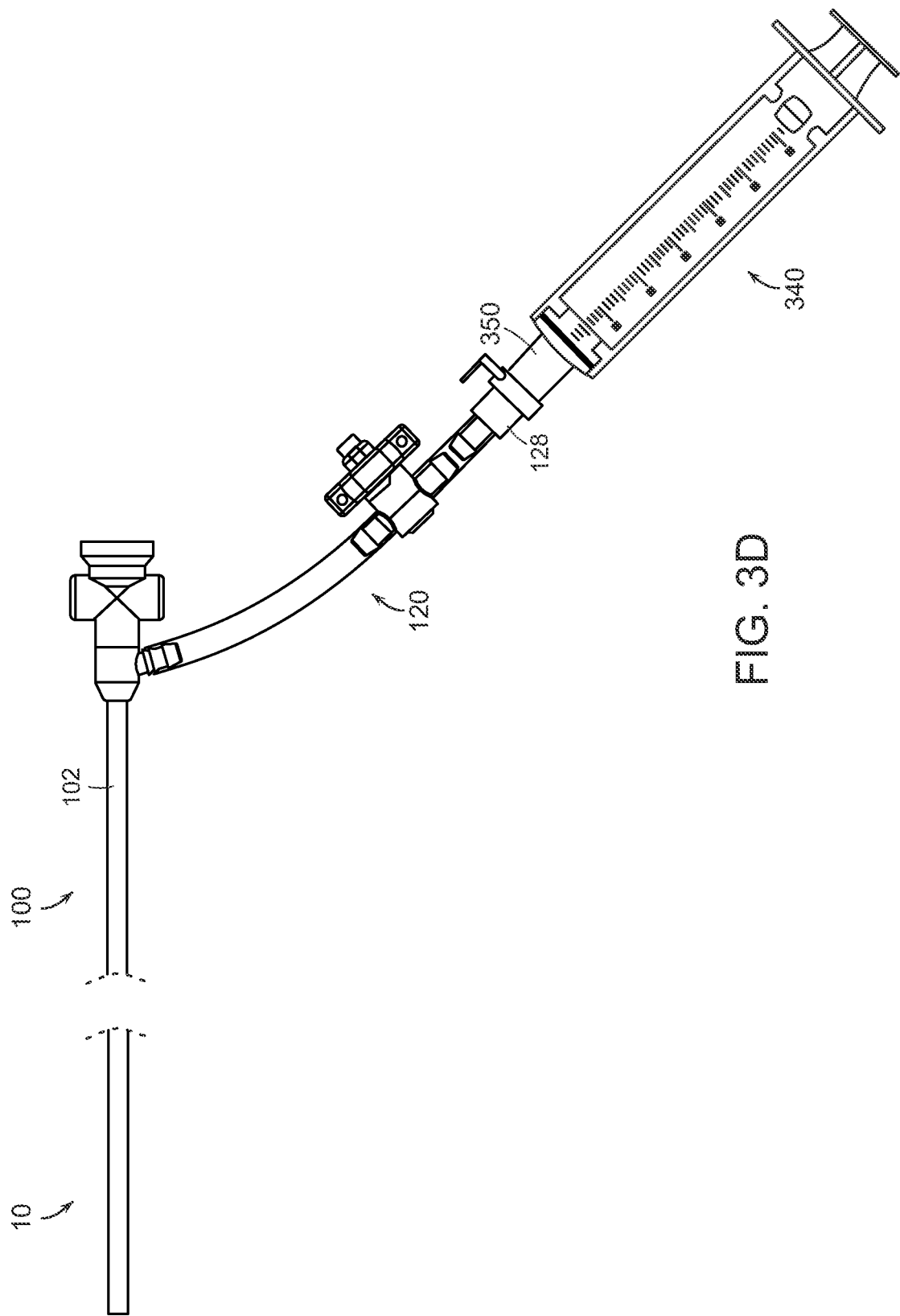

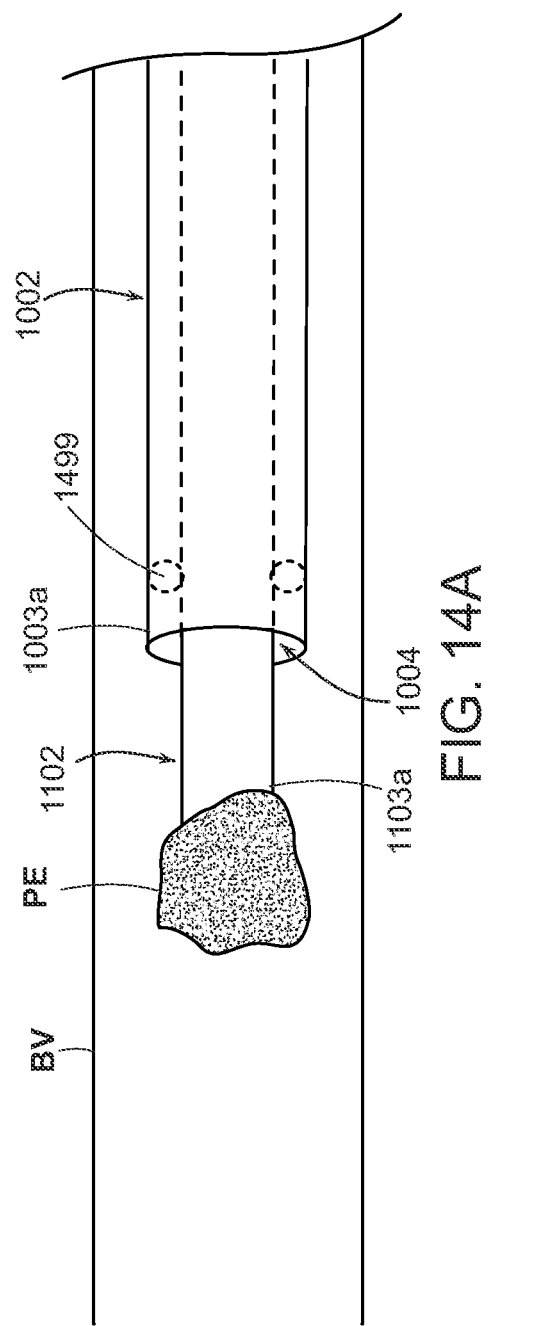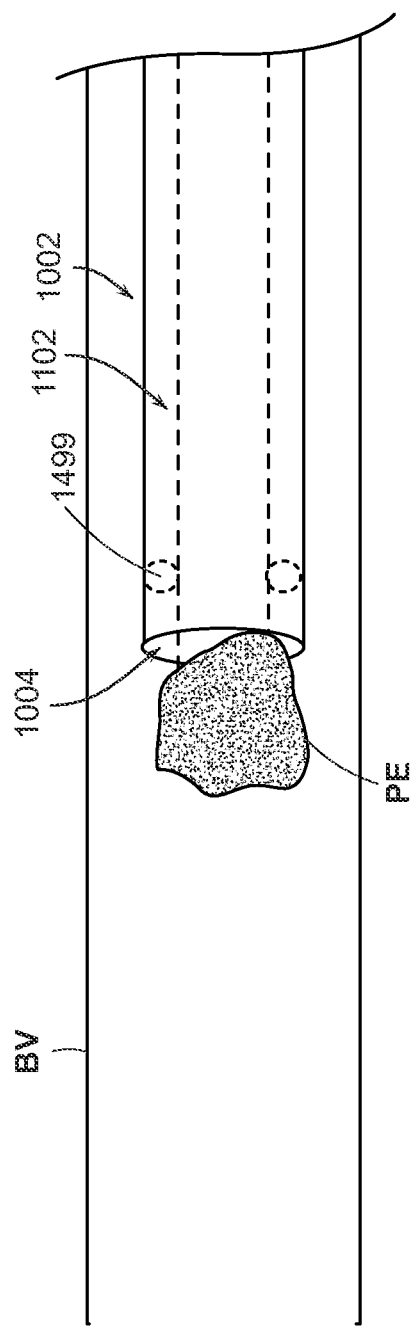

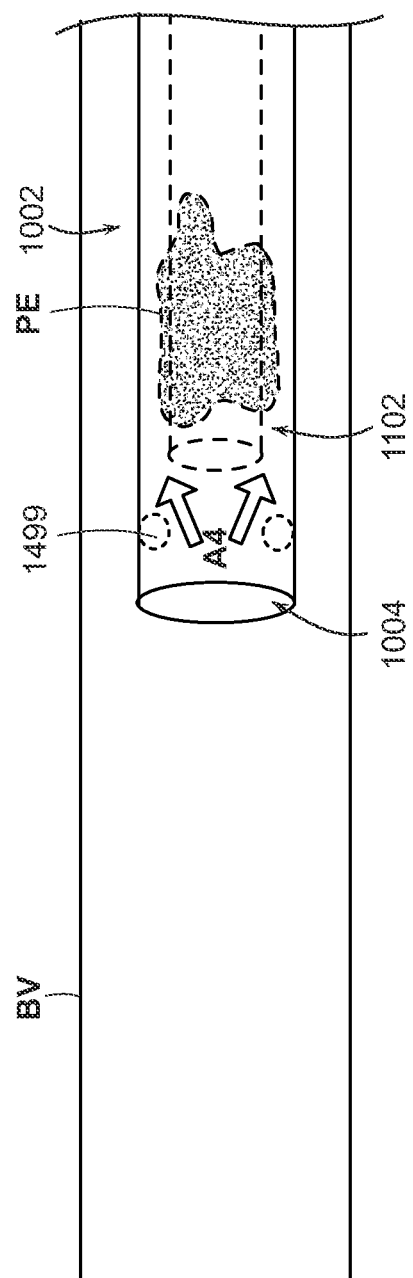

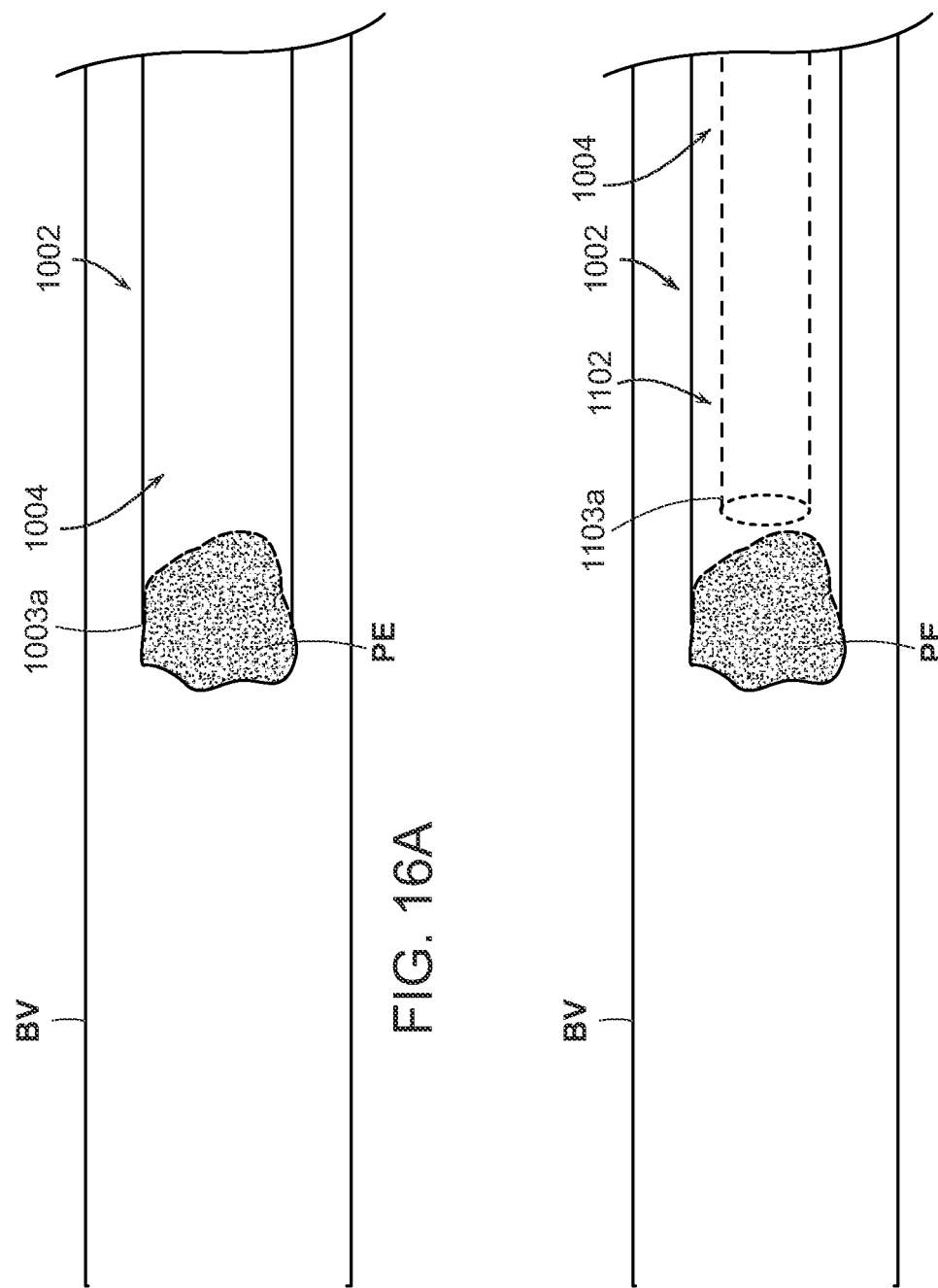

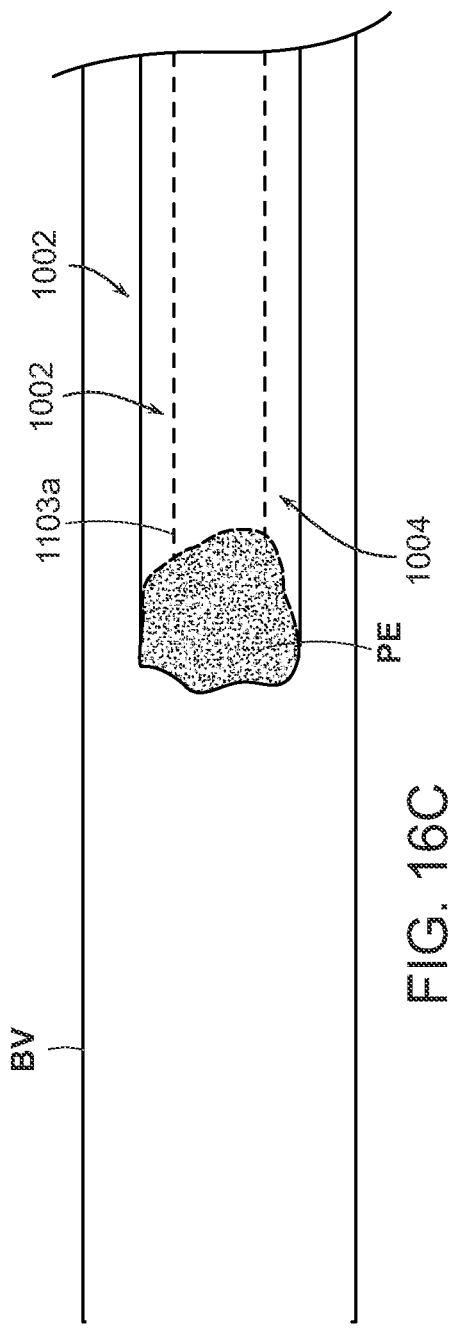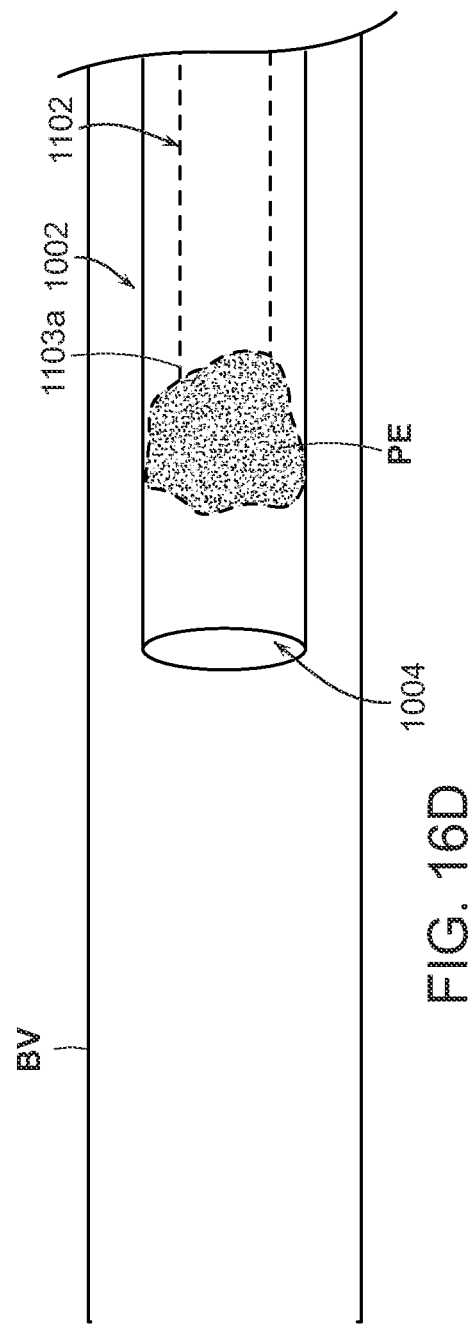

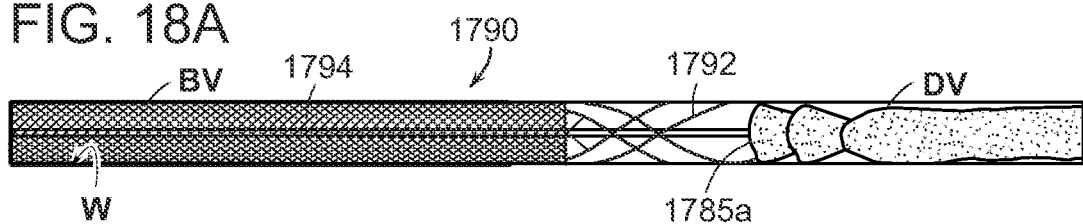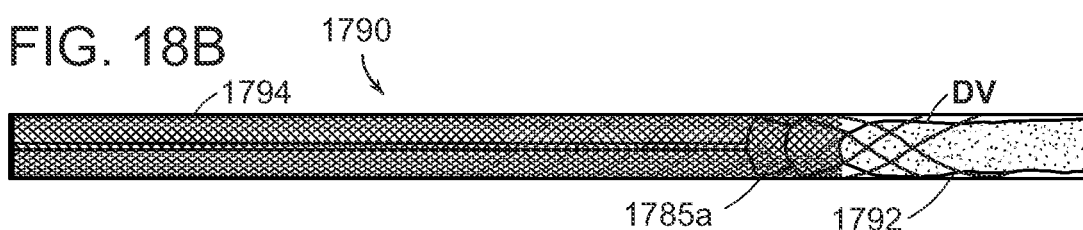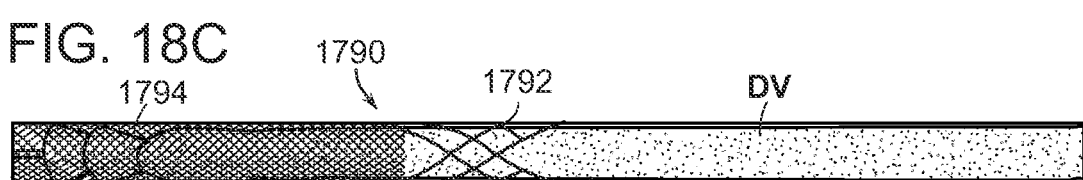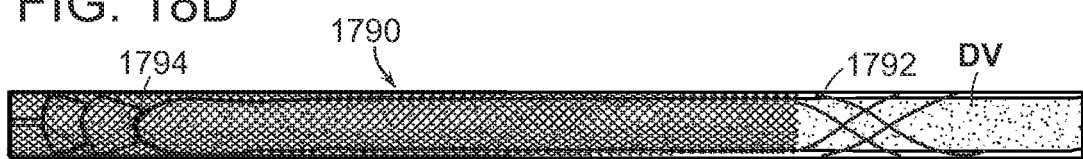

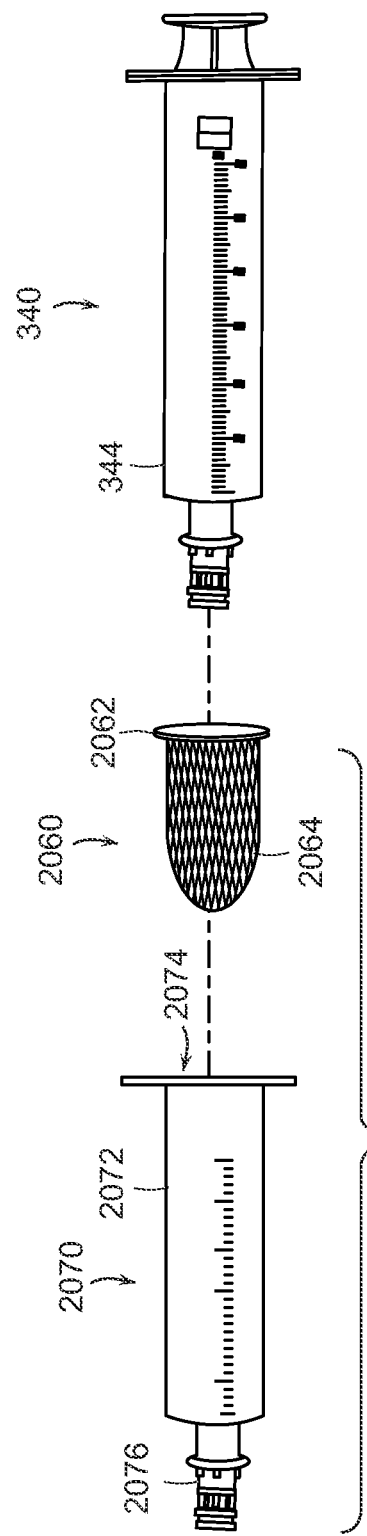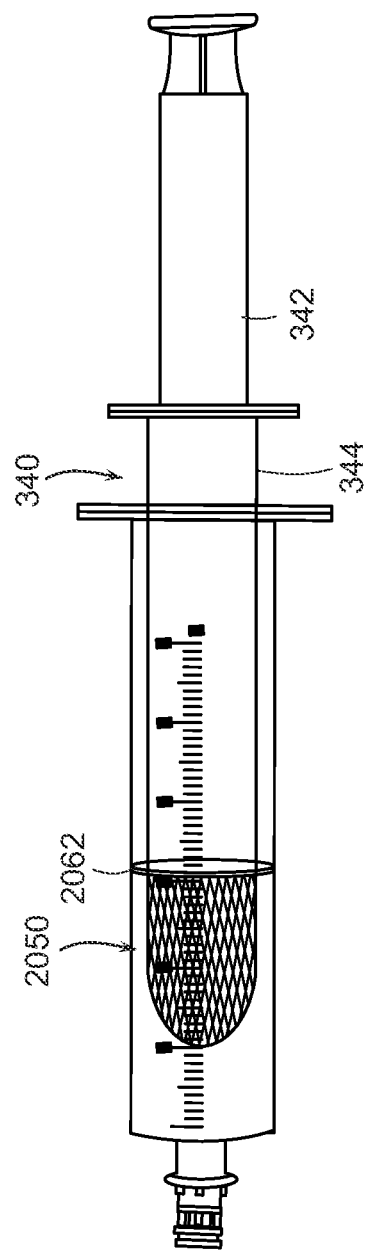
FIG. 20A
FIG. 20B

SYSTEM FOR TREATING EMBOLISM AND ASSOCIATED DEVICES AND METHODS

CROSS-REFERENCES TO RELATED APPLICATIONS

This application is a continuation of U.S. patent application Ser. No. 16/536,185, filed Aug. 8, 2019, which claims the benefit of U.S. Provisional Patent Application No. 62/718,269, filed on Aug. 13, 2018, and U.S. Provisional Patent Application No. 62/718,248, filed on Aug. 13, 2018, each of which is herein incorporated by reference in its entirety.

TECHNICAL FIELD

The present technology relates generally to systems, methods, and devices for the intravascular treatment of emboli and/or thrombi within a blood vessel of a human patient. In particular, some embodiments of the present technology relate to systems for releasing stored vacuum pressure to aspirate clot material from a blood vessel.

BACKGROUND

Thromboembolic events are characterized by an occlusion of a blood vessel. Thromboembolic disorders, such as stroke, pulmonary embolism, heart attack, peripheral thrombosis, atherosclerosis, and the like, affect many people. These disorders are a major cause of morbidity and mortality.

When an artery is occluded by a clot, tissue ischemia develops. The ischemia will progress to tissue infarction if the occlusion persists. However, infarction does not develop or is greatly limited if the flow of blood is reestablished rapidly. Failure to reestablish blood flow can accordingly lead to the loss of limb, angina pectoris, myocardial infarction, stroke, or even death.

In the venous circulation, occlusive material can also cause serious harm. Blood clots can develop in the large veins of the legs and pelvis, a common condition known as deep venous thrombosis (DVT). DVT commonly occurs where there is a propensity for stagnated blood (e.g., long distance air travel, immobility, etc.) and clotting (e.g., cancer, recent surgery, such as orthopedic surgery, etc.). DVT can obstruct drainage of venous blood from the legs leading to swelling, ulcers, pain and infection. DVT can also create a reservoir in which blood clots can collect and then travel to other parts of the body including the heart, lungs, brain (stroke), abdominal organs, and/or extremities.

In the pulmonary circulation, the undesirable material can cause harm by obstructing pulmonary arteries—a condition known as pulmonary embolism. If the obstruction is upstream, in the main or large branch pulmonary arteries, it can severely compromise total blood flow within the lungs, and therefore the entire body. This can result in low blood pressure and shock. If the obstruction is downstream, in large to medium pulmonary artery branches, it can prevent a significant portion of the lung from participating in the exchange of gases to the blood resulting in low blood oxygen and buildup of blood carbon dioxide.

There are many existing techniques to reestablish blood flow through an occluded vessel. Embolectomies, for example, are a surgical technique involving incising a blood vessel and placing a balloon-tipped device (such as the Fogarty catheter) at the location of the occlusion. The balloon is then inflated at a point beyond the clot and used to withdraw the obstructing material back to the point of incision. The obstructing material is then removed by the surgeon. Although such surgical techniques have been useful, exposing a patient to surgery may be traumatic and best avoided when possible. Additionally, the use of a Fogarty catheter may be problematic due to the possible risk of damaging the interior lining of the vessel as the catheter is being withdrawn.

Percutaneous methods are also utilized for reestablishing blood flow. A common percutaneous technique is referred to as balloon angioplasty where a balloon-tipped catheter is introduced to a blood vessel (e.g., typically through an introducing catheter). The balloon-tipped catheter is then advanced to the point of the occlusion and inflated to dilate the stenosis. Balloon angioplasty is appropriate for treating vessel stenosis, but it is generally not effective for treating acute thromboembolisms as none of the occlusive material is removed and restenosis regularly occurs after dilation. Another percutaneous technique involves placing a catheter near the clot and infusing streptokinase, urokinase, or other thrombolytic agents to dissolve the clot. Unfortunately, thrombolysis typically takes hours to days to be successful. Additionally, thrombolytic agents can cause hemorrhage, and in many patients the thrombolytic agents cannot be used at all.

Various devices exist for performing a thrombectomy or removing other foreign material. However, such devices have been found to have structures which are either highly complex, cause trauma to the treatment vessel, or lack the ability to be appropriately fixed against the vessel. Furthermore, many of the devices have highly complex structures that lead to manufacturing and quality control difficulties as well as delivery issues when passing through tortuous or small diameter catheters. Less complex devices may allow the user to pull through the clot, particularly with inexperienced users, and such devices may not completely capture and/or collect all of the clot material.

Thus, there exists a need for improved systems and methods for embolic extraction.

BRIEF DESCRIPTION OF THE DRAWINGS

Many aspects of the present technology can be better understood with reference to the following drawings. The components in the drawings are not necessarily to scale. Instead, emphasis is placed on illustrating clearly the principles of the present disclosure.

FIG. 3D is a side view of the locking syringe of FIG. 3A coupled to the clot removal system of FIG. 1 via the adaptor of FIG. 3B.

FIGS. 13A-14C are schematic illustrations of a distal portion of the clot removal system of FIG. 11 during a clot removal procedure in accordance with the present technology.

FIGS. 16A-16E are schematic illustrations of a distal portion of the clot removal system of FIG. 11 during a clot removal procedure in accordance with the present technology.

FIGS. 18A-18H are side views of a distal portion of the clot removal system shown of FIG. 17 during a clot removal procedure in accordance with the present technology.

FIG. 20A is a partially-exploded side view of a filter device and pressure source configured in accordance with the present technology.

FIG. 20B is a perspective side view of the syringe of FIG. 20A coupled to the filter device of the FIG. 20A.

DETAILED DESCRIPTION

Figure 1:
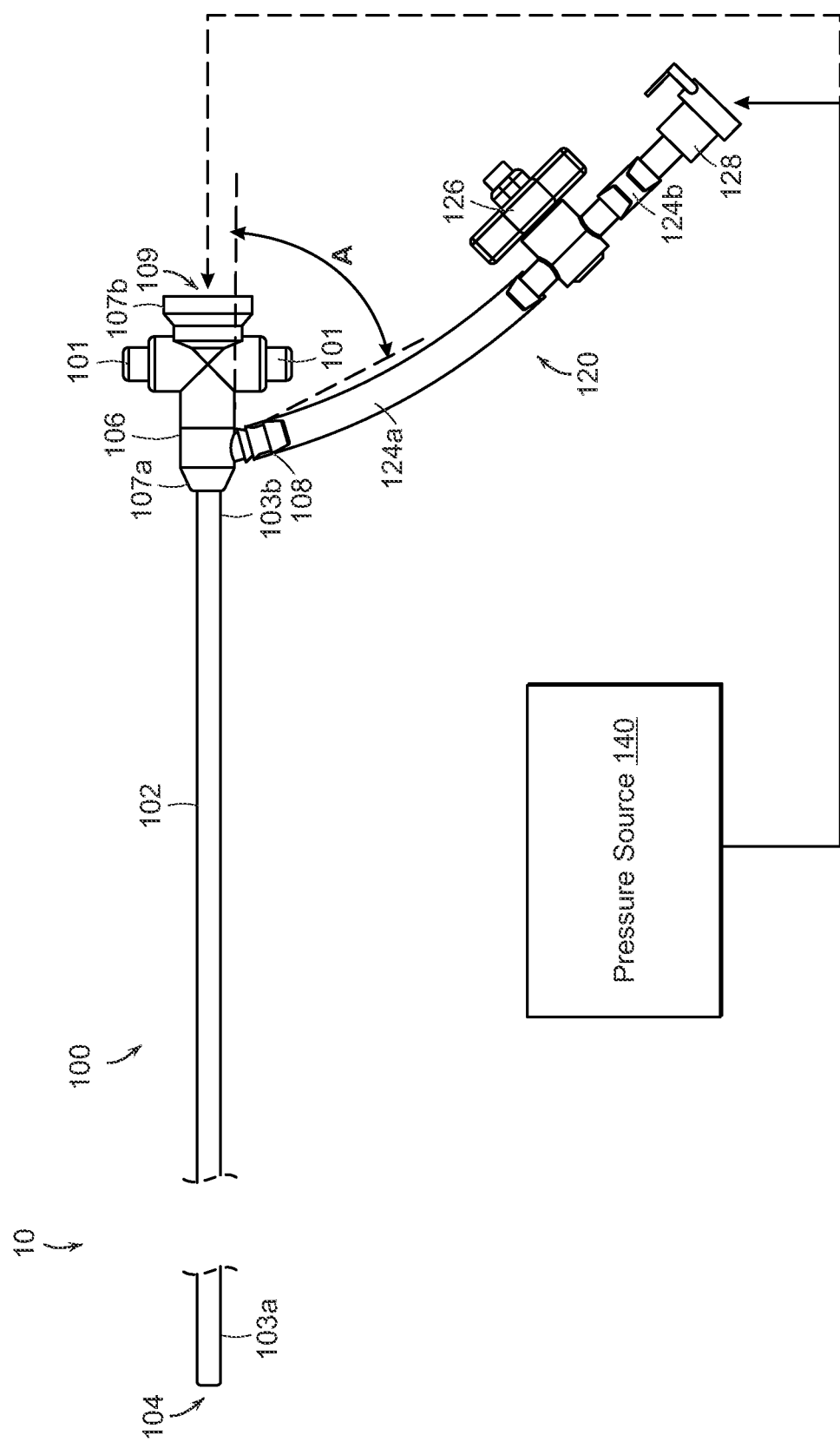
FIG. 1 is a partially schematic side view of a clot removal system configured in accordance with the present technology.

The present technology is generally directed to methods and systems for removing clot material from a blood vessel of a human patient. In some embodiments, a catheter can be intravascularly positioned within a blood vessel such that a distal portion (e.g., a distal opening) of the catheter is positioned proximate to clot material within the blood vessel. The catheter can be fluidly coupled to a pressure source via a valve or other fluid control device positioned outside of the patient. With the valve closed, the pressure source can be activated to charge a vacuum chamber of the pressure source with a vacuum. The valve can then be opened to apply the vacuum to the catheter to thereby aspirate at least a portion of the clot material from the blood vessel into the catheter. In some embodiments, an interventional device can be delivered through the catheter and used to engage the clot material before and/or after the vacuum is applied to the catheter.

In one aspect of the present technology, the pressure source is configured to generate a vacuum and store the vacuum before the pressure source is fluidly connected to the catheter. Therefore, opening the fluid control device can instantaneously or nearly instantaneously apply the stored vacuum pressure to the catheter, thereby generating suction throughout the catheter. In particular, the suction is applied at the distal portion of the catheter proximate to the clot material. Pre-charging or storing the vacuum before applying the vacuum to the catheter can generate greater suction forces (and corresponding fluid flow velocities) at and/or near the distal portion of the catheter compared to, for example, simply activating the pressure source while it is fluidly connected to the catheter. The greater suction forces generated by application of the stored vacuum can be used to aspirate or otherwise remove clot material from within a blood vessel of a human patient.

Although many of the embodiments are described below with respect to devices, systems, and methods for treating a pulmonary embolism, other applications and other embodiments in addition to those described herein are within the scope of the technology (e.g., intravascular procedures other than the treatment of emboli, intravascular procedures for treating cerebral embolism, intravascular procedures for treating deep vein thrombosis (DVT), etc.). Additionally, several other embodiments of the technology can have different configurations, states, components, or procedures than those described herein. Moreover, it will be appreciated that specific elements, substructures, advantages, uses, and/or other features of the embodiments described with reference to FIGS. 1-25 can be suitably interchanged, substituted or otherwise configured with one another in accordance with additional embodiments of the present technology. Furthermore, suitable elements of the embodiments described with reference to FIGS. 1-25 can be used as standalone and/or self-contained devices. A person of ordinary skill in the art, therefore, will accordingly understand that the technology can have other embodiments with additional elements, or the technology can have other embodiments without several of the features shown and described below with reference to FIGS. 1-25.

With regard to the terms "distal" and "proximal" within this description, unless otherwise specified, the terms can reference a relative position of the portions of a catheter subsystem with reference to an operator and/or a location in the vasculature. Also, as used herein, the designations "rearward," "forward," "upward," "downward," etc. are not meant to limit the referenced component to use in a specific orientation. It will be appreciated that such designations refer to the orientation of the referenced component as illustrated in the Figures; the systems of the present technology can be used in any orientation suitable to the user.

The headings provided herein are for convenience only and should not be construed as limiting the subject matter disclosed.

I. Selected Embodiments of Clot Removal Systems

FIG. 1 is a partially schematic side view of a clot treatment or clot removal system comprising an aspiration assembly 10 ("assembly 10") configured in accordance with an embodiment of the present technology. In the illustrated embodiment, the assembly 10 includes a catheter subsystem 100, a tubing subsystem 120, and a pressure source 140. The catheter subsystem 100 includes a catheter 102 (e.g., an aspiration catheter) comprising an elongated shaft defining a lumen 104 and having a distal portion 103a and a proximal portion 103b. The catheter subsystem 100 further includes a valve 106 that can be integral with or coupled to the proximal portion 103b of the catheter 102.

In the illustrated embodiment, the valve 106 includes a distal portion 107a, a proximal portion 107b, and a lumen 109 extending therethrough from the distal portion 107a to the proximal portion 107b. The valve 106 further includes a flow controller (obscured in FIG. 1) in the lumen 109. In some embodiments, the valve is a hemostasis valve that is configured to maintain hemostasis during a clot removal procedure by preventing fluid flow in the proximal direction through the valve 106 as various components such as delivery sheaths, pull members, guidewires, interventional devices, other aspiration catheters (e.g., as described in detail with reference to FIGS. 11-16E), etc., are inserted through the valve 106 to be delivered through the catheter 102 to a treatment site in a blood vessel. The valve 106 further includes a branch or side port 108 positioned distally of the flow controller in the lumen 109 and configured to fluidly couple the lumen 104 of the catheter 102 to the tubing subsystem 120. In the illustrated embodiment, the valve 106 includes buttons 101 that can be actuated (e.g., depressed) to open a conduit within the lumen 109. In some embodiments, the valve 106 can be a valve of the type disclosed in U.S. patent application Ser. No. 16/117,519, filed Aug. 30, 2018, and titled "HEMOSTASIS VALVES AND METHODS OF USE," which is incorporated herein by reference in its entirety. In some embodiments, the proximal portion 107b of the valve 106 is further configured to be detachably coupled (e.g., via a snap-fit arrangement) to a retraction/aspiration device for aspirating the lumen 104 of the catheter 102 and/or for retracting an interventional device, catheter, delivery sheath, catheter, etc., positioned within the lumen 104. Specific details of such retraction/aspiration devices and associated methods are disclosed in U.S. Pat. No. 9,526,864, filed Jun. 9, 2015, and titled "RETRACTION AND ASPIRATION DEVICE FOR TREATING EMBOLISM AND ASSOCIATED SYSTEMS AND METHODS," which is incorporated herein by reference in its entirety.

The tubing subsystem 120 fluidly couples the catheter subsystem 100 to the pressure source 140. More specifically, the tubing subsystem 120 can include one or more tubing sections 124 (individually labeled as a first tubing section 124a and a second tubing section 124b), at least one fluid control device 126 (e.g., a valve), and at least one connector 128 for fluidly coupling the tubing subsystem 120 to the pressure source 140 and/or other suitable components. More specifically, in the illustrated embodiment, the fluid control device 126 is a stopcock that is fluidly coupled to (i) the side port 108 of the valve 106 via the first tubing section 124a and (ii) the connector 128 via the second tubing section 124b. In some embodiments, the fluid control device 126 can define a lumen having a diameter (or other cross-sectional dimension) that is greater than or equal to a diameter of the lumen 104 of the catheter 102, a diameter of the first tubing section 124a, and/or a diameter of the second tubing section 124b.

The fluid control device 126 is externally operable by a user to regulate the flow of fluid therethrough and, specifically, from the lumen 104 of the catheter 102 to the pressure source 140. In other embodiments, the fluid control device 126 can be a clamp that can be actuated (e.g., compressed or squeezed by the hand of a user) to partially or fully restrict fluid flow through the tubing section 124a and/or the tubing section 124b. In yet other embodiments, the fluid control device 126 can be omitted and its functionality incorporated into the pressure source 140 (e.g., as described in detail below with reference to FIG. 5). In some embodiments, the fluid control device 126 can include a quick-release mechanism (e.g., a spring-loaded apparatus) for rapidly opening, unclamping, etc., the fluid control device 126 to (e.g., instantaneously or nearly instantaneously) fluidly connect the pressure source 140 and the catheter 102. In some embodiments, the fluid control device 126 can be opened/closed automatically (e.g., by a motor, switch, etc.). When the pressure source 140 is pre-charged with a vacuum, as described in detail below, such a quick-release fluid control device 126 can reduce the time needed for pressure in the assembly 10 to equalize after opening of the fluid control device 126, and can thereby increase suction forces generated at the distal portion 103a of the catheter 102.

In some embodiments, the connector 128 is a quick-release connector (e.g., a quick disconnect fitting) that enables rapid coupling/decoupling of the catheter 102 and the fluid control device 126 to/from the pressure source 140. In other embodiments, the tubing subsystem 120 can have more or fewer tubing sections, connectors, and/or fluid control devices, and can have other suitable configurations. In some embodiments, one or more of the components can be permanently connected and/or integrally formed.

The pressure source 140 is configured to generate (e.g., form, create, charge, build-up, etc.) a vacuum (e.g., negative relative pressure) and store the vacuum for subsequent application to the catheter subsystem 100. Further details of suitable pressure sources are described in detail below with reference to FIGS. 2-7. During operation of the assembly 10, a user can first close the fluid control device 126 before activating the pressure source 140 to build up vacuum pressure within the pressure source 140 (e.g., a vacuum chamber of the pressure source 140). In some embodiments, the user can control or select the volume of the generated vacuum. In this manner, a vacuum is charged within the pressure source 140 before the pressure source 140 is fluidly connected to the catheter subsystem 100. To aspirate the lumen 104 of the catheter 102, the user can open the fluid control device 126 to fluidly connect the pressure source 140 to the catheter subsystem 100 and thereby apply or release the vacuum stored in the pressure source 140 to the lumen 104 of the catheter 102. Opening of the fluid control device 126 instantaneously or nearly instantaneously applies the stored vacuum pressure to the tubing subsystem 120 and the catheter 102, thereby generating suction throughout the catheter 102. In particular, the suction is applied at the distal portion 103a of the catheter 102. In one aspect of the present technology, pre-charging or storing the vacuum before applying the vacuum to the lumen 104 of the catheter 102 is expected to generate greater suction forces (and corresponding fluid flow velocities) at and/or near the distal portion 103a of the catheter 102 compared to simply activating the pressure source 140 while it is fluidly connected to the catheter 102. As described in detail below, the suction forces generated by application of the stored vacuum can be used to aspirate or otherwise remove clot material from within a blood vessel of a human patient.

II. Selected Embodiments of Pressure Sources for Use with Clot Removal Systems

As described in detail above with reference to FIG. 1, the assembly 10 of the present technology includes a pressure source (e.g., a vacuum source, negative pressure source, etc.) configured to charge a vacuum that can be applied to the catheter subsystem 100 to generate suction forces for aspirating clot material from within a blood vessel. In general, the pressure source can be any suitable source or combination of sources for generating and/or storing negative pressure. In some embodiments, the pressure source can be a pump (e.g., an electric pump coupled to a vacuum chamber) while, in other embodiments, the pressure source can include one or more syringes that can be actuated or otherwise activated by a user of the assembly 10 to generate and store a vacuum therein.

Figure 2:
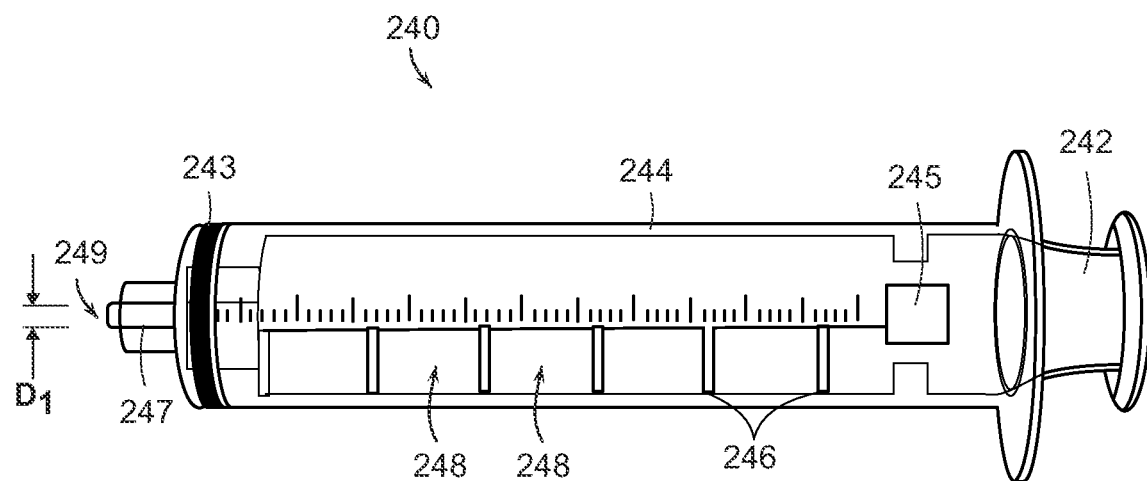
FIG. 2 is a side view of a locking syringe configured in accordance with the present technology.

FIG. 2 is a side view of a pressure source 240 comprising a vacuum-pressure locking syringe ("syringe 240") configured in accordance with the present technology. In some embodiments, the syringe 240 can be of the kind sold under the trademark "VacLok" by Merit Medical System, Inc. In the illustrated embodiment, the syringe 240 includes a plunger 242 slidably and rotatably positioned within a chamber or barrel 244. The barrel 244 is shown as transparent in FIG. 2 for the sake of clarity. The plunger 242 includes a seal 243 and a plurality of index members 246 defining slots 248 between adjacent pairs thereof. A tab member 245 projects inwardly from the interior surface of the barrel 244 and is configured to be removably positioned in the slots 248 for locking the plunger 242 in position relative to the barrel 244. In some embodiments, the barrel 244 can be made of a transparent material that permits a user to visualize material (e.g., clot material) within the barrel 244 and to visualize the relative position between the slots 248 and tab member 245 for locking the syringe 240.

Referring to both FIGS. 1 and 2 together, the syringe 240 further includes a tip 247 for coupling the syringe 240 to the tubing subsystem 120. In the illustrated embodiment, the tip 247 is a standard luer connector that can be coupled to the connector 128 via one or more suitable adaptors. The tip 247 further defines a lumen or bore 249 having an inner diameter $D_1$. In some embodiments, the diameter $D_1$ is about 0.103", or about 0.080" to about 0.200", or about 0.100" to about 0.150", or about 0.100" to about 0.110". In some embodiments, the inner diameter $D_1$ is about 14 French.

During operation of the assembly 10, a user can first close the fluid control device 126 and then grip the plunger 242 and/or the barrel 244 to withdraw (e.g., retract) the plunger 242 at least partially out of the barrel 244 to thereby generate a vacuum in the barrel 244. Once the user has withdrawn the plunger 242 to a sufficient or desired volume, the user can lock the plunger 242 by rotating the plunger 242 relative to the barrel 244 such that the tab member 245 is positioned within a corresponding one of the slots 248. In other embodiments, the syringe 240 may not be a locking syringe, and the user can instead hold the plunger 242 in position relative to the barrel 244. Moreover, the user can control the volume of the vacuum—by withdrawing the plunger 242 more or less—to provide a desired amount or level of suction/aspiration upon opening of the fluid control device 126. In some embodiments, the syringe has a volume of about 60 cc or less than about 60 cc.

Figure 3A:
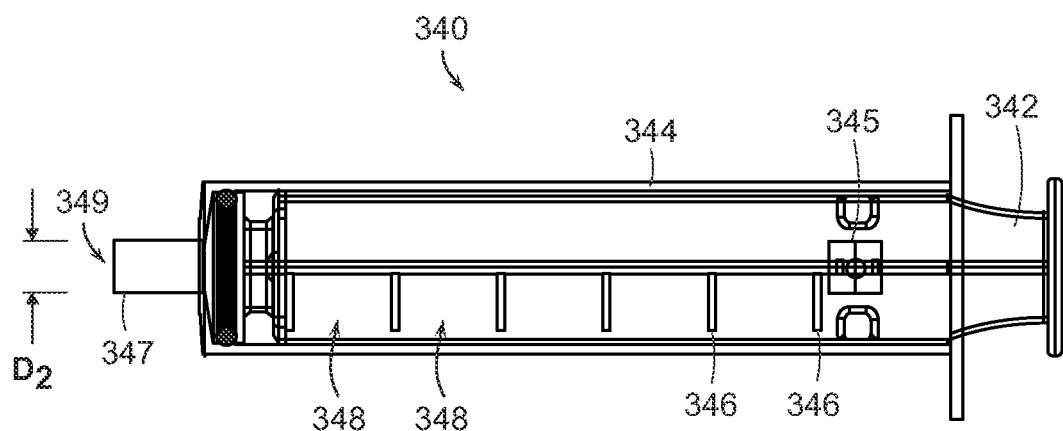
FIG. 3A is a side view of a locking syringe configured in accordance with the present technology.

FIG. 3A is a side view of a pressure source 340 comprising a vacuum-pressure locking syringe ("syringe 340") configured in accordance with the present technology. The syringe 340 can have some features generally similar to the features of the syringe 240 described above with reference to FIG. 2. For example, the syringe 340 includes a plunger 342 slidably and rotatably positioned within a barrel 344, and the plunger 342 includes a plurality of index members 346 defining slots 348 between adjacent pairs thereof. The barrel 344 is shown as transparent in FIG. 3A (and FIG. 3C) for the sake of clarity. While withdrawing the plunger 342, a user can lock the plunger 342 at a specified volume by rotating the plunger 342 relative to the barrel 344 such that a tab member 345 on the interior surface of the barrel 344 is positioned within a corresponding one of the slots 348. In some embodiments, the syringe 340 has a maximum volume of about 60 cc or greater than 60 cc.

In the illustrated embodiment, the syringe 340 includes a large-bore tip 347, such as a Toomey tip, defining an inner lumen or bore 349. In some embodiments, the bore 349 can have an inner diameter $D_2$ that is greater than or equal to the largest inner diameter of the assembly 10 (e.g., of the catheter 102 and tubing subsystem 120). In certain embodiments, the tip 347 can be about 26 French or greater. Accordingly, referring to FIGS. 2 and 3A together, the diameter $D_2$ can be greater than the dimension $D_1$. For example, the dimension $D_2$ can be about two, three, four, or more times greater than the diameter $D_1$.

Figure 3B:
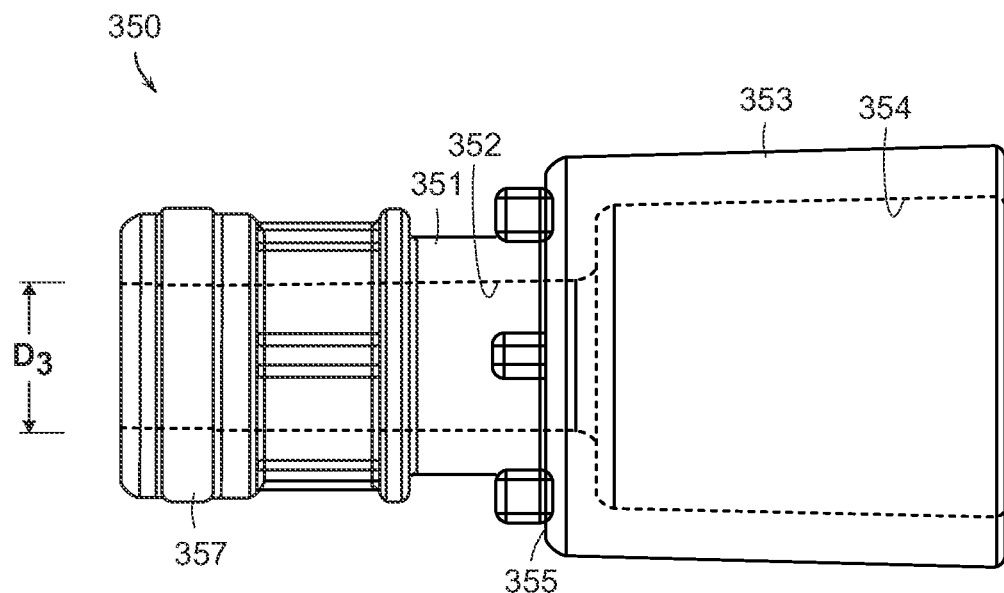
FIG. 3B is a side view of an adaptor for connecting the locking syringe of FIG. 3A to the clot removal system of FIG. 1 configured in accordance with the present technology.
Figure 3C:
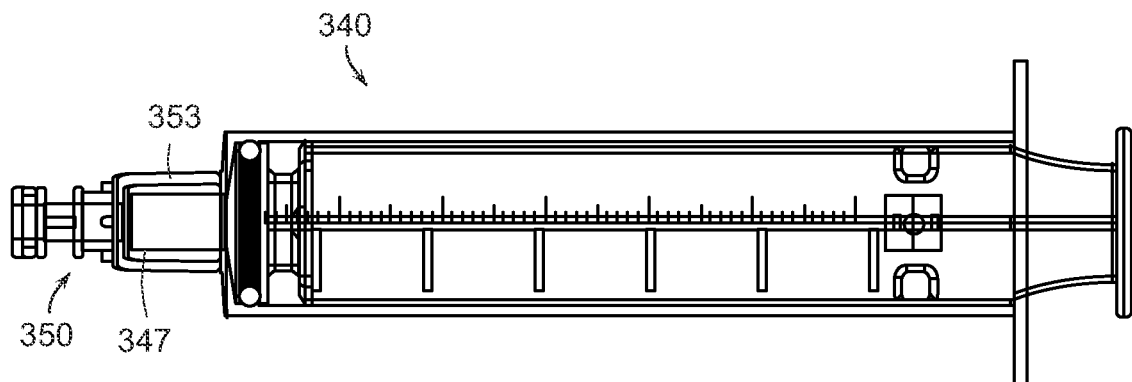
FIG. 3C is a side view of the adaptor of FIG. 3B coupled to the locking syringe of FIG. 3A.

FIG. 3B is a side view of an adaptor 350 for connecting the syringe 340 to the catheter subsystem 100 configured in accordance with the present technology. FIG. 3C is a side view of the adaptor 350 coupled to the syringe 340, and FIG. 3D is a side view of the syringe 340 coupled to the tubing subsystem 120 via the adaptor 350. The adaptor 350 is shown as partially transparent in FIG. 3C for the sake of illustration. Referring to FIG. 3B, the, the adaptor 350 includes (i) a first portion 351 defining a first lumen or bore 352 having an inner diameter $D_3$, (ii) a second portion 353 defining a second lumen or bore 354, and (iii) a stepped surface or interface 355 between the first and second portions 351, 353. The first portion 351 can further include a seal 357 such as an O-Ring around an exterior surface thereof.

Referring to FIGS. 3A-3D together, the second bore 354 of the adaptor 350 is configured to removably receive the tip 347 of the syringe 340 therein. In some embodiments, the tip 347 can be snuggly received in the second bore 354 via an interference fit. In some embodiments, a seal (e.g., an O-ring) can be positioned between an exterior surface of the tip 347 and an interior surface of the second bore 354. In other embodiments, the syringe 340 can be permanently coupled or integrally formed with the adaptor 350. The first portion 351 of the adaptor 350 is configured to be removably positioned within the connector 128 of the tubing subsystem 120 to fluidly couple the syringe 340 to the tubing subsystem 120. In some embodiments, the first portion 351 of the adaptor 350 can be pushed into the connector 128 until the interface 355 abuts the connector 128. When the first portion 351 of the adaptor 350 is positioned within the connector 128, the seal 357 seals the interface between the connector 128 and the adaptor 350.

The diameter $D_3$ of the first bore 352 of the adaptor 350 can be selected to be about the same as or greater than the greatest inner diameter of the assembly 10 (e.g., of the catheter 102 and the tubing subsystem 120). For example, the catheter 102 can be about 9 French or greater, and the diameter $D_3$ can be selected to be larger than the size of the catheter 102. Accordingly, when the fluid control device 126 is open, the continuous lumen between the catheter 102 and the syringe 340 can have a generally constant diameter and/or does not contain any narrowing at the interface between the syringe 340 and the tubing subsystem 120. That is, the adaptor 350 can connect the syringe 340 and the tubing subsystem 120 without any restriction or narrowing of the fluid path. In contrast, a standard luer connector (e.g., the syringe 240) can only provide a continuous lumen for catheters of about 8 French or smaller. Any narrowing of the fluid pathway between the catheter 102 and the syringe 340 can reduce the volumetric flow rate (e.g., suction forces and fluid velocities) that can be generated when a vacuum stored in the syringe 340 is applied to the catheter 102.

In general, the syringe 340 and the adaptor 350 can reduce the fluid resistance in the assembly 10 and therefore facilitate a more rapid pressure equalization in the assembly 10 when the fluid control device 126 is opened to apply the charged vacuum to the catheter 102. In some embodiments, for example, when the syringe 240 (FIG. 2) is charged with a 60 cc vacuum and the fluid control device 126 is opened, the pressure in the assembly 10 can take about 1-2 seconds to equalize. In contrast, when the syringe 340 is charged with a 60 cc vacuum and the fluid control device 126 is opened, the pressure in the assembly 10 can take less than about 1 second (e.g., about 0.5 seconds) to equalize. More specifically, Table 1 illustrates representative pressure equalization times and associated flow rates when the syringe 240 is coupled to a 20 French catheter (i.e., the catheter 102). Table 2 illustrates representative pressure equalization times and associated flow rates when the syringe 340 and the adaptor 350 are coupled to a 20 French catheter (i.e., the catheter 102).

TABLE 1

| Pressure Equalization Time (seconds) | Flow Rate (cc/sec) |
| --- | --- |
| 2.0 | 30.0 |
| 1.9 | 31.6 |
| 1.8 | 33.3 |
| 1.7 | 35.3 |
| 1.6 | 37.5 |
| 1.5 | 40.0 |
| 1.4 | 42.9 |
| 1.3 | 46.2 |

TABLE 2

| Pressure Equalization Time (seconds) | Flow Rate (cc/sec) |
| --- | --- |
| 0.9 | 66.7 |
| 0.8 | 75.0 |

TABLE 2-continued

| Pressure Equalization Time (seconds) | Flow Rate (cc/sec) |
| --- | --- |
| 0.7 | 85.7 |
| 0.6 | 100.0 |
| 0.5 | 120.0 |
| 0.4 | 150.0 |
| 0.3 | 200.0 |
| 0.2 | 300.0 |
| 0.1 | 600.0 |

In each instance, the syringe 340 provides for relatively faster equalization times and correspondingly greater flow rates. It is expected that the more rapid pressure equalization and flow rates provided by the syringe 340 will provide correspondingly greater suction forces at the distal portion 103a of the catheter 102. That is, in general, it is expected that increasing the bore size of a syringe used to provide vacuum pressure will provide greater suction forces over a smaller period of time (e.g., will provide a larger vacuum impulse). In some embodiments, the greater suction forces can facilitate the removal of clot material from a blood vessel of a patient even where the clot material is strongly lodged or attached within the blood vessel (e.g., a chronic clot).

Moreover, as shown in FIG. 3D, the adaptor 350 can couple the syringe 340 to the connector 128 without the need for any intervening tubing sections or additional adaptors. This arrangement can minimize the total length, volume, etc., of the components fluidly coupling the catheter 102 to the syringe 340. It is expected that the magnitude of suction forces generated at the distal portion 103a of the catheter 102—e.g., when a vacuum charged in the syringe 340 is applied to the catheter 102 by opening of the fluid control device 126—is proportional to the length of the fluid path between the pressure source 340 and catheter 102. Thus, operation of the assembly 10 with the syringe 340 and adaptor 350 is expected to increase the suction forces generated at the distal portion 103a of the catheter 102. In some embodiments, the greater suction forces can facilitate the removal of clot material from a blood vessel of a patient even where the clot material is strongly lodged or attached within the blood vessel (e.g., a chronic clot).

Figure 4A:
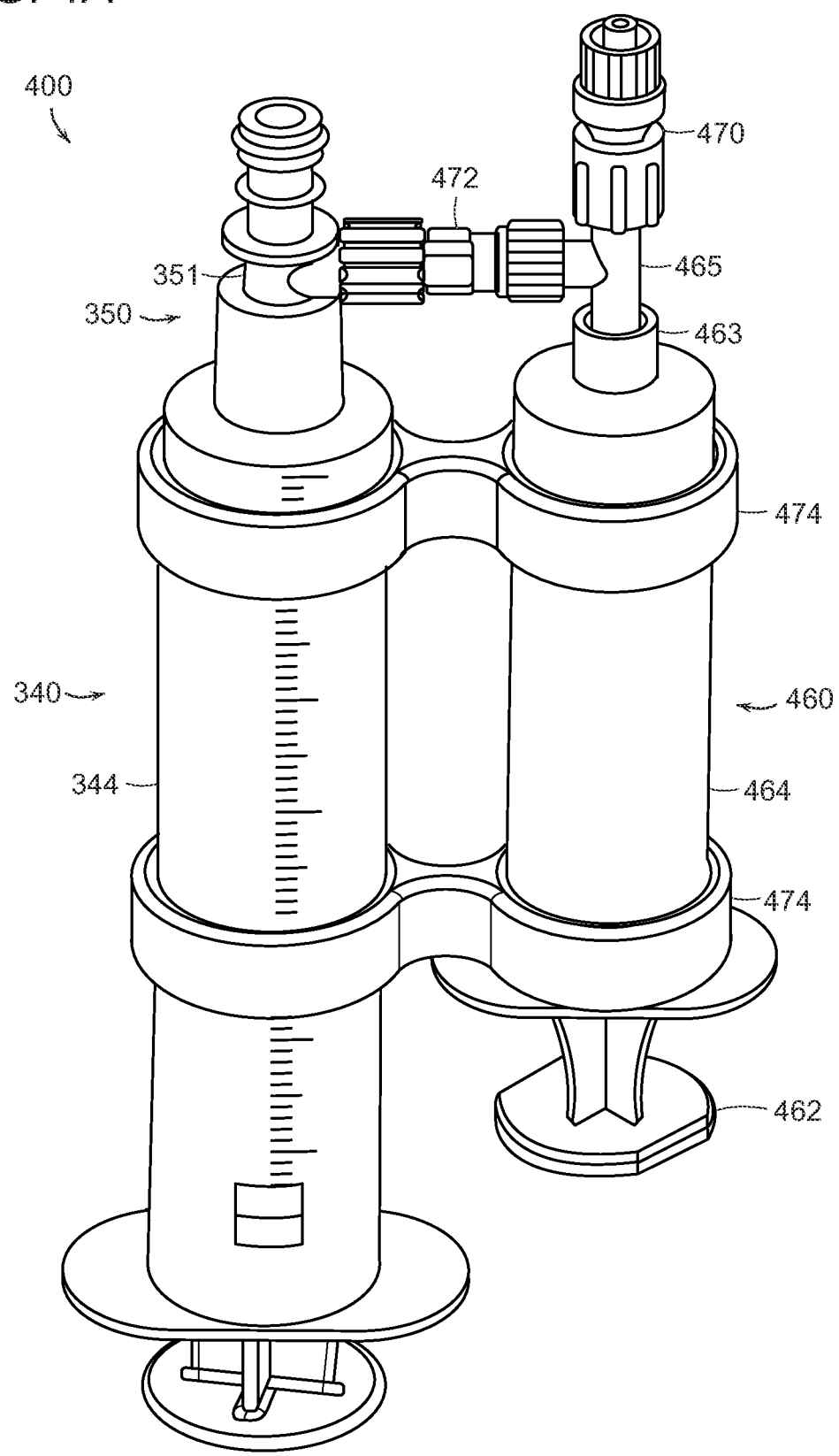
FIG. 4A is a perspective side view of another pressure source configured in accordance with the present technology.

FIG. 4A is a side perspective view a pressure source 400 including the syringe 340 ("primary syringe 340") shown in FIGS. 3A-3D and a secondary syringe 460 configured in accordance with the present technology. The secondary syringe 460 can include a plunger 462 slidably positioned within a chamber or barrel 464. The primary and secondary syringes 340, 460 can have the same volume or different volumes. In the illustrated embodiment, a tip 463 of the secondary syringe 460 is coupled to a first one-way valve (e.g., a check valve) 470 via a coupling member 465, such as a tube. The first one-way valve 470 is configured to fluidly connect the secondary syringe 460 to the ambient environment or another device coupled to the first one-way valve 470. A second one-way valve (e.g., a check valve) 472 spans between and is configured to fluidly connect the primary syringe 340 to the secondary syringe 460. More specially, in the illustrated embodiment the second one-way valve 472 is connected between the first portion 351 of the adaptor 350 and the coupling member 465. In other embodiments, the second one-way valve 472 can couple the primary and secondary syringes 340, 460 in different manners. For example, the second one-way valve 472 can span between and directly connect the barrels 344, 464. The primary and secondary syringes 340, 460 can be coupled or fastened together via one or more connectors 474 that fix the positions of the barrel 344, 464 relative to one another.

In some embodiments, the second one-way valve 472 is a normally-open check valve configured to (i) permit fluid (e.g., air) flow from the primary syringe 340 and the adaptor 350 to the secondary syringe 460 and (ii) inhibit fluid flow in the opposite direction from the secondary syringe 460 into the primary syringe 340. In some embodiments, the second one-way valve 472 has a cracking (e.g., opening) pressure of about 0 psi. In one aspect of the present technology, this arrangement maximizes the magnitude of the vacuum that can be charged within the primary syringe 340. That is, the cracking pressure of the second one-way valve 472 does not reduce the effective vacuum within the primary syringe 340. In other embodiments a normally-closed or other type of valve could be used for the second one-way valve 472. However, in such embodiments the vacuum efficiency of the pressure source 400 would be reduced by the cracking pressure of the second one-way valve 472. Similarly, the first one-way valve 470 can be a check valve configured to (i) permit fluid flow from the secondary syringe 460 to the ambient environment (or other device) and (ii) inhibit fluid flow in the opposite direction from the ambient environment into the secondary syringe 460.

Figure 4B:
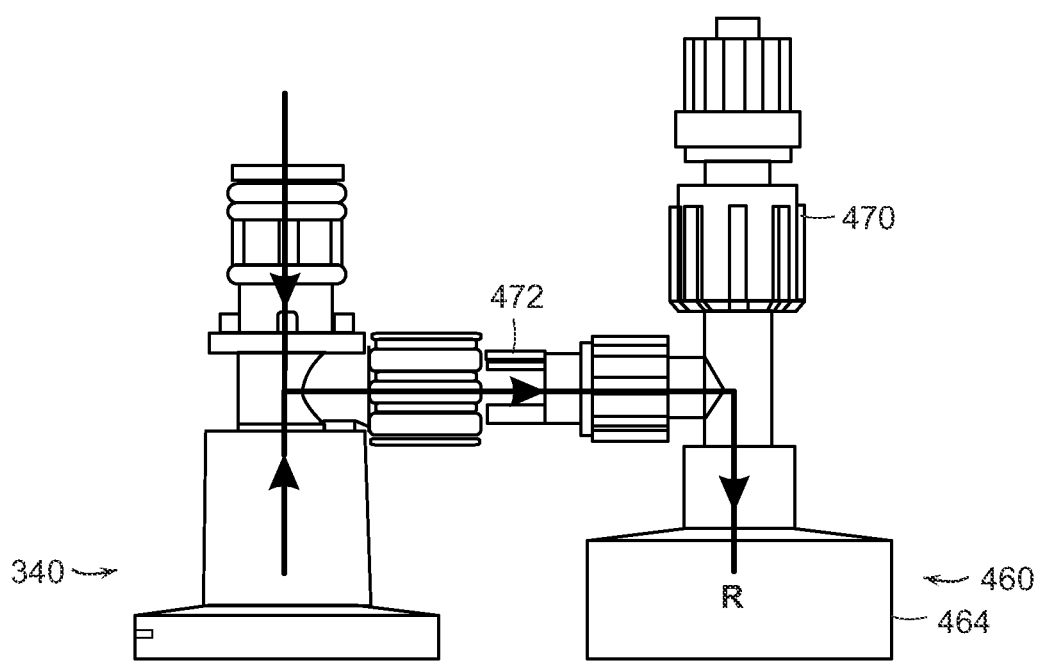
FIGS. 4B and 4C are enlarged schematic side views of the pressure source of FIG. 4A during operation.
Figure 4C:
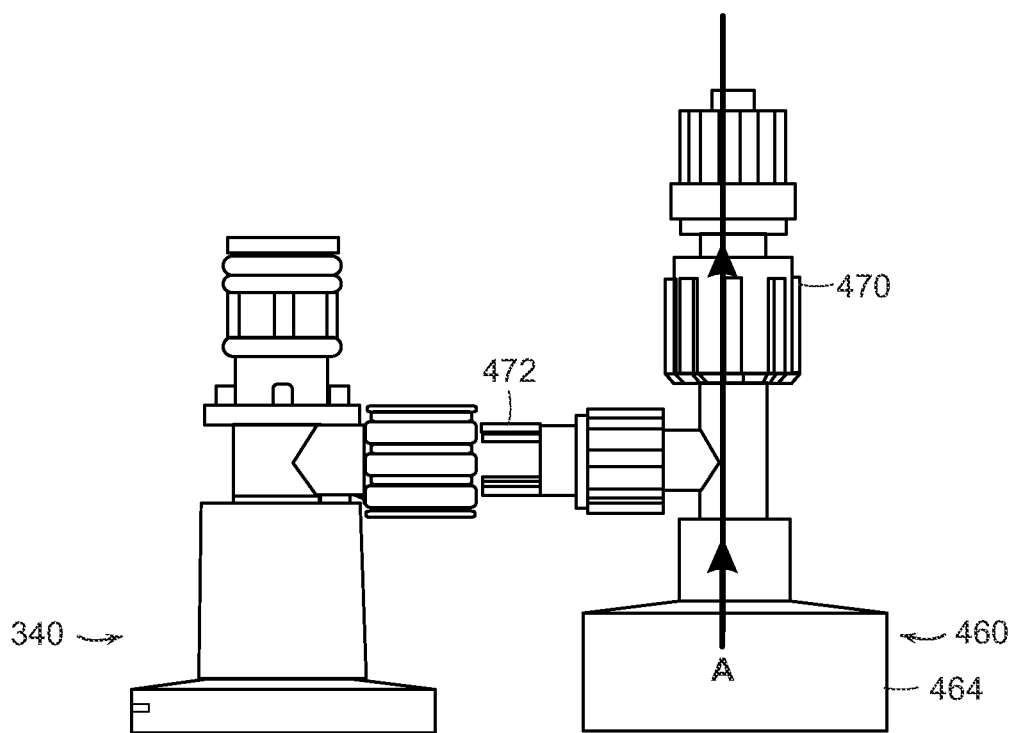

FIGS. 4B and 4C are enlarged schematic side views of the pressure source 400 during operation. More specifically, FIGS. 4B and 4C illustrate fluid flow paths through the first and second one-way valves 470, 472 during retraction and advancement, respectively, of the plunger 462 through the barrel 464 of the secondary syringe 460. Referring first to FIGS. 4A and 4B together, during retraction/withdrawal of the plunger 462, (i) the first one-way valve 470 is closed to inhibit fluid from flowing into the secondary syringe 460 while (ii) the second one-way valve is open 472 to permit fluid to flow from the primary syringe 340, the catheter subsystem 100 (FIG. 1), and/or the tubing subsystem 120 (FIG. 1) into the secondary syringe 460. This flow path is indicated by the arrows R in FIG. 4B. Referring to FIGS. 4A and 4C together, during advancement of the plunger 462, (i) the first one-way valve 470 is open to permit fluid flow (e.g., fluid expulsion) from the secondary syringe 460 to the ambient environment (or other device) while (ii) the second one-way valve 472 is closed to inhibit fluid flow from the secondary syringe 460 into (e.g., back into) the primary syringe 360, the catheter subsystem 100, and/or the tubing subsystem 120. This flow path is indicated by the arrows A in FIG. 4C.

Referring to FIGS. 1 and 3A-4C together, the pressure source 400 can be coupled to the tubing subsystem 120 by coupling the primary syringe 340 to the connector 128 (e.g., as shown in FIG. 3D). When the pressure source is coupled to the tubing subsystem 120, retraction of the plunger 462 of the secondary syringe 460 evacuates an evacuatable volume of the assembly 10. For example, when the fluid control device 126 is closed, retraction of the plunger 462 of the secondary syringe 460 evacuates fluid, through the second one-way valve 472, from (i) the primary syringe 340 (e.g., from the barrel 344, the tip 347, and/or the adaptor 350) and (ii) the portion of the tubing subsystem 120 between the fluid control device 126 and the primary syringe 340. This can enable a greater charged/stored vacuum to be generated for subsequent application to the catheter subsystem 100 for aspirating clot material. In some embodiments, the plunger 462 of the secondary syringe 460 can be withdrawn/advanced (e.g., "cycled") one or more times before withdrawing the plunger 342 of the primary syringe 340 to evacuate air from (i) the tip 347 of the primary syringe 340 and/or (ii) the portion of the tubing subsystem 120 between the fluid control device 126 and the tip 347. In other embodiments, the plunger 462 of the secondary syringe 460 can alternatively or additionally be withdrawn after withdrawing the plunger 342 of the primary syringe 340 to further evacuate the barrel 344 of the primary syringe 340. In some embodiments, the plunger 462 can be cycled when the fluid control device 126 is open to, for example, facilitate the removal of clot material stuck or clogged within the catheter subsystem 100. That is, cycling the secondary syringe 460 when the fluid control device 126 is open can generate vacuum pressure and suction in the catheter 102 to aid in the aspiration/removal of clot material.

In some embodiments, the volumes of the primary and secondary syringes 340, 460 can be selected based on one or more desired characteristics of a clot removal procedure using the pressure source 400. For example, the secondary syringe 460 can have a larger volume than the primary syringe 340 to permit a high vacuum to be charged within the primary syringe 340 while also limiting blood loss from the patient.

In one aspect of the present technology, the pressure source 340 permits a greater vacuum to be generated without increasing the volume of the primary syringe 340. For example, the vacuum generated by the primary syringe 340 alone is directly proportional to the volume of the primary syringe 340. Thus, to generate a greater vacuum using the primary syringe 340 alone, the volume of the primary syringe 340 must be increased. In contrast, inclusion of the secondary syringe 460 in the pressure source 400 and the configuration of the first and second one-way valves 470, 472 allows the (e.g., maximum) generated vacuum to be independent of the volume of the primary syringe 340. Therefore, for example, the generated vacuum can be increased without correspondingly increasing the volume of blood withdrawn from the patient when applying the vacuum to the catheter subsystem 100.

In some embodiments, (e.g., as described in greater detail below with reference to FIG. 19), the primary syringe 340 of the pressure source 400 can be replaced with a simple pressure vessel or other volume, such as a canister, barrel, tube, etc. In such embodiments, a vacuum can be generated in the canister simply by cycling the secondary syringe 460 one or more times. In some embodiments, the secondary syringe 460 can comprise a pump or vacuum source other than a syringe. Likewise, the secondary syringe 460 or other vacuum source can be fluidly coupled to the primary syringe 340 in other manners (e.g., via a different arrangement of check valves) to produce the same or similar flow patterns as shown in FIGS. 4B and 4C. Moreover, in some embodiments the first and second one-way valves 470, 472 can be other types of flow control devices that are mechanically activated/deactivated (e.g., opened and closed) rather than passively operated via pressure differentials within the pressure source 400. For example, the flow control devices 470, 472 can be mechanically coupled to the plunger 462 of the secondary syringe 460 such that cycling the plunger 462 activates/deactivates the flow control devices 470, 472 to operate the pressure source 400 in the manner illustrated in FIGS. 4B and 4C.

Figure 5:
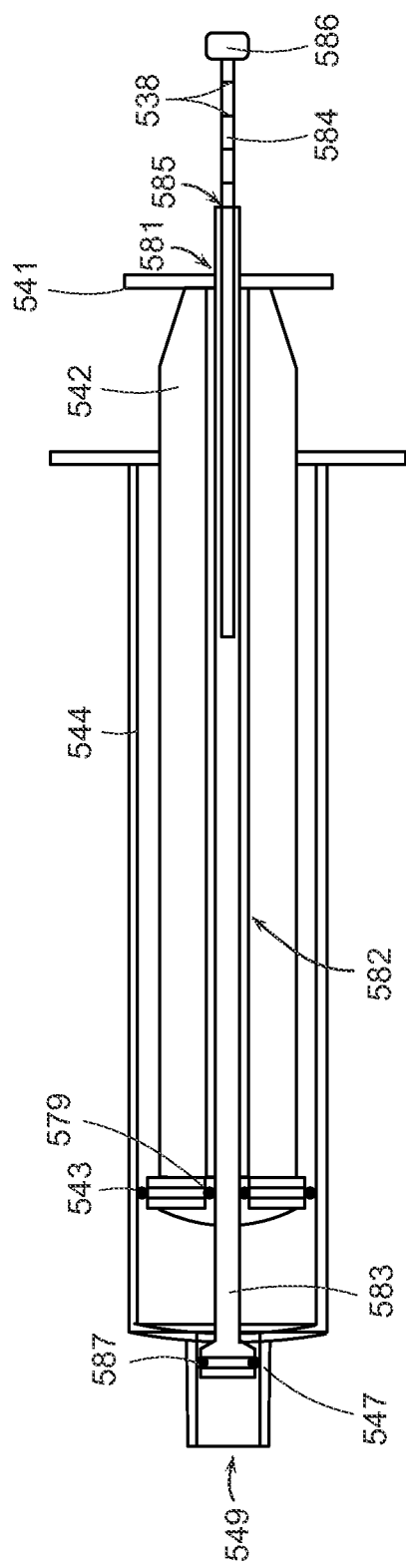
FIG. 5 is a cross-sectional side view of an automatic release syringe configured in accordance with the present technology.

FIG. 5 is a side cross-sectional view of a pressure source 540 comprising an automatic release syringe ("syringe 540") configured in accordance with the present technology. In general, the syringe 540 is configured to automatically apply a charged vacuum of a selected volume to the catheter subsystem 100 without requiring the actuation of an intervening fluid control device, such as the fluid control device 126 shown in FIG. 1. The syringe 540 can have some features generally similar to the features of the syringes 240, 340 described in detail above with reference to FIGS. 2 and 3A-3D. For example, the syringe 540 includes a first plunger 542 slidably positioned within a chamber or barrel 544. The first plunger 542 further includes a first seal 543 that engages an interior surface of the barrel 544 such that a vacuum is formed within the barrel 544 as the first plunger 542 is withdrawn through the barrel 544. Likewise, referring to both FIGS. 1 and 5 together, the syringe 540 includes a tip 547 (e.g., a Toomey tip) for coupling the syringe 540 to the tubing subsystem 120 (e.g., via a Toomey tip adaptor) and defining a bore 549. In some embodiments, the bore 549 has a relatively large diameter selected to provide rapid pressure equalization in the assembly 10 after a vacuum stored in the syringe 540 is released.

The first plunger 542 can further include (i) a grip portion 541 configured to be engaged by a user for retracting the first plunger 542 and (ii) a lumen 581 extending lengthwise therethrough. In the illustrated embodiment, a plunger assembly 582 is slidably positioned within and extends through the lumen 581 of the first plunger 542. The plunger assembly 582 includes (i) a second plunger 583 and (ii) a release member 584 slidably and/or rotatably positioned within a lumen 585 of the second plunger 583. The release member 584 includes an engagement member 586 configured to engage the grip portion 541 of the first plunger 542 when the first plunger 542 is withdrawn from the barrel 544. The second plunger 583 includes a second seal 587 configured to engage and seal an interior surface of the bore 549 of the syringe 540 to enable a vacuum to be formed in the barrel 544 as the first plunger 542 is withdrawn through the barrel 544. That is, the second seal 587 can seal (e.g., fluidly disconnect) the barrel 544 of the syringe from the tubing subsystem 120 and the catheter subsystem 100. In some embodiments, the syringe 540 can further include an O-ring 579 or other suitable component for sealing an interface between the first and second plungers 542, 582 to maintain the vacuum formed within the barrel 544, while also permitting the first plunger 542 to move (e.g., translate) relative to the second plunger 583.

The plunger assembly 582 further includes a locking mechanism (not shown) configured to permit/inhibit the release member 584 from moving longitudinally relative to the second plunger 583. In some embodiments, for example, rotation of the release member 584 in a first direction relative to the second plunger 583 can lock the two components in position, while rotation of the release member 584 in a second direction relative to the second plunger 583 can unlock the two components so that the release member 584 can be withdrawn or pushed into the lumen 585 of the second plunger 583. In other embodiments, the release member 584 and the second plunger 583 can be integrally formed or permanently locked together.

The plunger assembly 582 enables (i) a user of the syringe 540 to select a desired volume for a vacuum to be formed in the syringe 540 and (ii) the automatic release or application of a generated vacuum via opening (e.g., unplugging) of the bore 549. Specifically, during operation of the syringe 540, a user can first unlock the release member 584 and slide the release member 584 to a position corresponding to a desired vacuum volume. For example, the release member 584 can have tick marks 588 or other indicia along its length that correspond to a volume of the syringe 540 (e.g., a vacuum chamber volume). After selecting a desired volume, the user can lock the release member 584 relative to the second plunger 583 (e.g., by rotating the release member 584) to inhibit relative movement of the two components. After locking the release member 584, the user can grasp the grip portion 541 to retract the first plunger 542 relative to the barrel 544 and the plunger assembly 582 to generate a vacuum within the barrel 544 between the first and second seals 543, 587. When the first plunger 542 has been retracted to the desired volume, the grip portion 541 engages the engagement member 586 of the release member 584 such that further retraction of the first plunger 542 simultaneously retracts the plunger assembly 582. As the plunger assembly 582 is retracted, the second seal 587 of the second plunger 583 is pulled out of the bore 549, thereby releasing the vacuum stored in the barrel 544. In this manner, the syringe 540 provides for the automatic release of charged vacuum pressure at a specified volume and with a single retraction of the first plunger 542. Put differently, the syringe 540 has a built-in fluid control device and thus eliminates the need for a separate fluid control device 126 and/or an additional step for opening the fluid control device 126.

Figure 6:
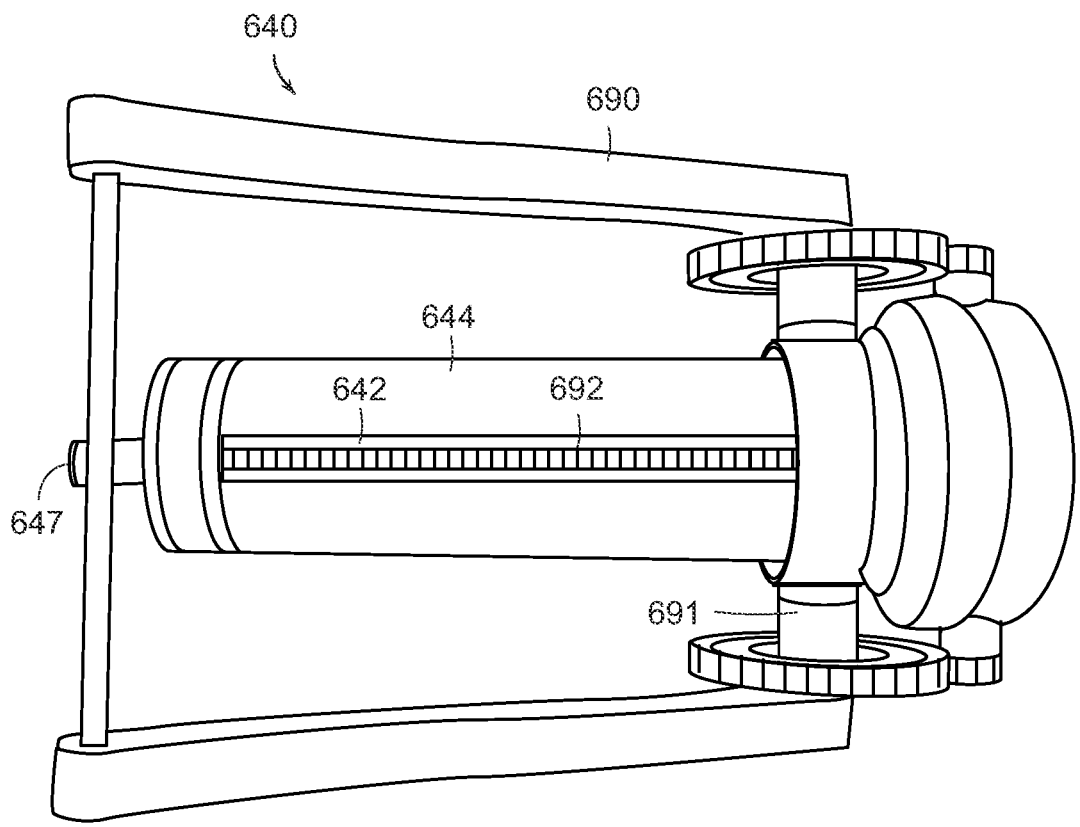
FIG. 6 is a perspective top view of a syringe configured in accordance with the present technology.

FIG. 6 is a top perspective view of a pressure source 640 comprising a syringe ("syringe 640") configured in accordance with the present technology. The syringe 640 can include some features generally similar to the features of the syringes 240, 340, and 540 described in detail above with reference to FIGS. 2-3D and 5. For example, the syringe 640 includes a plunger 642 slidably positioned within a barrel 644, and a tip 647 (e.g., a large-bore tip). In the illustrated embodiment, the syringe 640 further includes a lever or handle 690 operably coupled to the plunger 642. The handle 690 provides mechanical leverage for withdrawing the plunger 642 to create a vacuum within the barrel 644. More specifically, the handle 690 can be coupled to a crossbar 691 that rotates relative to the plunger 642 via actuation (e.g., rotation) of the handle 690. The crossbar 691 can be coupled to a gear (obscured in FIG. 6) configured to engage a track 692 on the plunger 642. Accordingly, rotation of the handle 690 in a first direction retracts the plunger 642 relative to the barrel 644 to charge a vacuum in the barrel 644. And, rotation of the handle 690 in a second (e.g., opposite) direction advances the plunger 642 into the barrel 644 to, for example, expel fluid, material, etc., from the barrel 644.

In one aspect of the present technology, the handle 690 provides additional mechanical leverage relative to a standard syringe, and can thus reduce the force (e.g., strain, energy, etc.) required by a user of the syringe 640 to form a vacuum in the syringe 640. Therefore, use of the syringe 640 can reduce the time needed to remove clot material with the assembly 10. In some embodiments, the syringe 640 can have a volume greater than 60 cc (e.g., greater than 80 cc, greater than 100 cc, greater than 120 cc, greater than 140 cc, etc.). In a particular embodiment, for example, the syringe 640 can have a volume of about 140 cc. With such large volumes, it may be difficult for some users to manually retract the plunger 642 without the additional mechanical leverage provided by the handle 690. Thus, the syringe 640 can enable the use of larger volume syringes that can generate correspondingly greater suction forces in the catheter subsystem 100.

Figure 24:
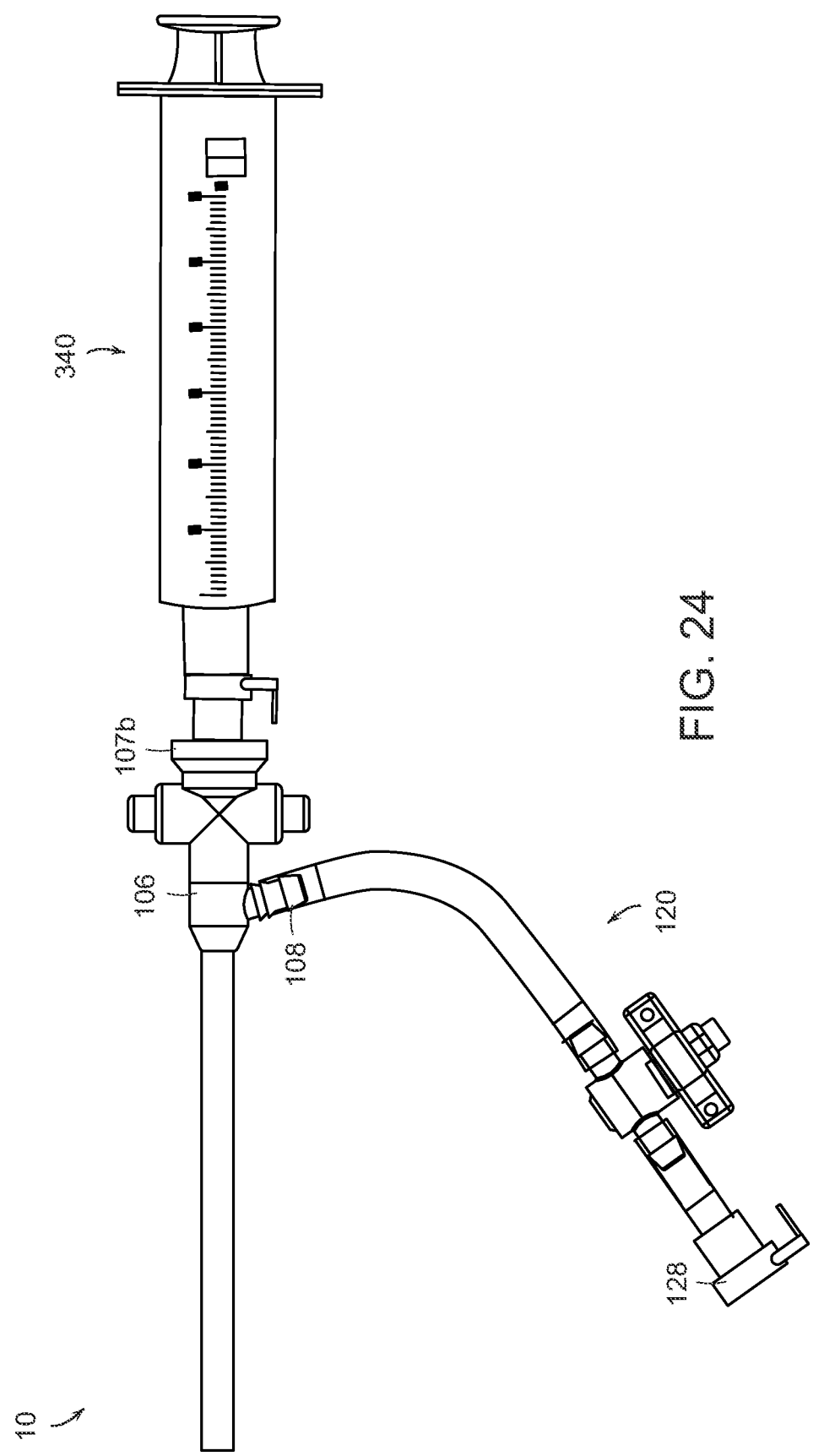
FIG. 24 is an enlarged isometric view of the clot removal system of FIG. 1 configured in accordance with the present technology.
Figure 25:
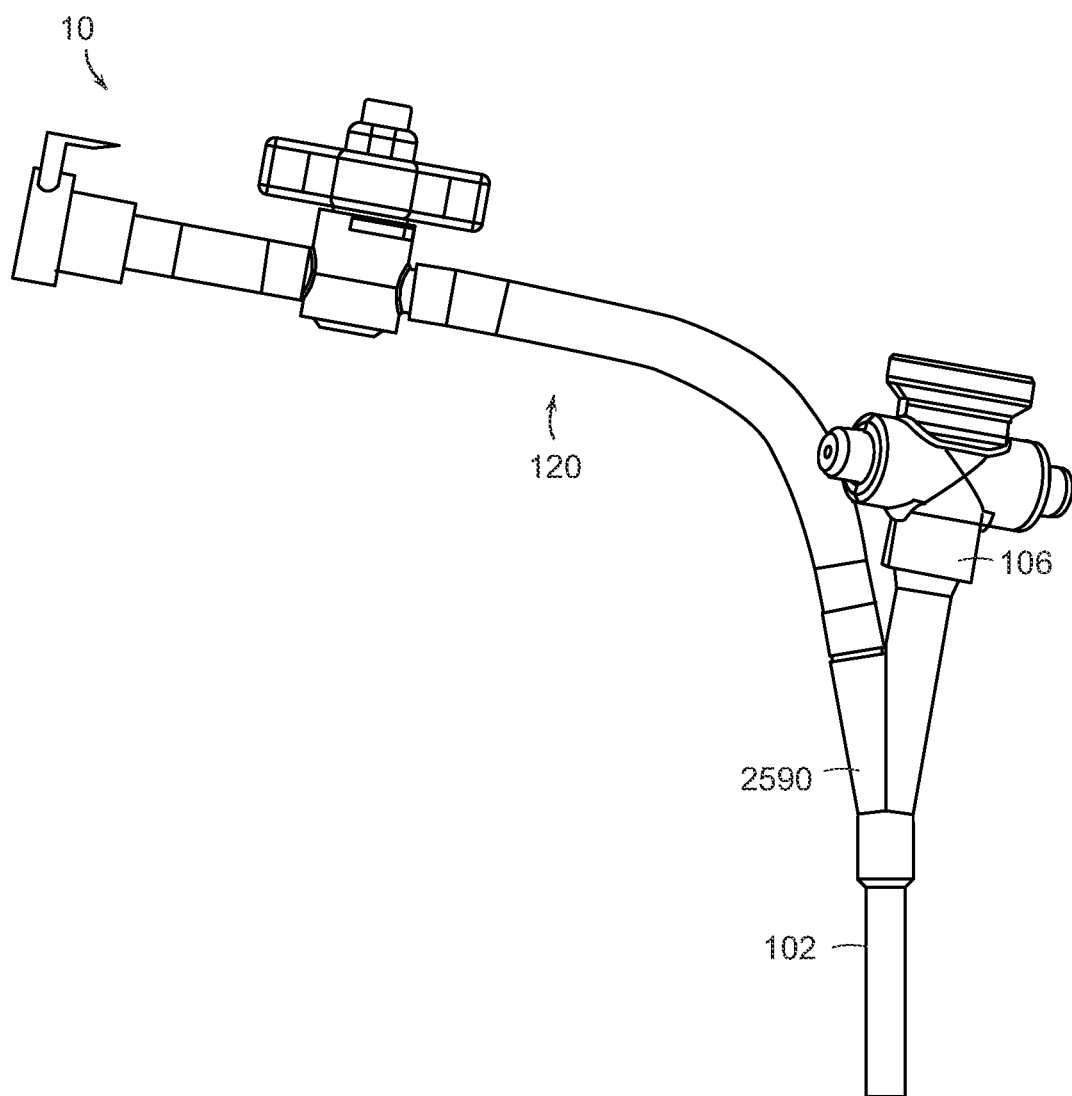
FIG. 25 is an enlarged isometric view of the clot removal system of FIG. 1 configured in accordance with the present technology.

Referring again to FIG. 1, it is expected that less tortuous (e.g., more linear) fluid paths between the pressure source 140 and the catheter subsystem 100 will produce greater suction forces and corresponding fluid velocities at the distal portion 103a of the catheter 102 when stored vacuum pressure is applied to the catheter subsystem 100. Accordingly, in some embodiments the side port 108 of the valve 106 can be formed to have an angle A that is less than about 90°, less than about 75°, less than about 60°, less than about 45°, less than about 30°, less than about 15° etc. Reducing the relative angle between the side port 108 and the lumen 109 of the valve 106 (and thus the lumen 104 of the catheter 102) reduces the tortuosity of the fluid path between the pressure source 140 and the catheter 102. Moreover, in some embodiments, the pressure source 140 can be coupled to the proximal portion 107*b* of the valve 106 instead of or in addition to the side port 108 to provide a more linear fluid path between the pressure source 140 and the catheter 102. For example, FIG. 24 is an enlarged isometric view of the assembly 10 showing the pressure source 340 coupled directly to the proximal portion 107*b* of the valve rather than to the connector 128 of the tubing subsystem 120 and the side port 108 of the valve 106. Although the pressure source 340 is illustrated in FIG. 24, any of the pressure sources described in detail above with reference to FIGS. 2-6 can be configured to be coupled to the proximal portion 107*b* of the valve 106 rather than the side port 108. In other embodiments, the side port 108 can be omitted and the valve 106 and the tubing subsystem 120 can be coupled to the catheter 102 via a Y-connector. For example, FIG. 25 is an enlarged isometric view of the assembly 10 showing the valve 106 and the tubing subsystem 120 coupled to the catheter 102 via a Y-connector 2590. In yet other embodiments, the tubing system 120 is linearly coupled to the catheter 102, and the valve 106 protrudes at an angle from the catheter 102.

Figure 7:
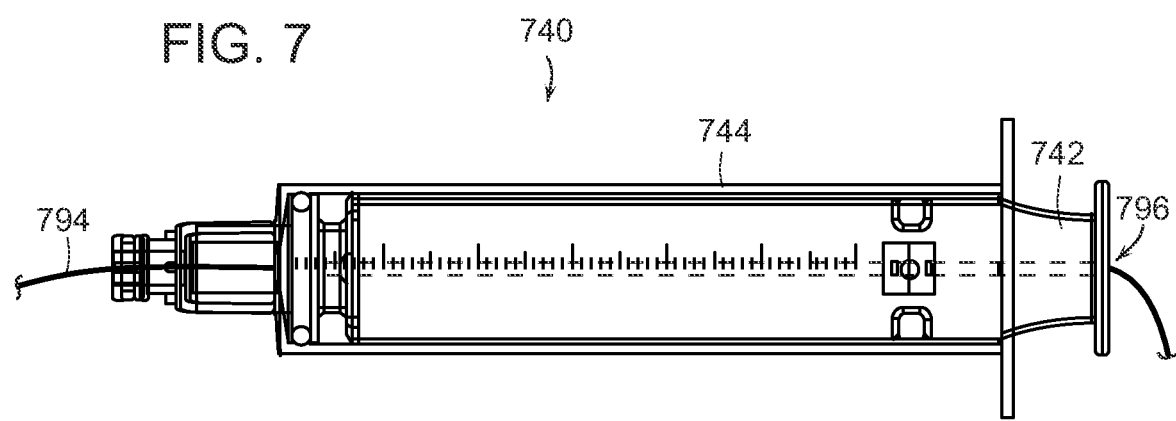
FIG. 7 is a side view of an over-wire locking syringe configured in accordance with the present technology.

In some embodiments, however, a guidewire or other component is positioned within the valve 106 during the duration of a clot removal procedure (e.g., for delivering interventional devices to a treatment site within a patient). Accordingly, in some embodiments, to facilitate coupling of the pressure source 140 to the proximal portion 107*b* of the valve 106—even when a guidewire is inserted therethrough—the pressure source 140 can be a syringe configured for over-wire delivery. For example, FIG. 7 is a side view of a pressure source 740 comprising a vacuum-pressure locking syringe ("syringe 740") configured in accordance with the present technology for delivery and operation over a guidewire 794. The syringe 740 can have some features generally similar to the features of the syringe 340 described in detail above with reference to FIG. 3. For example, the syringe 740 includes a plunger 742 slidably and rotatably positioned within a barrel 744. The barrel 744 is shown as transparent in FIG. 7 for the sake of clarity. In the illustrated embodiment, the plunger 742 includes a lumen 796 (shown in broken lines) extending longitudinally therethrough. The guidewire 794 can be inserted through the lumen 796 of the plunger 742 such that the syringe 740 can be advanced over the guidewire 794 for attachment to the proximal portion 107*b* of the valve 106. The syringe 740 can further include one or more sealing components (e.g., valves, O-rings, etc.; not shown) for maintaining a seal between the guidewire 794 and the plunger 742 to permit build-up and storage of a vacuum in the barrel 744.

In general, one skilled in the art will understand that the various embodiments of pressure sources disclosed herein may be combined to, for example, include multiple pressure sources or pressure sources having different components or combinations of components. For example, in some embodiments the secondary syringe 460 (FIGS. 4A-4C) can be coupled via one or more one-way valves to the syringes 240, 540, 640 or 740 (FIGS. 2 and 5-7, respectively) to generate additional vacuum. In some embodiments, multiple pressure sources can be coupled to the catheter 102 via the tubing subsystem 120 and/or via the valve 106. Moreover, the individual pressure sources can be the same or different, and can be coupled to the catheter subsystem 100 via a single fluid control device, such as the fluid control device 126, or can be coupled to the catheter subsystem 100 via separate fluid control devices. Therefore, the profile of the vacuum applied to the catheter 102 can be selected or adjusted by using multiple different pressure sources. For example, a specific vacuum profile can depend at least on (i) the individual characteristics of the multiple pressure sources (e.g., volume, bore-size, etc.), (ii) the manner in which the pressure sources are coupled to the catheter subsystem 100 (e.g., via individual valves, via the same valve, etc.), and (iii) the timing of the application or release of the vacuum of each pressure source to the catheter subsystem 100 (e.g., staggered release, simultaneous release, etc.). As one example, in some embodiments, the syringe 240 (FIG. 2) and the syringe 340 (FIG. 3) can both be coupled to the tubing subsystem 120 via, for example, a Y-connector. After charging both syringes 240, 340 with vacuum pressure, opening the fluid control device 126 can simultaneously apply the combined vacuum to the catheter 102. The larger-bored syringe 340 can provide a short but powerful impulse of vacuum pressure, while the smaller-bored syringe 240 can provide a longer and more sustained vacuum pull. This combination can apply a large, fast-acting suction force to dislodge and capture clot material in the catheter 102, and simultaneously apply a more sustained suction force to capture more clot material.

III. Selected Embodiments of Methods of Clot Removal

Figure 8:
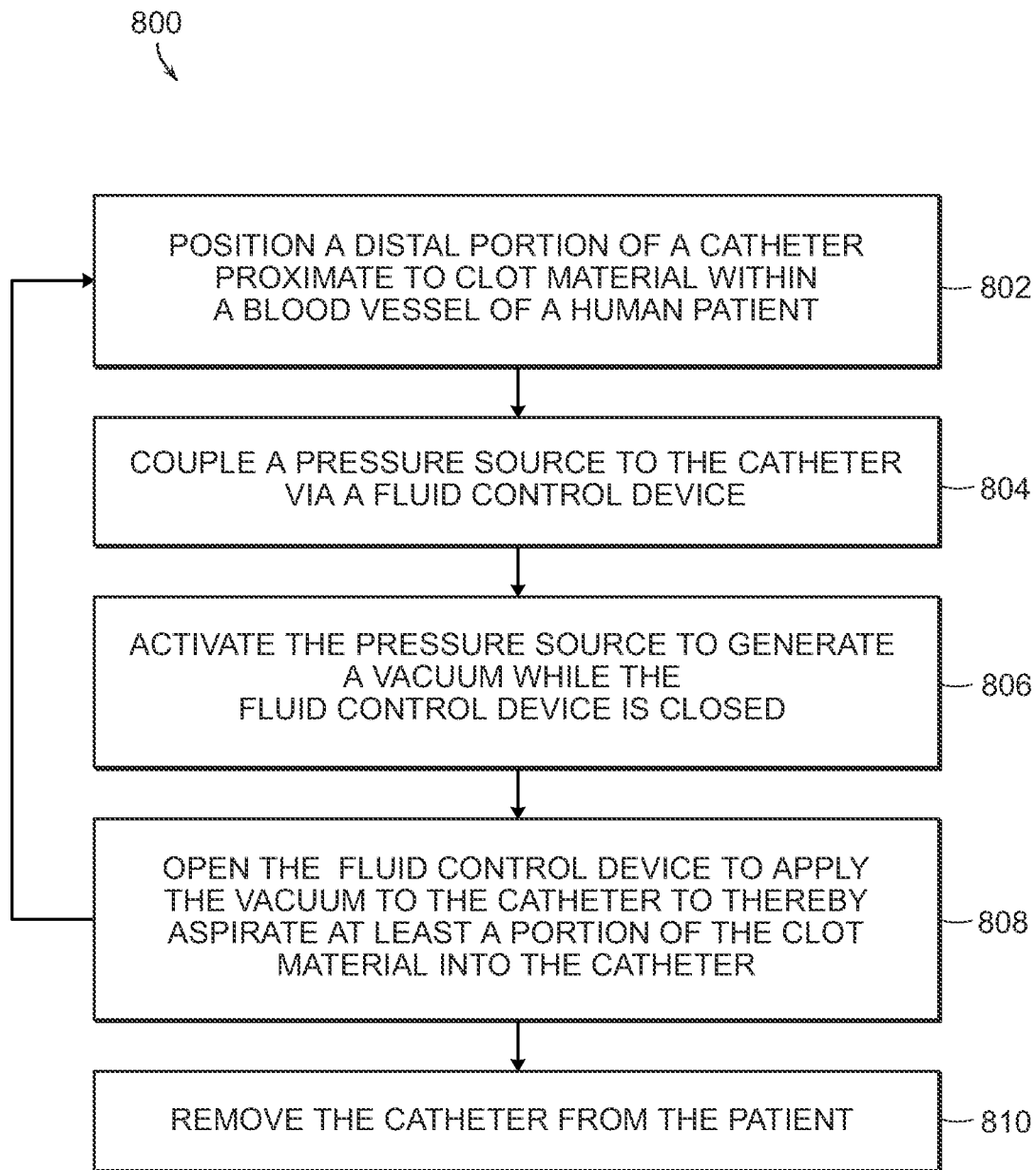
FIG. 8 is a flow diagram of a process or method for operating a clot removal system in accordance with the present technology.
Figure 9A:
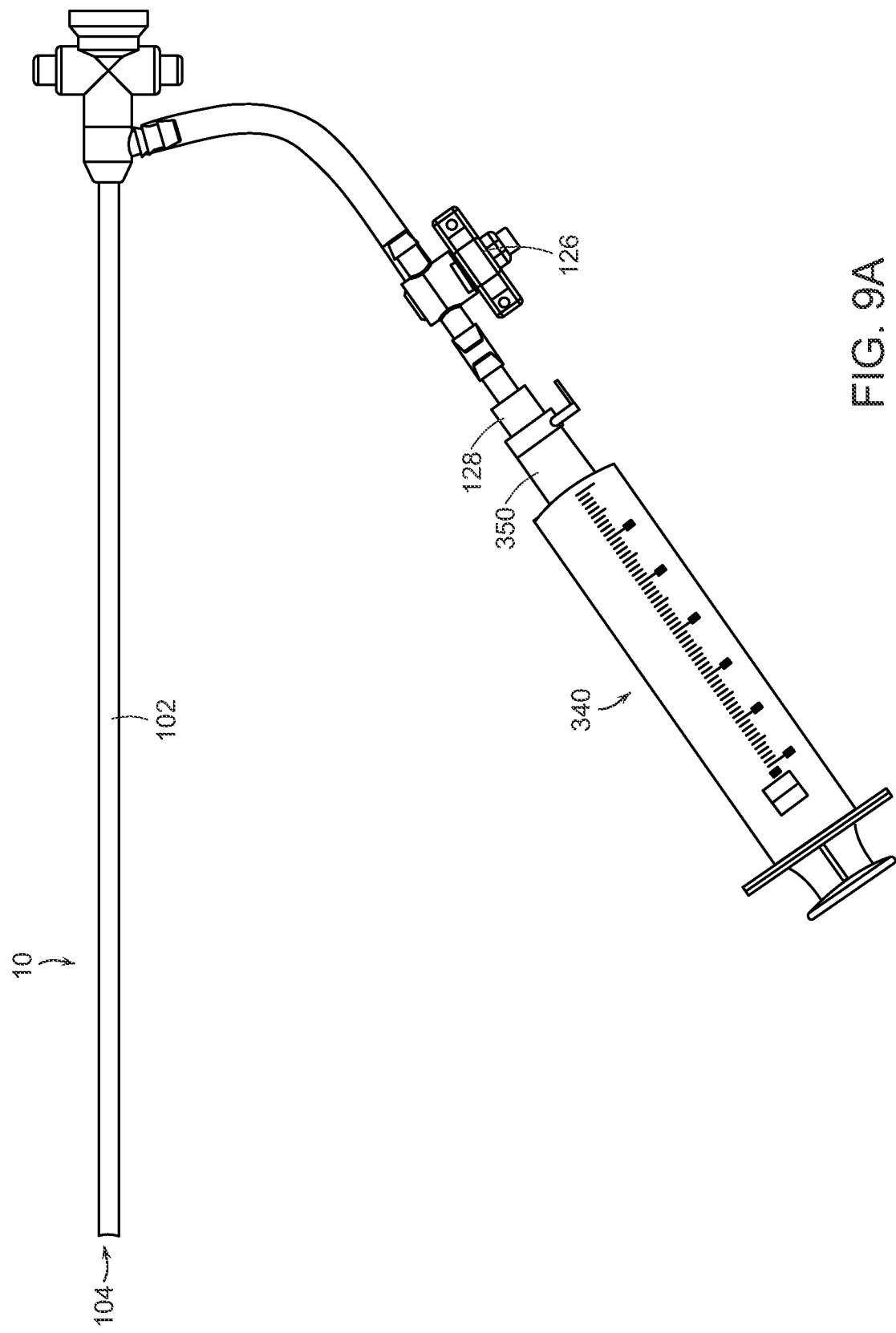
FIGS. 9A-9C are side views of a proximal portion of the clot removal system of FIG. 1 during a clot removal procedure using the locking syringe of FIG. 3 in accordance with the present technology.
Figure 9B:
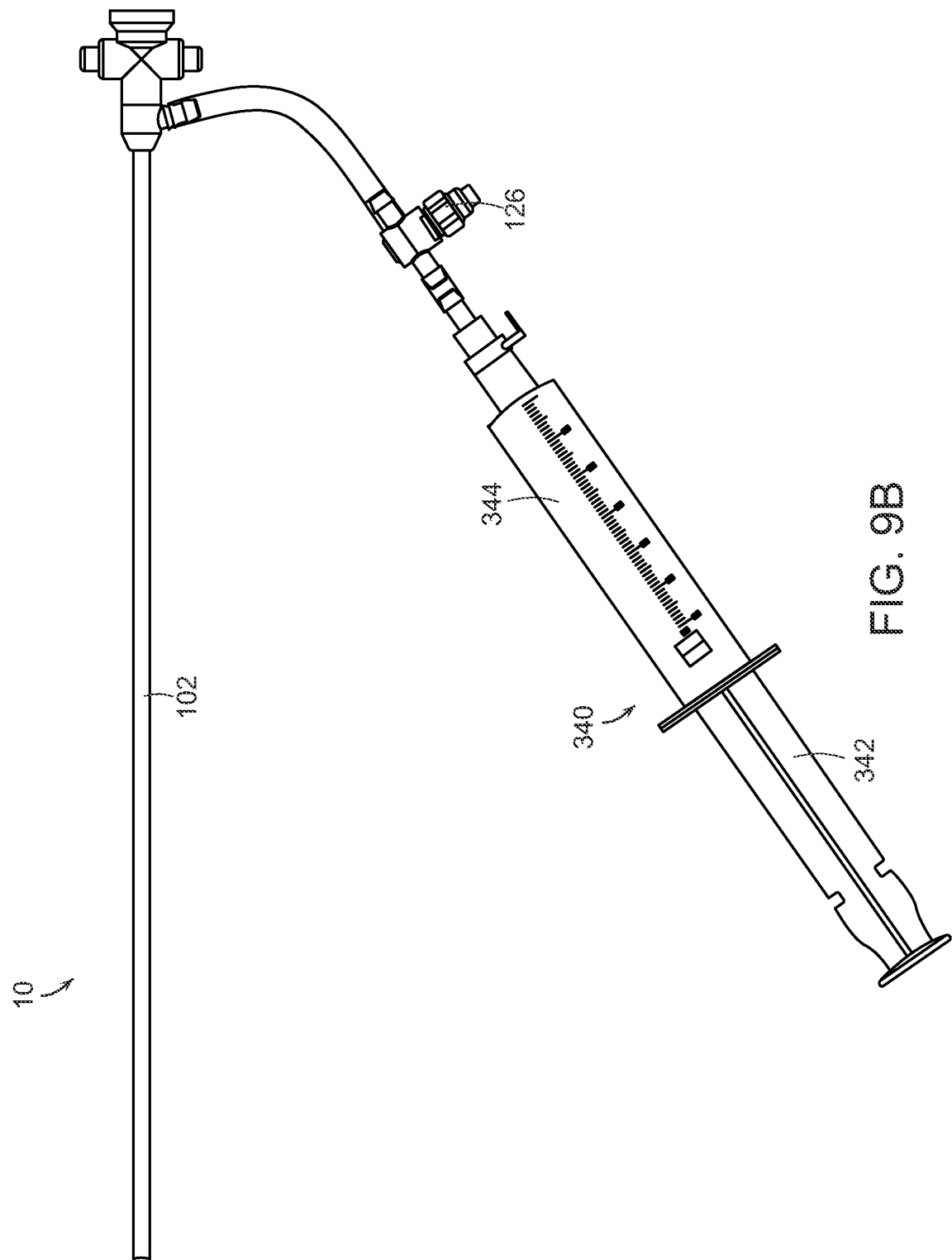
Figure 9C:
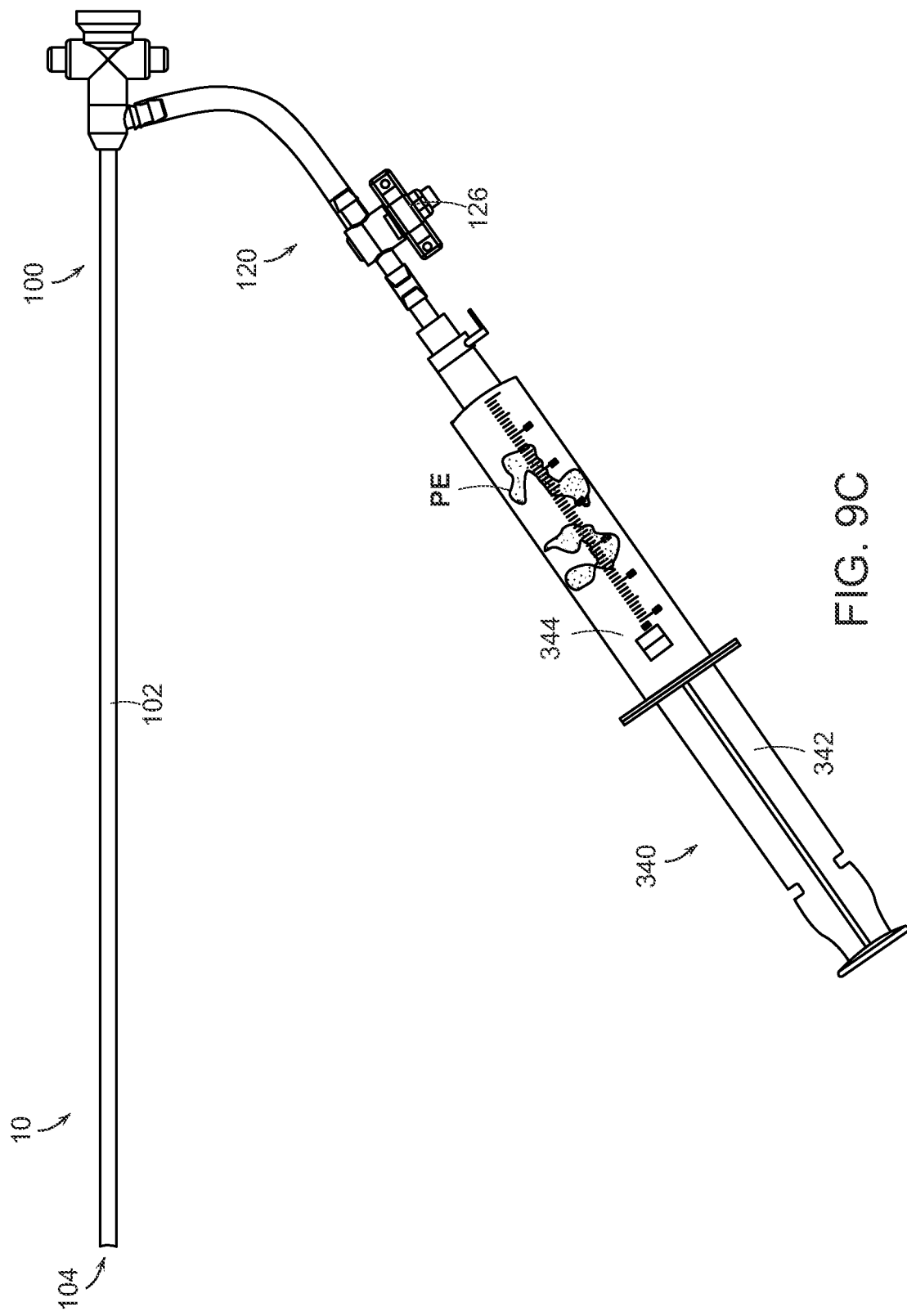
Figure 10A:
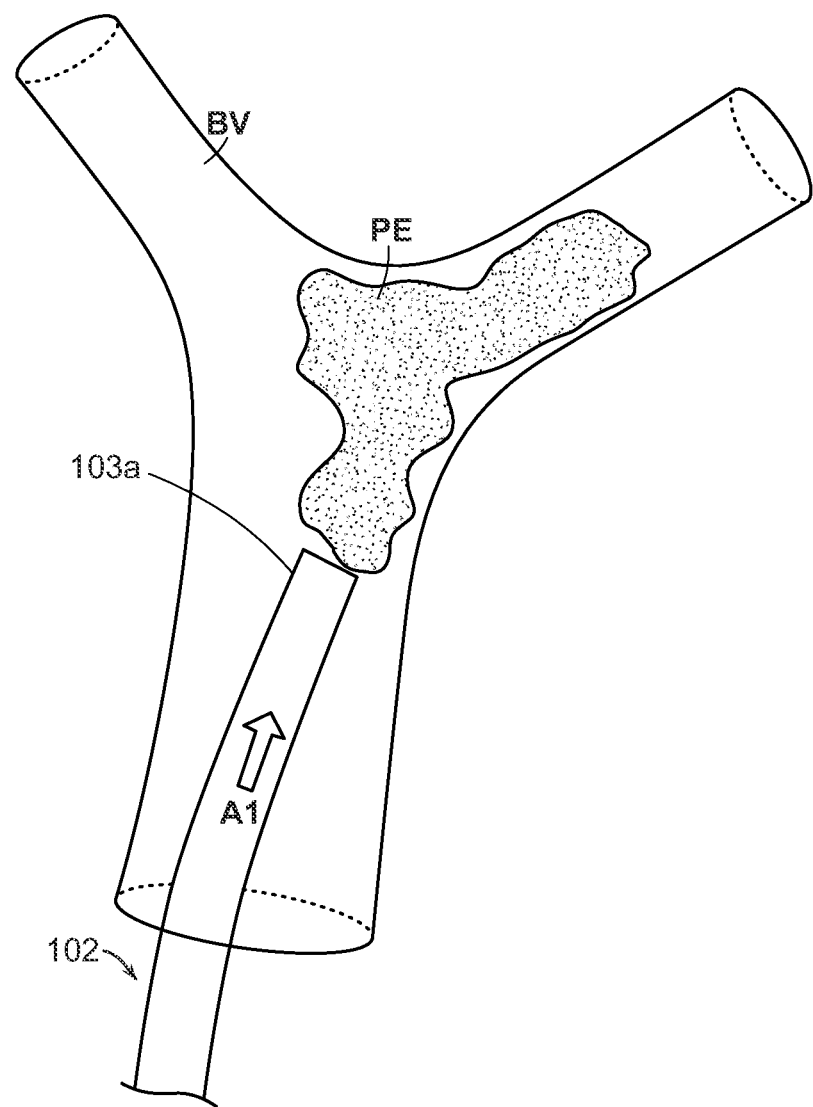
FIGS. 10A and 10B are schematic illustrations of a distal portion of the clot removal system of FIG. 1 during a clot removal procedure in accordance with the present technology.
Figure 10B:
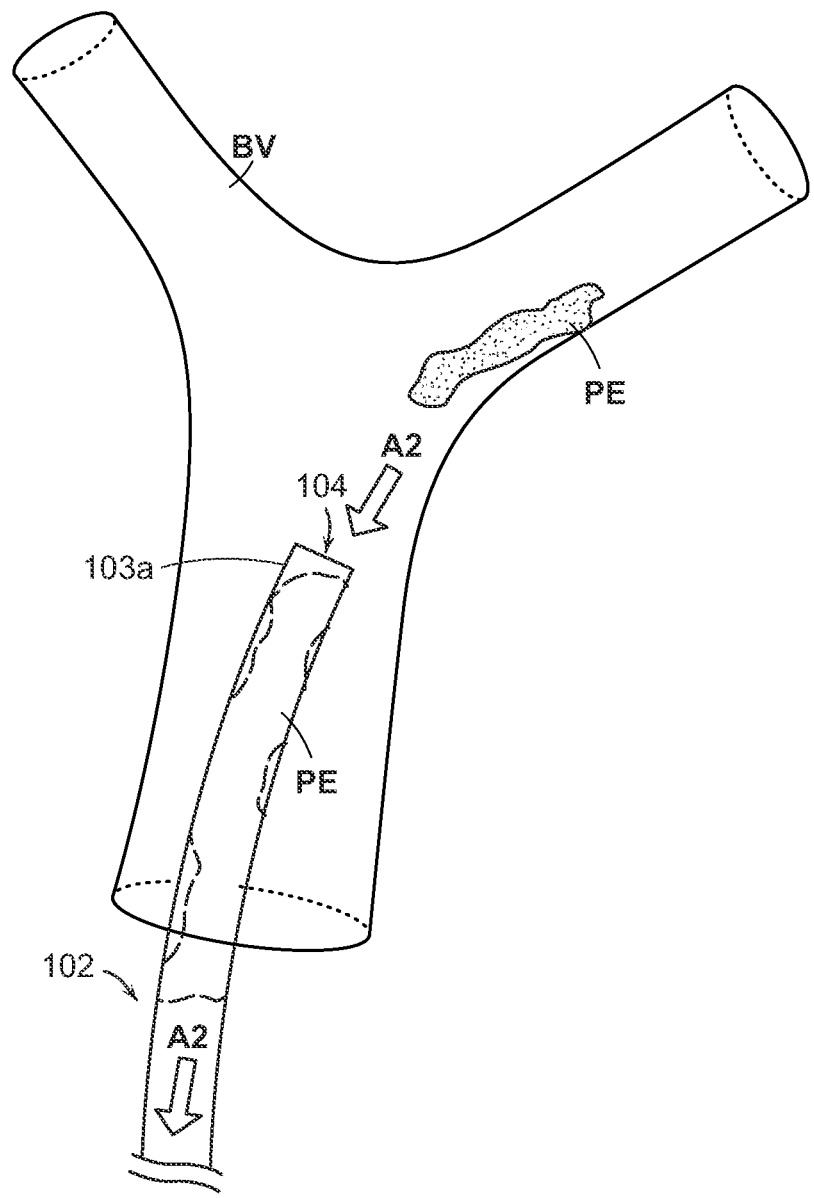

FIG. 8 is a flow diagram of a process or method 800 for operating a clot removal system including the assembly 10 to remove clot material from within a blood vessel (e.g., a pulmonary blood vessel) of a human patient in accordance with the present technology. FIGS. 9A-9C are side views of a proximal portion of the assembly 10, and FIGS. 10A and 10B are schematic illustrations of a distal portion of the assembly 10, during a clot removal procedure in accordance with embodiments of the present technology. In particular, FIGS. 9A-9C are side views of the assembly 10 including the syringe 340 and adaptor 350 (FIGS. 3A-3D), and FIGS. 10A and 10B are side views of the catheter 102 with the distal portion 103*a* of the catheter 102 positioned proximate to an embolism or clot material PE within a blood vessel BV (e.g., a pulmonary blood vessel). Although some features of the method 800 are described in the context of the embodiments shown in FIGS. 1, 3A-3D, and 9A-10B for the sake of illustration, one skilled in the art will readily understand that the method 800 can be carried out using other suitable systems and/or devices described herein. In particular, although described in the context of the syringe 340, the method 800 can be carried out using any one or combination of the pressure sources described in detail above with reference to FIGS. 2-7.

At block 802, the method 800 includes positioning the distal portion 103*a* of the catheter 102 proximate to clot material within a blood vessel of a human patient (e.g., at a treatment site). For example, in the embodiment illustrated in FIG. 10A, a distal terminus of the distal portion 103*a* of the catheter 102 is positioned proximate to a proximal portion of the clot material PE. It is expected that reducing the distance between the distal terminus of the catheter 102 and the proximal portion of the clot material PE—without contacting the clot material PE with the catheter 102—will maximize the suction forces on the clot material PE when the fluid control device 126 is opened. It is also expected that reducing the distance (e.g., clearance) between the inner diameter of the blood vessel BV and the outer diameter of the catheter will maximize the suction forces on the clot material PE. However, in other embodiments, the distal terminus of the catheter 102 can be positioned at least partially within the clot material PE, or the distal terminus of the catheter 102 can be positioned distal of the clot material PE.

Access to the pulmonary vessels can be achieved through the patient's vasculature, for example, via the femoral vein. In some embodiments, the catheter subsystem 100 can include an introducer (e.g., a Y-connector with a hemostasis valve; not shown) that can be partially inserted into the femoral vein. A guidewire (not shown) can be guided into the femoral vein through the introducer and navigated through the right atrium, the tricuspid valve, the right ventricle, the pulmonary valve, and into the main pulmonary artery. Depending on the location of the embolism, the guidewire can be guided to one or more of the branches of the right pulmonary artery and/or the left pulmonary artery. In some embodiments, the guidewire can be extended entirely or partially through the clot material PE. In other embodiments, the guidewire can be extended to a location just proximal of the clot material PE. After positioning the guidewire, the catheter 102 can be placed over the guidewire and advanced (e.g., as indicated by arrow A1) to a position proximate to the clot material PE as illustrated in FIG. 10A.

In some embodiments, to confirm the position of the distal portion 103a of the catheter 102, a contrast agent can be injected through the catheter 102 and viewed using fluoroscopic imaging techniques, as is known in the art. In some embodiments, the valve 106 can be opened to determine the position of the distal portion 103a of the catheter 102 relative to the clot material PE. For example, the activation buttons 101 can be depressed to open the lumen 109 of the valve 106. If there is substantially no back-bleeding through the valve 106, the operator can determine that the distal portion 103a of the catheter 102 is fully engaged with the clot material PE. Conversely, if there is some back-bleeding through the valve 106, the operator can determine that the distal portion 103a of the catheter is not fully engaged with the clot material PE. Accordingly, to locate the distal portion 103a of the catheter 102 just proximal of the clot material PE, the operator can (i) first determine that distal portion 103a of the catheter is fully engaged with the clot material PE by activating the valve 106 and detecting no back-bleeding and (ii) then reposition the catheter 102 (e.g., by withdrawing the catheter 102 proximally) and activate the valve 106 until back-bleeding is detected—thereby confirming that the distal portion 103a of the catheter 102 is positioned proximal of the clot material PE. In some embodiments, the valve 106 can be opened during retraction of the catheter 102 until back-bleeding is detected. In other embodiments, the valve 106 can be closed during retraction of the catheter 102, and the catheter 106 can be retracted a set (e.g., predetermined) distance before the valve 106 is opened again. In one aspect of the present technology, determining the position of the distal portion 103a of the catheter 102 via activation of the valve 106 can be used when it is difficult to determine the position of the catheter 102 via radiographic techniques. In contrast, many conventional hemostasis valves cannot be activated in this manner.

In some embodiments, the guidewire can then be withdrawn while, in other embodiments, the guidewire can remain and can be used to guide other catheters (e.g., delivery catheters, additional aspiration catheters, etc.), interventional devices, etc., to the treatment site. It will be understood, however, that other access locations into the venous circulatory system of a patient are possible and consistent with the present technology. For example, the user can gain access through the jugular vein, the subclavian vein, the brachial vein, or any other vein that connects or eventually leads to the superior vena cava. Use of other vessels that are closer to the right atrium of the patient's heart can also be advantageous as it reduces the length of the instruments needed to reach the pulmonary embolism.

At block 804, the method 800 includes coupling a pressure source (e.g., the syringe 340) to the catheter 102 via the fluid control device 126. For example, in the embodiment illustrated in FIG. 9A, the tip 347 (shown in FIGS. 3A and 3C but obscured in FIG. 9A) of the syringe 340 can be coupled to the connector 128 via the adaptor 350. Once the syringe 340 is coupled to the catheter 102, (i) opening the fluid control device 126 fluidly connects the syringe 340 to the lumen 104 of the catheter 102, and (ii) closing the fluid control device 126 fluidly disconnects the syringe 340 from the lumen 104 of the catheter 102. The fluid control device 126 is in an open position in FIG. 9A.

At block 806, the method 800 includes activating the syringe 340 to generate a vacuum while the fluid control device 126 is closed. For example, as shown in FIG. 9B, the user can first actuate the fluid control device 126 to close the fluid control device 126, and then retract the plunger 342 to generate a vacuum in the barrel 344 of the syringe 340. The user can subsequently lock the plunger 342 relative to the barrel 344, as described in detail above, to store or maintain a vacuum of known volume in the syringe 340. In this manner, the syringe 340 can be pre-charged with a vacuum before the vacuum is applied to the catheter 102. In contrast, many conventional aspiration techniques include activating a negative pressure source (e.g., a pump, a syringe, etc.) while the pressure source is fluidly connected to a lumen to be aspirated. In some embodiments, when the pressure source 400 with the secondary syringe 460 (FIGS. 4A-4C) is used with the primary syringe 340, the secondary syringe 460 can be cycled one or more times before or after retracting the plunger 342 to increase the vacuum pressure.

At block 808, the method 800 includes opening the fluid control device 126 to apply the vacuum to the lumen 104 of the catheter 102. For example, with reference to FIG. 9C, the user can actuate (e.g., twist a handle of) the fluid control device 126 to open the fluid control device 126 and apply the vacuum stored in the syringe 340 to the catheter subsystem 100. As shown in FIG. 10B, application of the vacuum causes suction at the distal tip 103a of the catheter 102 (e.g., as indicated by arrow A2) that aspirates at least a portion of the clot material PE from the blood vessel BV and into the lumen 104 of the catheter 102. In some embodiments, opening the fluid control device 126 instantaneously or nearly instantaneously generates suction at the distal portion 103a of the catheter 102. In certain embodiments, application of the vacuum can generate suction for less than about 1 second (e.g., about 0.5 second), substantially less than about 1 second (e.g., about 0.3 second, about 0.1 second, etc.) less than about 2 seconds, or greater than about 2 seconds—until the pressure in the assembly 10 equalizes. In some embodiments, depending on the volume of the vacuum chamber formed in the syringe 340 and the dimensions of the catheter subsystem 100 and the tubing subsystem 120 (e.g., where the syringe 340 has a volume that is greater than or about equal to a volume of the catheter subsystem 100), at least some of the clot material PE can be aspirated entirely through the lumen 104 of the catheter 102 and into the barrel 344 of the syringe 340. In some such embodiments, the user can determine whether subsequent steps for treating the clot material PE are necessary or desirable by visualizing the amount of clot material collected in the syringe 340. FIG. 9C, for example, illustrates the syringe 340 and the tubing subsystem 120 after the fluid control device 126 has been opened to apply the vacuum stored in the syringe 340 to the catheter 102. In the illustrated embodiment, some of the clot material PE is visible in the syringe 340.

In some embodiments, the fluid control device 126 or another fluid control device can be intermittently operated to provide discrete bursts of suction. For example, the fluid control device 126 can be quickly opened and closed to provide a first burst of suction (e.g., vacuum release) without fully equalizing the pressure in the assembly 10. The fluid control device 126 can then be opened again to provide a second burst of suction, or opened and closed repeatedly to provide a desired suction pattern. In some embodiments, the assembly 10 can be specifically configured to facilitate the application of multiple bursts of suction. For example, (i) the fluid control device 126 can be spring-loaded, electronically controlled, etc., to rapidly open and close the valve, and/or (ii) the pressure source 140 can have a large vacuum chamber and/or small bore size to increase the time required for pressure in the assembly 10 to equalize (e.g., to increase a discharge time of the pressure source 140).

Sometimes, as shown in FIG. 10B, discharging the vacuum stored in the pressure source to aspirate the lumen 104 of the catheter 102 may not remove all of the clot material PE (or a desired amount of the clot material PE) from the blood vessel BV. That is, a single aspiration may not adequately remove the clot material PE from the blood vessel BV. In such instances, the user of the assembly 10 may wish to again apply vacuum pressure (conduct an "aspiration pass") to remove all or a portion of the remaining clot material PE in the blood vessel BV. In such instances, the pressure source can be disconnected from the tubing subsystem 120 and drained (e.g., aspirated clot removal removed) before the method 800 returns to block 802. For example, the adaptor 350 and the syringe 340 can be decoupled from the connector 128, and the plunger 342 can be pushed into the barrel 344 to expel the clot material PE and associated fluid from the barrel 344 via the tip 347. With the distal portion of the catheter 102 positioned proximate to the remaining clot material PE (e.g., unmoved relative to the last aspiration pass), the pressure source can then be re-coupled to the connector 128 (block 804), primed again (block 806), and the vacuum pressure discharged (block 808) to aspirate all or a portion of the remaining clot material PE.

Blocks 802-808 can be repeated until a desired amount of clot material is removed from the patient or until the catheter 102 becomes clogged. In some embodiments, to check for clogging of the catheter 102, the fluid control device 126 and/or the valve 106 can be opened to check for back bleeding. A lack of back bleeding can indicate that the catheter 102 is likely clogged. Similarly, if the barrel 344 of the syringe 340 contains mostly air and relatively little blood and clot material (e.g., less than 5-10 cc) after aspiration of the catheter 102 (block 808), it can indicate that the catheter 102 is likely clogged. When the catheter 102 is clogged or a sufficient amount of clot material PE has been removed from the patient, the method 800 can proceed to block 810 and the catheter 102 can be removed from the patient. When the catheter 102 is clogged, the catheter 102 can be flushed and cleared prior to reentry into the patient (block 802). In other embodiments, a different (e.g., new, unused, etc.) catheter can be inserted into the patient and positioned to remove the remaining clot material PE from the patient.

In some embodiments, rather than removing the catheter 102 from the patient if the catheter 102 is clogged, the syringe 340 can be recharged and used to apply one or more subsequent vacuum pulses to the catheter 102. More specifically, the fluid control device 126 can be closed and the syringe 340 can be removed from the connector 128 and evacuated to remove the clot material and blood therein. Then, blocks 804-808 can be repeated to apply another pulse of vacuum to the catheter 102. That is, rather than removing the catheter 102 after a clog is detected, the syringe 340 can be "cycled" until the vacuum force on the clot material PE overcomes the forces between the clot material PE and the catheter 102 and sucks the clot material PE into the syringe 340. In some embodiments, when the pressure source 400 with the secondary syringe 460 (FIGS. 4A-4C) is used with the primary syringe 340, the secondary syringe 460 can be cycled one or more times to increase the vacuum in the assembly 10 (e.g., in the catheter 102) and thus increase the suction force exerted against the clot material PE. That is, rather than removing the catheter 102 after a clog is detected, the secondary syringe 460 can be cycled until the vacuum force on the clot material PE overcomes the forces between the clot material PE and the catheter 102 and sucks the clot material PE into the syringe 340. In some embodiments, as described in detail below with reference to FIGS. 15-16E, a second clot removal assembly can be telescoped through the first assembly 10 to facilitate removal of the clogged clot material PE.

In some embodiments, an interventional device such as a clot removal and/or clot treatment device can be delivered to the treatment site through the catheter 102 for engaging and facilitating clot removal before and/or after application of a stored vacuum to the catheter 102. Suitable interventional devices and associated methods are disclosed in U.S. Pat. No. 9,526,864, filed Jun. 9, 2015, and titled "RETRACTION AND ASPIRATION DEVICE FOR TREATING EMBOLISM AND ASSOCIATED SYSTEMS AND METHODS," and U.S. Pat. No. 8,784,434, filed Mar. 15, 2013, and titled "METHODS AND APPARATUS FOR TREATING EMBOLISM," both of which are incorporated herein by reference in their entireties. In some embodiments, for example, the user can first advance an interventional device to the treatment site and at least partially engage the clot material PE with the interventional device to loosen (e.g., scour) the clot material PE. Such loosening of the clot material PE can facilitate the removal of the clot material PE upon a subsequent aspiration pass. Likewise, in some embodiments, the user can use an interventional device to engage residual clot material PE (FIG. 10B) after a first aspiration pass.

Figure 11:
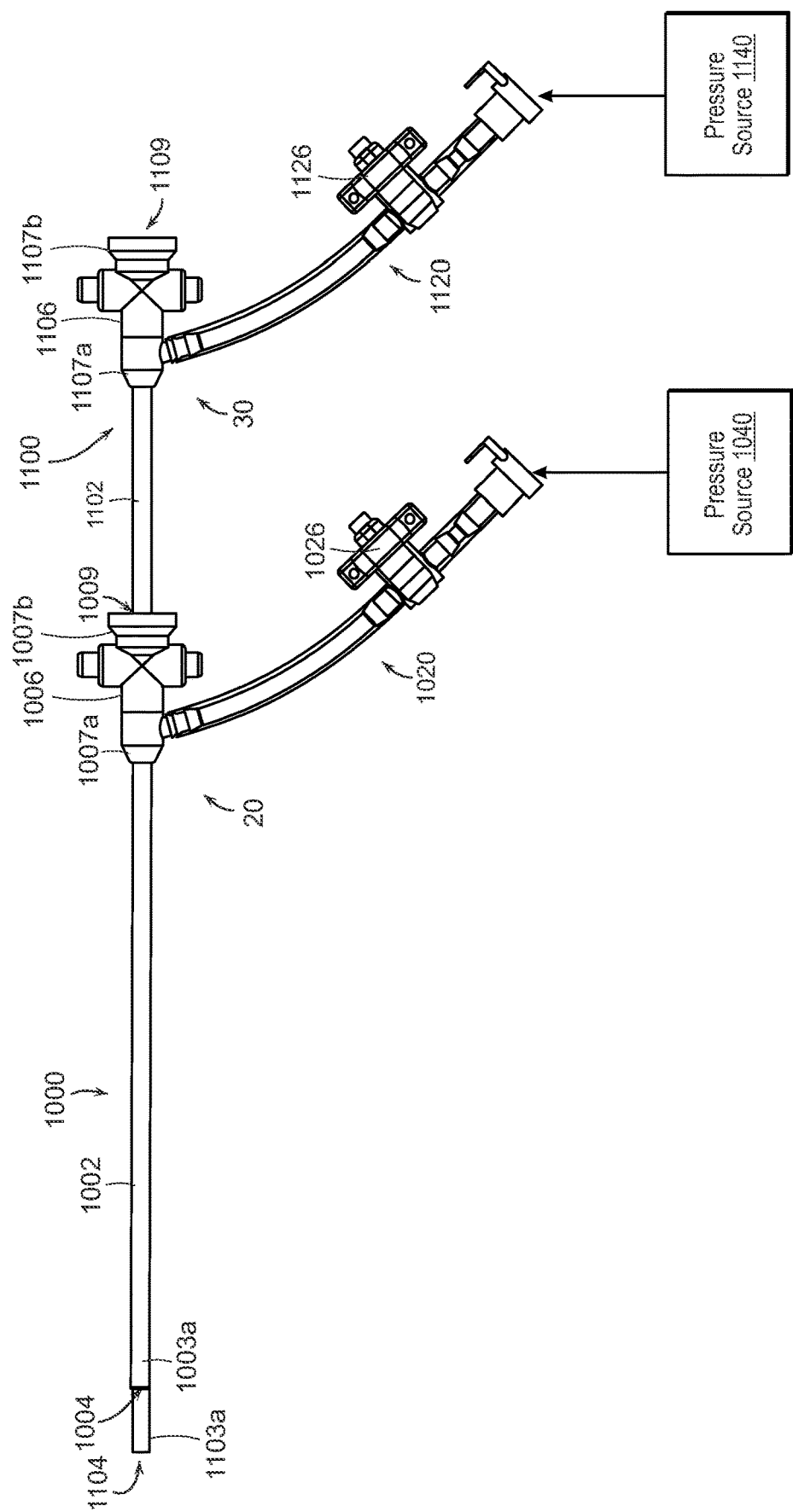
FIG. 11 is a partially schematic side view of another clot removal system configured in accordance with the present technology.

IV. Selected Embodiments of Telescoping Clot Removal Systems and Associated Methods of Clot Removal FIG. 11 is a partially schematic side view of another clot treatment or clot removal system configured in accordance with the present technology. In the illustrated embodiment, the clot removal system includes a first aspiration assembly 20 and a second aspiration assembly 30. The first and second aspiration assemblies 20, 30 ("assemblies 20, 30") can include some features generally similar to the features of the aspiration assembly 10 described in detail above with reference to FIGS. 1-10B. For example, the first aspiration assembly 20 includes (i) a first catheter subsystem 1000 having a first catheter 1002 and a first valve 1006, (ii) a first tubing subsystem 1020 having a first fluid control device 1026 (e.g., a stopcock), and (iii) a first pressure source 1040 that can be fluidly coupled to the first catheter subsystem 1000 via the first tubing subsystem 1020. Likewise, the second aspiration assembly 30 includes (i) a second catheter subsystem 1100 having a second catheter 1102 and a second valve 1106, (ii) a second tubing subsystem 1120 having a second fluid control device 1126 (e.g., a stopcock), and (iii) a second pressure source 1140 that can be fluidly coupled to the second catheter subsystem 1100 via the second tubing subsystem 1120.

The first and second catheters 1002, 1102 each comprise an elongated shaft defining a lumen 1004, 1104 and having a distal portion 1003*a*, 1103*a*, respectively. The first and second valves 1006, 1106 each include (i) a distal portion 1007*a*, 1107*a*, (ii) a proximal portion 1007*b*, 1107*b*, (iii) a lumen 1009, 1109 extending therethrough, and (iv) a flow controller (obscured in FIG. 10) in the lumen 1009, 1109, respectively. The first fluid control device 1026 is operable to regulate or control fluid flow between (e.g., fluidly connect or disconnect) the first pressure source 1040 and the first catheter subsystem 1000. The second fluid control device 1126 is operable to regulate or control fluid flow between (e.g., fluidly connect or disconnect) the second pressure source 1140 and the second catheter subsystem 1100.

In the illustrated embodiment, the second catheter 1102 has a smaller cross-sectional dimension (e.g., diameter) than the first catheter 1002 so that the second catheter 1102 can be inserted through the first valve 1006 and into the lumen 1004 of the first catheter 1002. In some embodiments, the second catheter 1102 can be telescoped through the lumen 1004 of the first catheter 1002 until the distal portion 1103*a* of the second catheter 1102 extends beyond a distal terminus of the first catheter 1002. Accordingly, the second catheter 1102 can be longer than the first catheter 1002. In some embodiments, the second catheter 1102 can have a size of 16 French or smaller and the first catheter 1002 can have a size of 20 French or greater. The first valve 1006 can provide a hemostatic seal that inhibits fluid flow (e.g., blood flow) through the first valve 1006 and from the first catheter subsystem 1000 when the second catheter 1102 is positioned within the first catheter 1002. In some embodiments (e.g., as described in detail below with reference to FIGS. 14A-14C), a sealing member 1499 can be positioned between the first catheter 1002 and the second catheter 1102 for sealing the lumen 1004 of the first catheter 1002 when the second catheter 1102 is advanced distally past the sealing member.

In some embodiments, the first and second pressure sources 1040, 1140 ("pressure sources 1040, 1140") are separate sources each configured to generate and store a vacuum for subsequent application to the first and second catheter subsystems 1000, 1100, respectively, as described in detail above with reference to FIGS. 1-10B. In other embodiments, one or both of the pressure sources 1040, 1140 can be configured to provide sustained negative pressure rather than a charge or burst of stored vacuum pressure. In yet other embodiments, one of the pressures sources 1040, 1140 can be omitted, or the pressure sources 1040, 1140 can be fluidly coupled and/or integrally formed.

Figure 12:
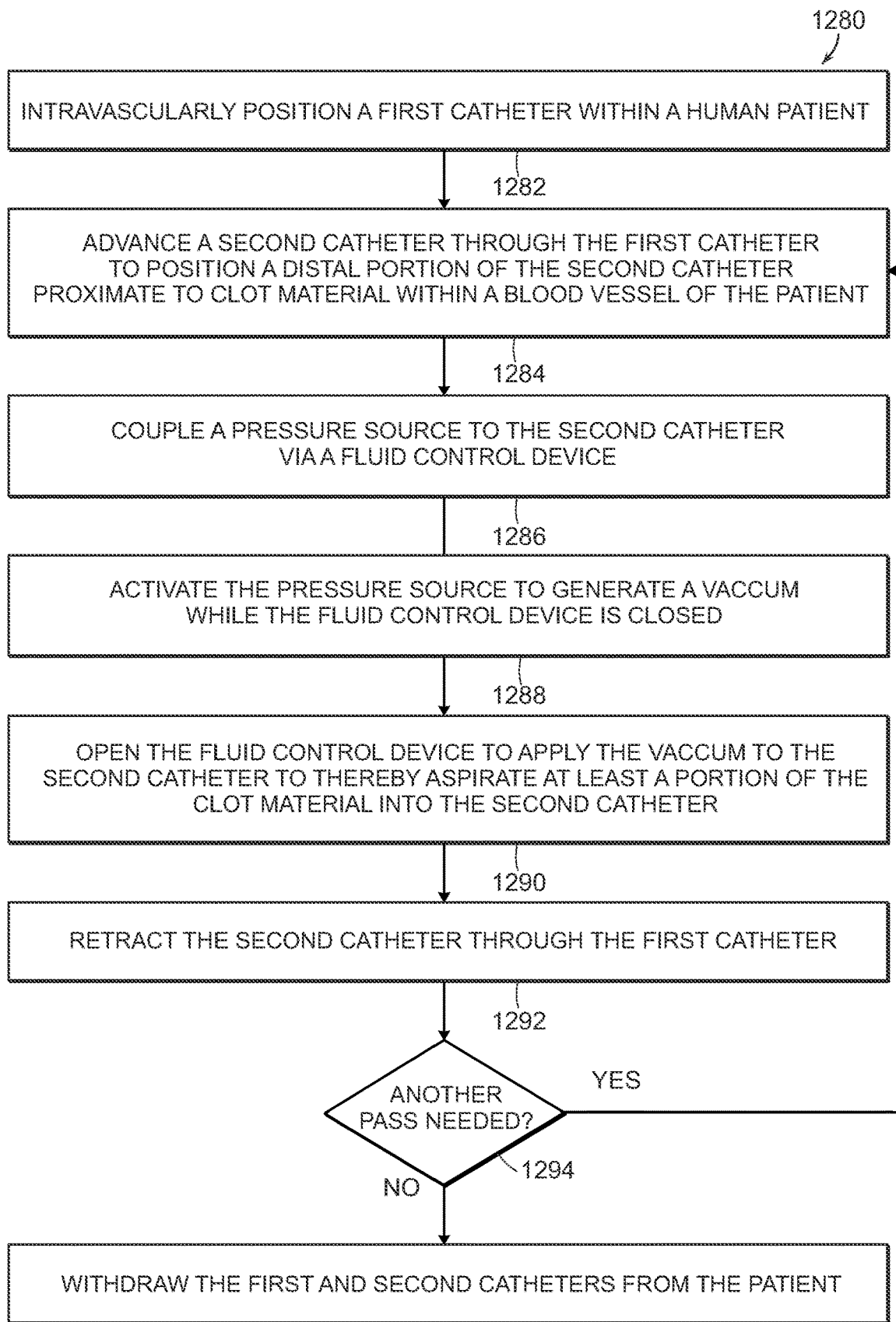
FIG. 12 is a flow diagram of another process or method for operating a clot removal system in accordance with the present technology.
Figure 13A:
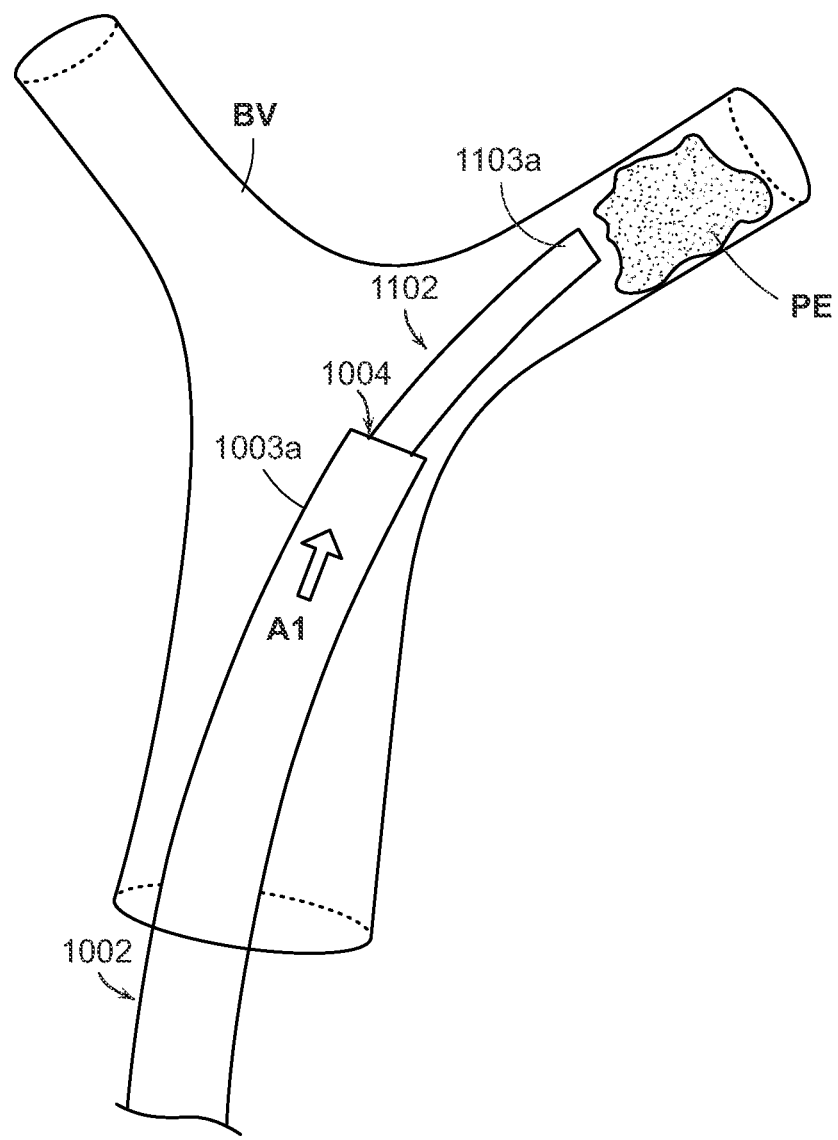
Figure 13B:
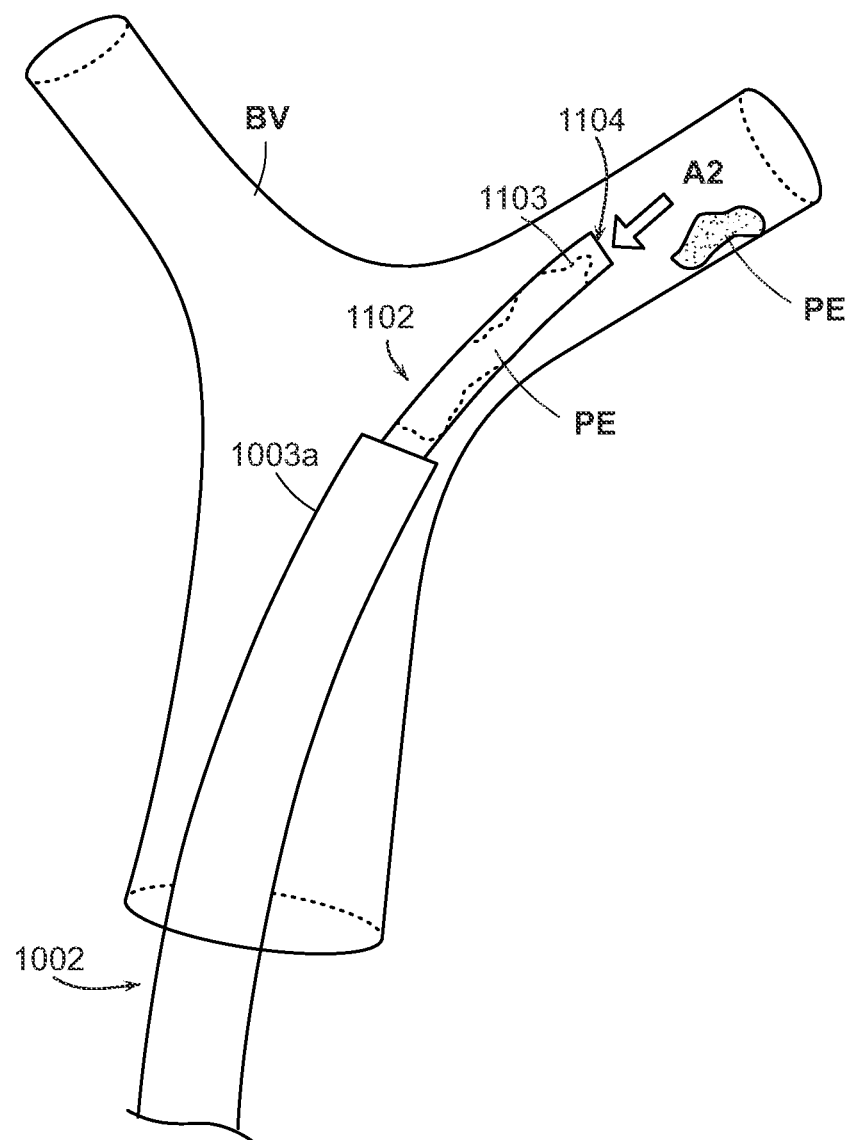
Figure 13C:
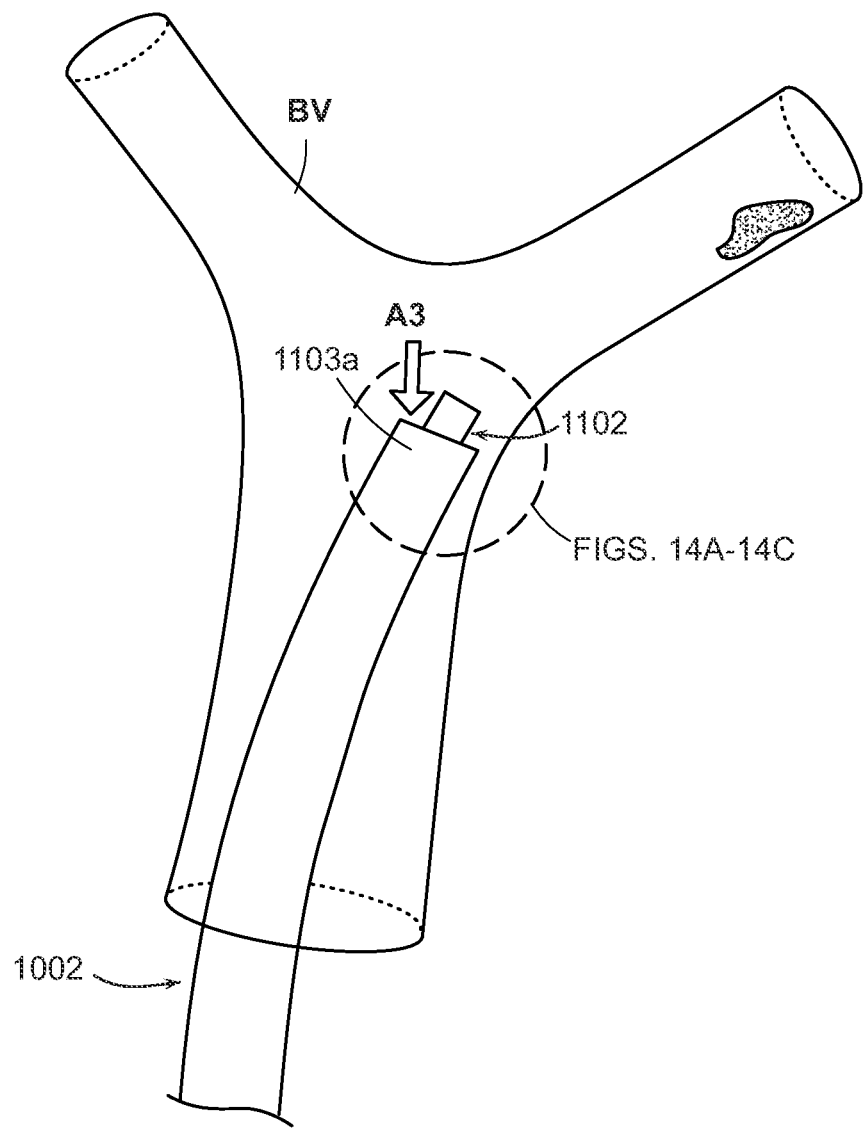

FIG. 12 is a flow diagram of a process or method 1280 for operating a clot removal system including the assemblies 20 and 30 to remove clot material from within a blood vessel (e.g., a pulmonary blood vessel) of a human patient in accordance with the present technology. FIGS. 13A-13C are schematic illustrations of a distal portion of the assemblies 20, 30 during a clot removal procedure in accordance with the present technology. FIGS. 14A-14C are schematic side views of a distal portion of the assemblies 20, 30 during a clot removal procedure and including an optional sealing member in accordance with the present technology. Although some features of the method 1280 are described in the context of the embodiments shown in FIGS. 11 and 13A-14C for the sake of illustration, one skilled in the art will readily understand that the method 1280 can be carried out using other suitable systems and/or devices.

At block 1282, the method 1280 includes intravascularly positioning the first catheter 1002 within a human patient. FIG. 13A, for example, illustrates the first catheter 1002 after it has been advanced (e.g., as indicated by arrow A1) to a position within a blood vessel BV (e.g., a pulmonary blood vessel). More specifically, the first catheter 1002 can be advanced within the blood vessel BV until the distal portion 1003*a* of the first catheter 1002 is positioned proximal to clot material PE within the blood vessel BV. In some embodiments, the position of the distal portion 1003*a* of the first catheter 1002 relative to the clot material PE can be determined by activating the first valve 1006 and determining whether there is back-bleeding through the first valve 1006, as described in detail above. In the illustrated embodiment, the clot material PE is located within a branch (e.g., a reduced diameter portion) of the blood vessel BV. In some embodiments, access to the blood vessel BV can be achieved using an introducer and guidewire as described in detail above with reference to FIG. 8.

At block 1284, the method 1280 includes advancing the second catheter 1102 through the first catheter 1002 until the distal portion 1103*a* of the second catheter 1102 is positioned proximate to the clot material PE within the blood vessel BV (e.g., at a treatment site). To advance the second catheter 1102 through the first catheter 1002, the user can first insert the distal portion 1103*a* of the second catheter 1102 through the first valve 1006 before advancing the second catheter 1102 (e.g., as indicated by the arrow A1) through the lumen 1004 of the first catheter 1002. In some embodiments, the first valve 1006 can be actuated (e.g., by depressing one or more buttons) to open the lumen 1009 of the first valve 1006 so that the second catheter 1102 can be inserted therethrough. In some embodiments, the position of the distal portion 1103*a* of the second catheter 1102 relative to the clot material PE can be determined by activating the second valve 1106 and determining whether there is back-bleeding through the second valve 1106, as described in detail above. In other embodiments, the (smaller) second catheter 1102 can be intravascularly positioned proximate to the clot material PE before intravascularly positioning the (larger) first catheter 1002. In such embodiments, the second catheter 1102 can act as a guide or rail for guiding the advancement of the first catheter 1002 to the treatment site.

FIG. 13A illustrates the second catheter 1102 after it has been advanced through the first catheter 1002 and past a distal terminus of the first catheter 1002 to position a distal terminus of the second catheter 1102 proximate to a proximal portion of the clot material PE. In other embodiments, the distal terminus of the second catheter 1102 can be positioned at least partially within the clot material PE, or the distal terminus of the second catheter 1102 can be positioned distal of the clot material PE. In one aspect of the present technology, because the second catheter 1102 has a smaller cross-sectional dimension than the first catheter 1002, the second catheter 1102 can be advanced to narrower (e.g., more distal) treatment sites within the blood vessel BV. In the embodiment illustrated in FIG. 13A, for example, the first catheter 1002 may be too large to be positioned within the branch of the blood vessel BV, while the second catheter 1102 can be positioned within the branch proximate to or within the clot material PE.

At block 1286, the method 1280 includes coupling the second pressure source 1140 to the second catheter 1102 via the second fluid control device 1126. For example, any one or combination of the pressure sources described in detail above with reference to FIGS. 2-7 can be coupled to the second catheter 1102 via the second tubing subsystem 1120. Once the second pressure source 1140 is coupled to the second catheter 1102, (i) opening of the second fluid control device 1126 fluidly connects the second pressure source 1140 to the lumen 1104 of the second catheter 1102, and (ii) closing of the second fluid control device 1126 fluidly disconnects the second pressure source 1140 from the lumen 1104 of the second catheter 1102. In some embodiments, the method 1280 can further include coupling the first pressure source 1040 to the first catheter 1002 (e.g., via the first tubing subsystem 1020).

At block 1288, the method 1280 includes activating the second pressure source 1140 to generate a vacuum while the second fluid control device 1126 is closed. In particular, the second pressure source 1140 can be activated to build-up or pre-charge a vacuum for subsequent application to the second catheter 1102. In some embodiments, the first pressure source 1040 can also be activated to generate and store a vacuum for subsequent application to the first catheter 1002.

At block 1290, the method 1280 includes opening the second fluid control device 1126 to apply the vacuum stored in second pressure source 1140 to the lumen 1104 of the second catheter 1102. As shown in FIG. 13B, application of the vacuum causes suction (e.g., as indicated by arrow A2) that aspirates at least a portion of the clot material PE from the blood vessel BV and into the lumen 1104 of the second catheter 1102. In some embodiments, opening the second fluid control device 1126 instantaneously or nearly instantaneously generates suction at the distal portion 1103a of the second catheter 1102. In one aspect of the present technology, pre-charging or storing the vacuum before applying the vacuum to the lumen 1104 of the second catheter 1102 is expected to generate greater suction forces (and corresponding fluid flow velocities) at and/or near the distal portion 1103a of the second catheter 1102 compared to simply activating the second pressure source 1140 while it is fluidly connected to the second catheter 1102.

In some embodiments, where the first pressure source 1040 is also activated to generate and store a vacuum (e.g., at block 1288), the method 1280 can further comprise opening the first fluid control device 1026 to generate suction at the distal portion 1003a of the first catheter 1002. One skilled in the art will understand that the suction profile in the blood vessel BV can be selected or modified based on the characteristics of the pressure sources 1040, 1140 (e.g., volume, bore size, etc.) and the timing of the opening of the first and second fluid control devices 1026, 1126. For example, the first fluid control device 1026 can be opened at the same time as the second fluid control device 1126 to generate a combined and relatively large suction force in the blood vessel BV. In other embodiments, the first fluid control device 1026 can be opened after the second fluid control device 1126 to generate staggered or stepped suction forces in the blood vessel BV. For example, the first fluid control device 1026 can be opened after the second fluid control device 1126 to aspirate any of the clot material PE (i) remaining in the blood vessel BV after aspiration of the second catheter 1102 and/or (ii) stuck to or extending from the second catheter 1102. In other embodiments, the first pressure source 1040 can be a pump or other source for providing sustained negative pressure—rather than a built-up charge of negative pressure—and thus can generate sustained (e.g., constant) suction at the distal portion 1003a of the first catheter 1002. In some such embodiments, the first fluid control device 1026 can remain open during the clot removal procedure to provide sustained suction throughout the procedure.

In some embodiments, an interventional device can be delivered through the second catheter 1102 and used to engage the clot material PE before and/or after the vacuum is applied to the second catheter 1102. Specific details of suitable interventional devices and associated methods of use are disclosed in, for example, provisional U.S. patent application Ser. No. 16/258,344, filed Jan. 25, 2019, and titled "SINGLE INSERTION DELIVERY SYSTEM FOR TREATING EMBOLISM AND ASSOCIATED SYSTEMS AND METHODS," which is incorporated herein by reference in its entirety.

At block 1292, the method 1280 includes retracting the second catheter 1102 proximally through the first catheter 1002. In some embodiments, multiple aspiration passes can be performed with the second catheter 1102 before retracting the second catheter 1102. In some embodiments, as shown in FIG. 13C, the first pressure source 1040 or another pressure source coupled to the first catheter 1002 can be activated to generate suction (e.g., as indicated by arrow A3) at the distal portion 1003a of the first catheter 1002 during retraction of the second catheter 1102. The suction can be constant or provided in one or more bursts, as described in detail above. In some embodiments, the second catheter 1102 can be fully withdrawn from the patient and disposed of or cleaned (e.g., flushed with a sterile liquid) for reuse.

Sometimes, the clot material PE is not fully pulled into the second catheter 1102 when the vacuum is applied to the second catheter 1102 (block 1290) and can therefore stick to or dangle from the distal portion 1103a of the second catheter 1102. FIG. 14A, for example, is an enlarged view of the distal portion of the assemblies 20, 30 shown in FIG. 13C and illustrating a portion of the clot material PE stuck to or dangling from the distal portion 1103a of the second catheter 1102. In the illustrated embodiment, an optional seal 1499 is disposed between the first and second catheters 1002, 1102 to facilitate the removal of such dangling clot material PE. More specifically, the seal 1499 (shown in cross-section) can be disposed between an outer surface of the second catheter 1102 and an inner surface of the first catheter 1002. The seal 1499 can be an O-ring, grommet, or other suitable component that fluidly disconnects the lumen 1004 of the first catheter 1002 from the blood vessel BV when the second catheter 1102 is positioned therethrough (e.g., when the distal terminus of the second catheter 1102 is positioned distally of the seal 1499).

FIGS. 14B and 14C are enlarged views of the distal portion of the assemblies 20, 30 and illustrating further retraction of the second catheter 1102 (and the dangling clot material PE) into the lumen 1004 of the first catheter 1002. In some embodiments, the first pressure source 1040 can be activated to charge a vacuum in the lumen 1004 of the first catheter 1002. For example, after the second catheter 1102 is advanced through the first catheter 1002 and past the seal 1499 (e.g., block 1284)—thereby sealing the lumen 1004 of the first catheter 1002—the operator can open the first fluid control device 1026 and activate the first pressure source 1040 to build up the vacuum in the lumen 1004 of the first catheter 1002. Referring to FIG. 14C, when the distal terminus of the second catheter 1102 is retracted proximally past the seal 1499, the lumen 1004 of the first catheter 1002 becomes fluidly connected to the blood vessel BV and the vacuum is instantaneously or nearly instantaneously released to generate suction (e.g., as indicated by arrows A4). In the illustrated embodiment, the suction acts to separate or otherwise dislodge the clot material PE from the second catheter 1102 and pull the clot material PE proximally through the lumen 1004 of the first catheter 1002. In this manner, a second burst of suction is automatically applied via the first catheter 1002 during retraction of the second catheter 1102. In one aspect of the present technology, the user does not need to take any additional step to release the vacuum stored in the first catheter 1002—as release is automatically triggered by retraction of the second catheter 1102.

At block 1294, the user can determine whether it is necessary or desirable to redeploy the second catheter 1102 or another catheter through the first catheter 1002 in order to remove any residual clot material PE that was not removed during the first aspiration pass and/or any clot material located elsewhere in the blood vessel BV (e.g., to initiate a second aspiration pass). In some embodiments, the operator can visualize the amount of clot material PE collected in the first pressure source 1040 and/or the second pressure source 1140 to at least partially determine whether another aspiration pass is needed. In other embodiments, the operator can rely on imaging (e.g., fluoroscopic imaging) of the blood vessel BV or other techniques known in the art to determine whether an additional aspiration pass is necessary or desirable.

If another pass is not needed (e.g., the clot material PE was adequately removed), the user can elect to fully withdraw the assemblies 20, 30 from the patient at block 1296. If clot material PE remains in the vessel, the method can return to block 1284. In particular, the same second catheter 1102 can be cleaned (e.g., flushed with saline) and advanced again through the first catheter 1002 until the distal portion 1103a of the second catheter 1102 is positioned proximate to the remaining clot material PE within the blood vessel BV. In some embodiments, a new second catheter 1102 can be used for each pass to reduce the likelihood of contamination (e.g., reintroduction of clot material PE). In some embodiments, the first catheter 1002 can be aspirated (e.g., via the first pressure source 1040) prior to redeployment of the second catheter 1102 to, for example, remove any clot material PE that may be in the first catheter 1002 to inhibit its reintroduction into the blood vessel BV as the second catheter 1102 is advanced therethrough during another pass. Once the desired amount of clot material PE has been removed from the patient, the assemblies 20, 30 may be fully withdrawn from the patient (block 1294).

In one aspect of the present technology, the method 1280 provides for an aspiration catheter to be deployed multiple times without requiring that the first catheter 1002 be removed after each deployment. Accordingly, the present technology allows for only a single insertion of a guide catheter during a procedure including multiple passes to remove clot material—increasing the speed of the procedure and reducing trauma to the patient since the guide catheter does not need to be reintroduced (e.g., advanced through the vasculature and past the heart) before each pass. Moreover, in certain embodiments, the present technology can enable the first catheter 1002 to be relocated to an alternate treatment site within the patient without removing the first catheter 1002 from the patient and, therefore, without reintroducing the first catheter 1002 through the heart. For example, the first catheter 1002 can be relocated to another treatment site within the lungs including a treatment site in the opposite lung. More specifically, (i) a dilator can be reintroduced into the first catheter 1002, (ii) the first catheter 1002 can be withdrawn into the main pulmonary artery, (iii) a guidewire can be redirected to the new treatment site, (iv) the first catheter 1002 can be advanced over the guidewire to the new treatment site, and (v) the dilator can be removed.

Figure 15:
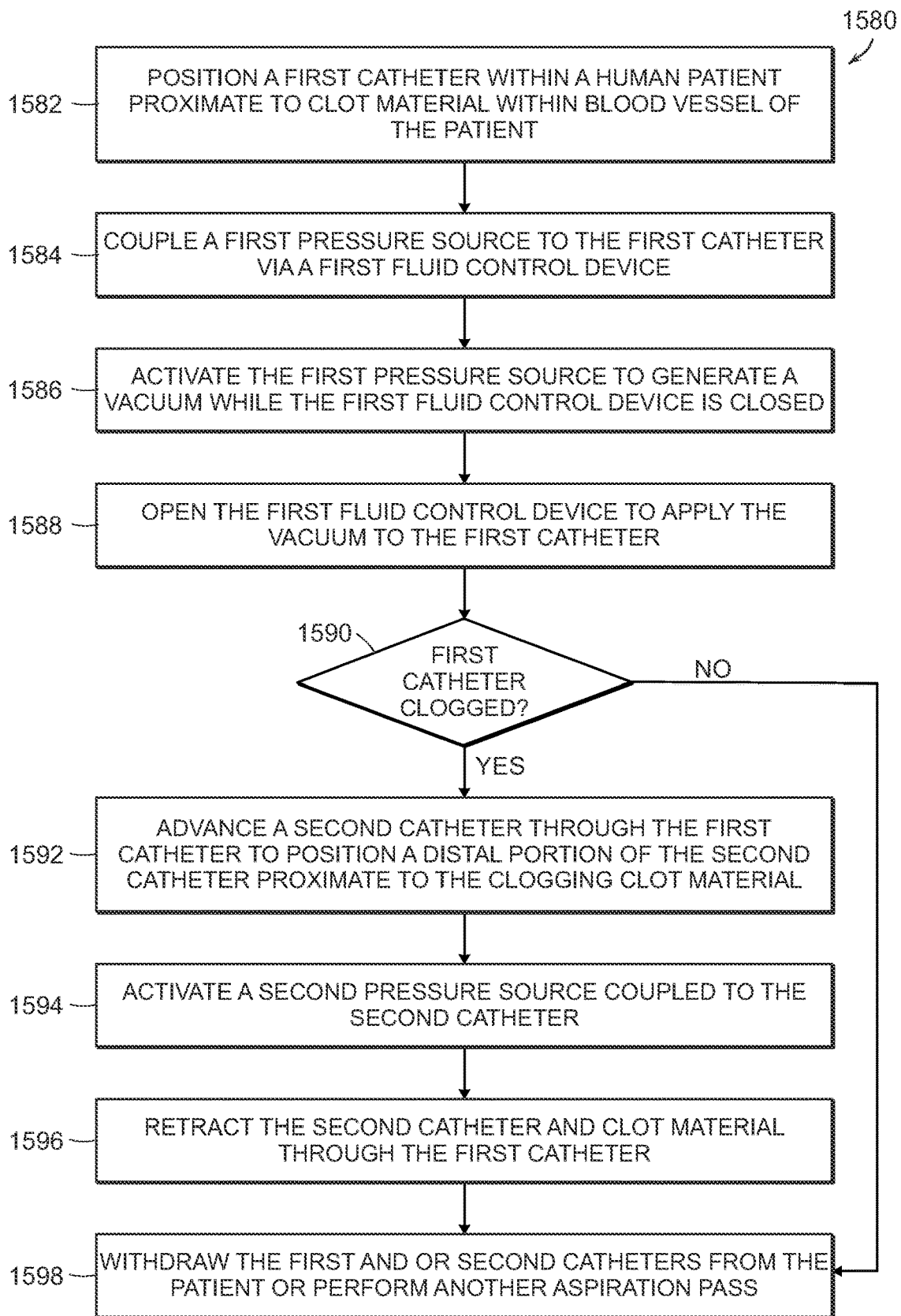
FIG. 15 is a flow diagram of another process or method for operating a clot removal system in accordance with the present technology.
Figure 16E:
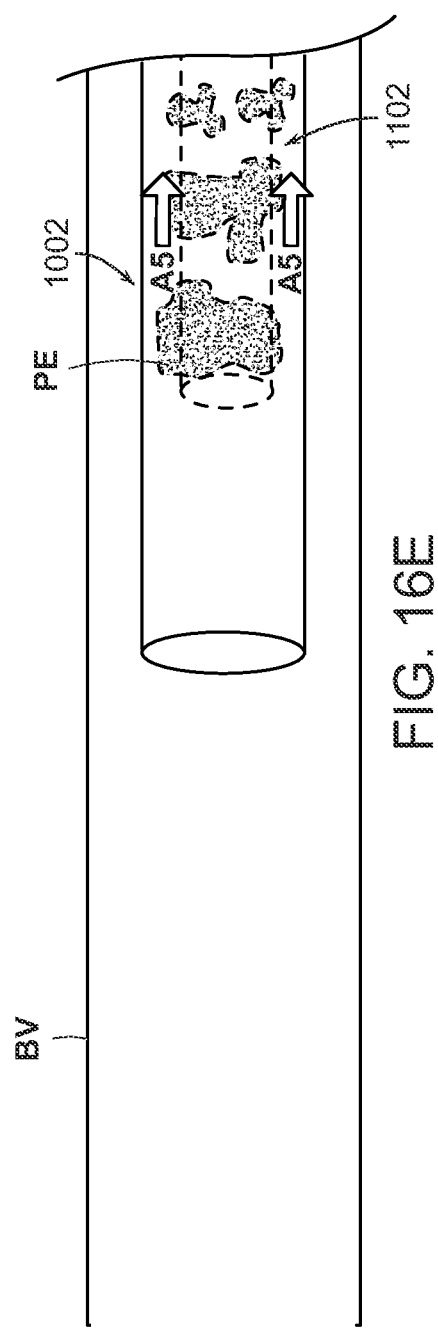

FIG. 15 is a flow diagram of another process or method 1580 for operating a clot removal system including the assemblies 20, 30 (FIG. 1) to remove clot material from within a blood vessel (e.g., a pulmonary blood vessel) of a human patient in accordance with the present technology. FIG. 16A is an enlarged side view of a distal portion of the first assembly 20, and FIGS. 16B-16E are side views of a distal portion of the assemblies 20, 30 during a clot removal procedure in which clot material clogs the first assembly 20 in accordance with the present technology. Although some features of the method 1580 are described in the context of the embodiments shown in FIGS. 11 and 16A-16E for the sake of illustration, one skilled in the art will readily understand that the method 1580 can be carried out using other suitable systems and/or devices.

Some features of the method 1580 are generally similar to those of the methods 880 and/or 1280 described in detail above with reference to FIGS. 8 and 12, respectively. For example, at block 1582 the method includes intravascularly positioning the first catheter 1002 of the first assembly 20 within a human patient. At block 1584, the method 1580 includes coupling the first pressure source 1040 to the first catheter 1002 via the first fluid control device 1026. For example, any one or combination of the pressure sources described in detail above with reference to FIGS. 2-7 can be coupled to the second catheter 1002 via the first tubing subsystem 1020. At block 1586, the method 1580 includes activating the first pressure source 1040 to generate a vacuum while the first fluid control device 1026 is closed. In particular, the first pressure source 1040 can be activated to build-up or pre-charge a vacuum for subsequent application to the first catheter 1002. At block 1588, the method 1580 includes opening the first fluid control device 1026 to apply the vacuum stored in the first pressure source 1040 to the lumen 1004 of the first catheter 1002. As described in detail above, opening the first fluid control device 1026 instantaneously or nearly instantaneously generates suction at the distal portion 1003a of the first catheter 1002.

Sometimes, however, clot material is not fully pulled into the first catheter 1002 and/or clogs the first catheter 1002 when the vacuum is applied to the first catheter 1002 (block 1588). FIG. 16A, for example, is an enlarged view of the distal portion of the first assembly 20 illustrating a portion of clot material PE that extends beyond from the distal portion 1003a of the first catheter 1002 and blocks/clogs the lumen 1004 of the first catheter 1002. As such, a portion of the clot material PE is not within the first catheter 1002. Accordingly, at block 1590, the method 1580 can include determining whether the first catheter 1002 is clogged. In some embodiments, the operator can determine that the first catheter 1002 is clogged based on the vacuum chamber of the first pressure source 1040 containing little to no clot material PE and blood. For example, since the clot material PE clogs the first catheter 1002, the vacuum chamber of the first pressure source 1040 cavitates when the first fluid control device 1026 is opened. If the first catheter 1002 is not clogged, the method 1580 can proceed to block 1598 and the first catheter 1002 can be withdrawn from the patient or the operator can perform another aspiration pass (e.g., as described in detail above with reference to blocks 808 and 810 of the method 800 shown in FIG. 8).

If the first catheter 1002 is clogged, the method 1580 can proceed to block 1592 which includes advancing the second catheter 1102 through the first catheter 1002 until the distal portion 1103a of the second catheter 1102 is positioned in or proximate to the clogging clot material PE. For example, FIG. 16B illustrates the second catheter 1102 after it has been advanced to a position within the first catheter 1002 in which the distal terminus of the second catheter 1102 is at or proximate to the clogging clot material PE. To advance the second catheter 1102 through the first catheter 1002, the user can first insert the distal portion 1103a of the second catheter 1102 through the first valve 1006 (FIG. 11) before advancing the second catheter 1102 through the lumen 1004 of the first catheter 1002.

At block 1594, the method 1580 includes activating the second pressure source 1140 (FIG. 11) coupled to the second catheter 1102. More specifically, the second pressure source 1140 (e.g., any one or combination of the pressure sources described in detail above with reference to FIGS. 2-7) can be coupled to the second catheter 1102 via the second fluid control device 1126 (FIG. 11), and the second pressure source 1140 can be activated to build-up or pre-charge a vacuum while the second fluid control device 1126 is closed. The second fluid control device 1126 can then be actuated to apply the vacuum stored in the second pressure source 1140 to the lumen 1104 of the second catheter 1102. In other embodiments, the second pressure source 1140 can simply provide a sustained vacuum rather than an instantaneous release of vacuum. That is, in some embodiments the second pressure source 1140 is not pre-charged with a vacuum.

Applying the vacuum to second catheter 1102 can aspirate at least a portion of the clogging clot material PE into the second catheter 1102 and/or suck the clot material PE against the distal terminus of the second catheter 1102. FIG. 16C, for example, illustrates a portion of the clot material PE stuck to or extending from the distal portion 1103a of the second catheter 1102 after aspirating the second catheter 1102. In the embodiment illustrated in FIG. 16C, the added vacuum pressure generated through the second catheter 1102 is still not enough to break apart the clot material PE such that it can be fully aspirated through the first and/or second catheters 1002, 1102. That is, the clot material PE clogs the lumen 1004 of the first catheter 1002. In other embodiments, the added vacuum pressure from the second pressure source 1140 is sufficient to break apart the clot material PE such that it is aspirated into, for example, the vacuum chambers of the first and/or second pressure sources 1040, 1140.

At block 1596, the method can include retracting the second catheter 1102 and the clot material PE through the lumen 1004 of the first catheter 1002. For example, FIG. 16D illustrates retracting the second catheter 1102, which in turn retracts the attached clot material PE, through the lumen 1004 of the first catheter 1002. In some embodiments, the second catheter 1102 and clot material PE can be fully withdrawn through the first catheter 1002. In other embodiments, retracting the clot material PE through the first catheter 1002 causes the clot material PE to break apart and be aspirated into the vacuum chambers of the first and/or second pressure sources 1040, 1140. FIG. 16E, for example, illustrates the clot material PE breaking apart as the vacuum of the first and/or second pressure sources 1040, 1140 is instantaneously or nearly instantaneously released to suck the clot material PE proximally (e.g., as indicated by arrows A5).

At block 1598, the first and second catheters 1002, 1102 can be withdrawn from the patient or the operator can perform another aspiration pass using one or both of the first and second catheters 1002, 1102.

In one aspect of the present technology, the method 1580 removes clot material even when a first aspiration pass clogs the first catheter 1002. More particularly, the second catheter 1102 can be used to remove clogged clot material PE without requiring the first catheter 1002 and the clogged clot material PE to be withdrawn through the blood vessel BV.

V. Additional Selected Embodiments of Clot Removal Systems and Associated Methods of Clot Removal From the foregoing, it will be appreciated that specific embodiments of the present technology have been described herein for purposes of illustration, but that various modifications may be made without deviating from the scope of the present technology. For example, in many of the embodiments described above, stored vacuum pressure can be used to aspirate or suck clot material from a blood vessel and into a catheter without the need to engage an interventional device with the clot material. However, one skilled in the art will understand that the aspiration devices and techniques disclosed herein can be used in conjunction with any suitable interventional device and/or during a clot removal procedure utilizing an interventional device. In some embodiments, for example, a clot removal system can be configured to apply stored vacuum pressure to a guide catheter to generate a burst of suction while an interventional device is retracted into and/or through the guide catheter.

Figure 17:
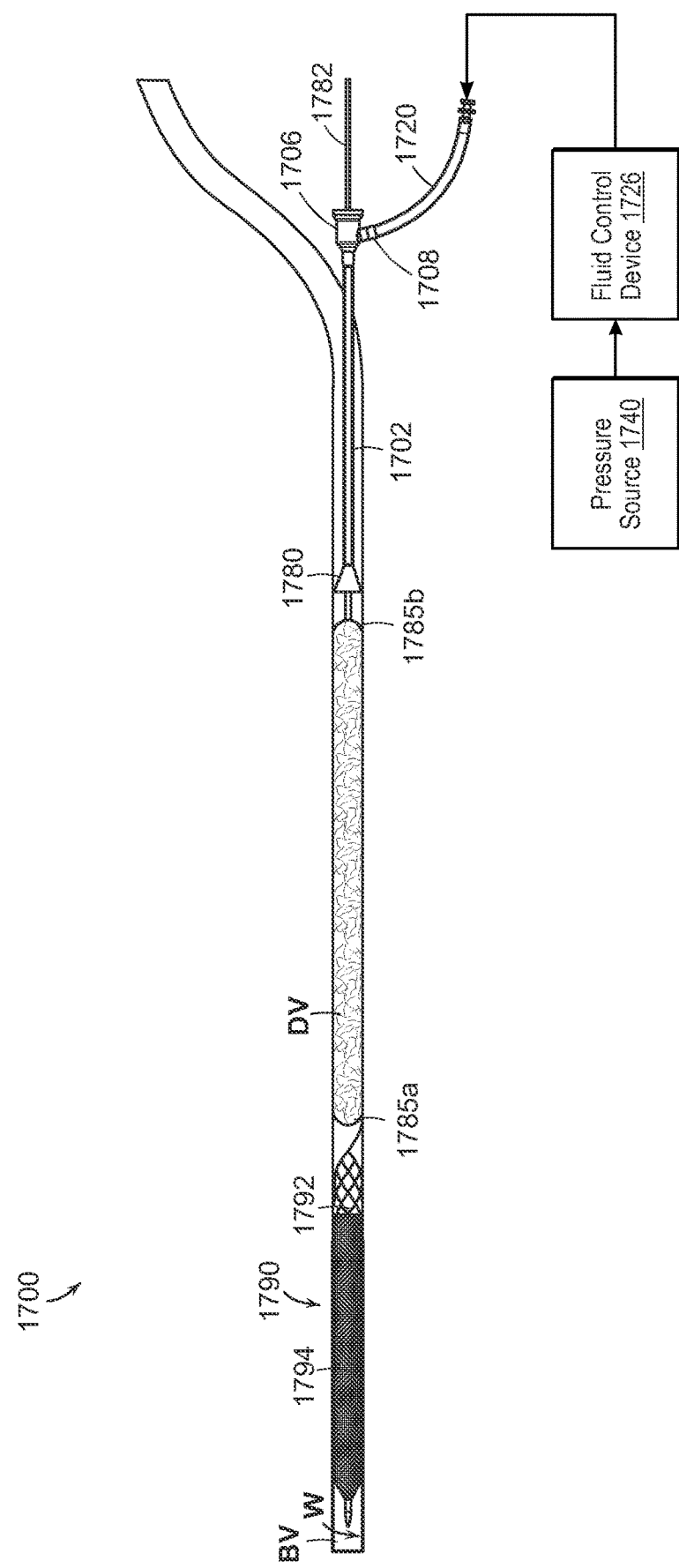
FIG. 17 is a partially schematic side view of another clot removal system configured in accordance with the present technology.

FIG. 17, for example, is a partially schematic view of a clot removal system 1700 ("system 1700") configured in accordance with the present technology. The system 1700 includes some features generally similar to the features of the clot removal system described in detail above with reference to FIG. 1. For example, the system 1700 includes a catheter or sheath 1702 comprising an elongated shaft, and a valve 1706 coupled to a proximal portion of the sheath 1702. The valve 1706 has a side port 1708 that fluidly couples a lumen of the sheath 1702 to a tubing subsystem 1720 and a pressure source 1740 (shown schematically). A fluid control device 1726 (e.g., a stopcock or clamp; shown schematically) is operable to fluidly disconnect or connect the pressure source 1740 from/to the lumen of the sheath 1702. The pressure source 1740 can be any suitable pressure source for generating and storing vacuum pressure, as described in detail above.

Figure 18E:
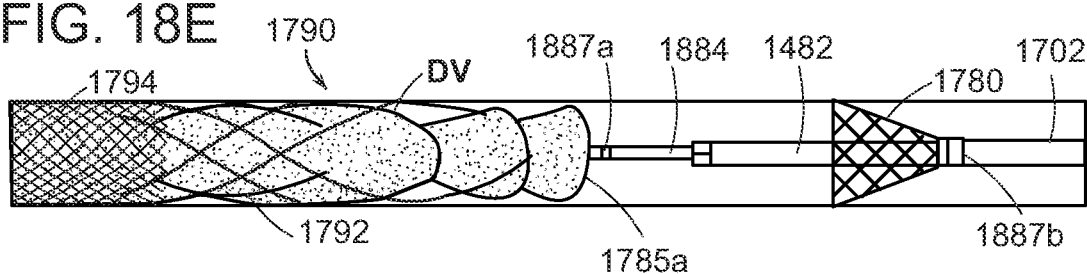
Figure 18F:
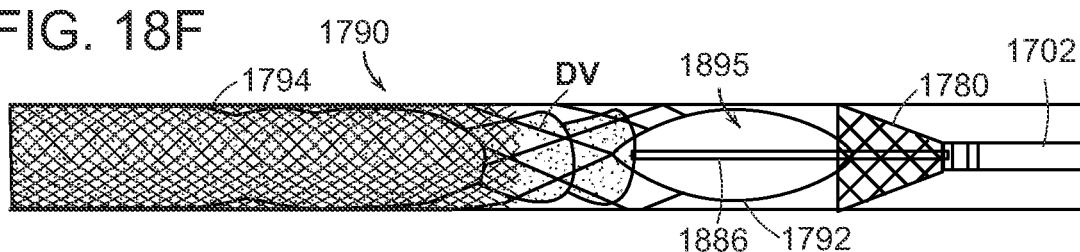

In the illustrated embodiment, the system 1700 further includes (i) a self-expanding (e.g., mesh) funnel 1780 coupled to a proximal portion of the sheath 1702 and (ii) an interventional device (e.g., a thrombus extraction device) 1790. In the illustrated embodiment, the interventional device 1790 includes an expandable coring element (e.g., a first portion) 1792 coupled to an expandable cylindrical element (e.g., a second portion) 1794. In some embodiments, the interventional device 1790 is configured to self-expand from a compressed delivery state to an expanded deployed state. The interventional device 1790 is shown in the deployed state in FIG. 17. An elongated shaft 1782 and/or one or more shafts positioned within the elongated shaft 1782 (e.g., an intermediate shaft 1884 and an inner shaft 1886 as shown in FIGS. 18E and 18F, respectively) are coupled to the interventional device 1790 and configured to retract, advance, and/or manipulate (e.g., move between the delivery and deployed states) the interventional device 1790. In some embodiments, the system 1700 can be generally the same as or similar to any of the clot removal systems disclosed in U.S. Patent Application Publication No. 2018/0193043, filed Apr. 26, 2017, and titled "DEVICES AND METHODS FOR TREATING VASCULAR OCCLUSION," which is incorporated herein by reference in its entirety.

In the illustrated embodiment, the system 1700 is shown intravascularly positioned within a blood vessel BV of a human patient and proximate to clot material DV (e.g., a deep vein thrombus) within the blood vessel BV. Specifically, FIG. 17 shows the system 1700 after (i) advancing the sheath 1702 to a position proximate to a proximal portion 1785*b* of the clot material DV, (ii) deploying the funnel 1780, (iii) deploying the interventional device 1790 from the sheath 1702 (e.g., by advancing the interventional device 1790 through the valve 1706 and the sheath 1702 to a position distal of a distal portion 1785*a* of the clot material DV), and (iv) expanding the interventional device 1790 from the compressed delivery state to the deployed state.

FIGS. 18A-18H are enlarged views of a distal portion of the system 1700 during a clot removal procedure in accordance with the present technology. In general, FIGS. 18A-18H illustrate the proximal retraction of the interventional device 1790 through the clot material DV to capture at least a portion of the clot material DV, and the subsequent joint retraction of the interventional device 1790 and the captured clot material into the funnel 1780 and the sheath 1702. In one aspect of the present technology, charged vacuum pressure generated in the vacuum source 1740 can be applied to the sheath 1702 at one or more times during the illustrated process to generate suction for aspirating the captured clot material DV through the sheath 1702 and/or to inhibit clogging of the sheath 1702.

Referring first to FIG. 18A, proximal retraction of the interventional device 1790 causes the coring element 1792 to separate and/or core the distal end portion 1785*a* of the clot material DV from the walls W of the blood vessel BV. As shown in FIG. 18B, continued proximal retraction of the interventional device 1790 through the clot material DV causes the cylindrical element 1794 to capture the distal end portion 1785*a* of the clot material therein. FIGS. 18C-18E illustrate further proximal retraction of the interventional device 1790 which causes further separation, coring, and/or capture of the clot material DV. As seen in FIG. 18E, the proximal end portion 1785*b* of the clot material DV is cored and captured as the interventional device 1790 is proximally retracted toward the funnel 1780 and the sheath 1702. As further shown in FIG. 18E, a first radiopaque marker 1887*a* can be positioned on a distal end portion of the inner shaft 1884 and a second radiopaque marker 1887*b* can be positioned on a distal end portion of the sheath 1702.

In some embodiments, as shown in FIG. 18F, the interventional device 1790 can be proximally retracted until a portion of the coring element 1792 is contained (e.g., positioned) within the funnel 1780. More specifically, the interventional device 1790 can be proximally retracted until a mouth 1895 of the coring element 1792 is contained within the funnel 1780. In some embodiments, the containment of the mouth 1895 within the funnel 1780 can be fluoroscopically verified by visualization of the radiopaque markers 1887 (FIG. 18E). In some embodiments, for example, the mouth 1895 can be determined as wholly contained within the funnel 1780 via fluoroscopic monitoring based on the alignment of the distal end portion of the inner shaft 1884 (e.g., the first radiopaque marker 1885*a*) relative to the distal end portion of the sheath 1702 (e.g., the second radiopaque marker 1885*b*). In some embodiments, when the mouth 1895 of the coring element 1792 is positioned within the funnel 1780, the interventional device 1790 can be moved or transformed from the expanded deployed state to the compressed delivery state to compress and secure the clot material DV captured by the interventional device 1790. In some embodiments, for example, the intermediate shaft 1884 can be unlocked and/or decoupled from the inner shaft 1886 (e.g., via user actuation of a plunger or other device) such that the inner shaft 1886 can be advanced distally relative to the intermediate shaft 1884 to collapse or compress the interventional device 1790.

Figure 18G:
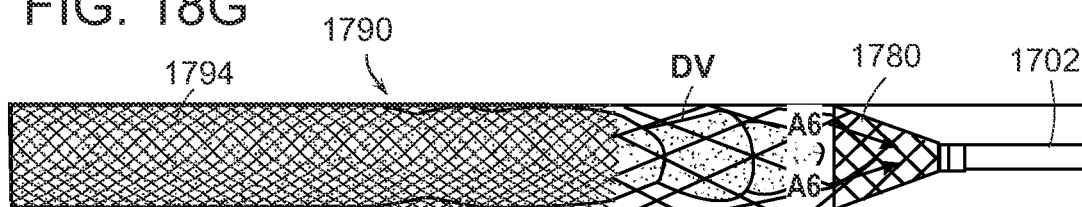
Figure 18H:
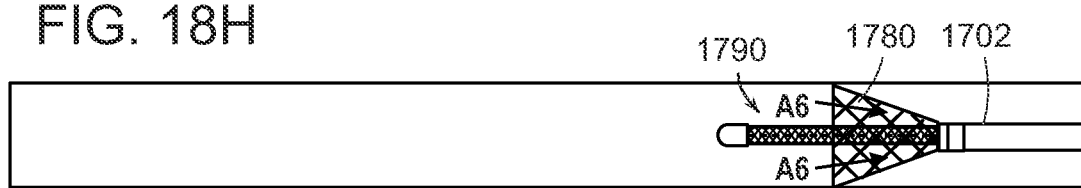

After the interventional device 1790 has been collapsed, the interventional device 1790 can be proximally retracted through the funnel 1780 and into the sheath 1702 as depicted in FIG. 18G. As shown in FIG. 18H, the interventional device 1790 can continue to be proximally retracted until the interventional device 1790 and the captured clot material DV are fully contained within the sheath 1702. In some embodiments, the interventional device 1790 and the captured clot material DV can then be withdrawn through the sheath 1702 and the valve 1706 (FIG. 17), and from the patient's body.

In some embodiments, the collapse of the interventional device 1790 and/or the retraction of the interventional device 1790 into the funnel 1780 and/or the sheath 1702 can result in one or more portions of the clot material DV breaking away from the clot material DV contained in the interventional device 1790. For example, all or a portion of the captured clot material DV can be extruded through pores of the (e.g., mesh) cylindrical element 1794 as the interventional device 1790 collapses. In some embodiments, any such clot material can be captured by the funnel 1780. Referring to FIG. 17, in some embodiments, the pressure source 1740 can be activated to charge a vacuum, and the fluid control device 1726 can subsequently be opened to apply the charged vacuum to the sheath 1702 (as described in detail above). The vacuum can be applied to the sheath 1702 at any point during retraction of the interventional device 1790. As shown in FIGS. 18G and 18H, application of the vacuum can generate instantaneous or nearly instantaneous suction (e.g., as indicated by arrows A6) at the distal end portion the sheath 1702 that can aspirate the extruded portions and/or other portions of the clot material DV into and/or through the sheath 1702. In particular, the generated suction can aspirate some or all of the clot material DV captured by the funnel 1780. Moreover, in some embodiments, application of a vacuum from the pressure source 1740 can facilitate smooth retraction of the captured clot material DV through the sheath 1702. For example, a burst of suction generated by application of the vacuum can help inhibit clogging of the sheath 1702, and/or help resolve (e.g., break apart) a clog formed in the sheath 1702 during retraction.

VI. Selected Embodiments of Clot Removal Systems Having Filters and Associated Methods of Clot Removal The systems and methods for clot removal described herein can include applying a pre-charged vacuum to generate suction for aspirating clot removal from the blood vessel of a patient. In one aspect of the present technology, aspiration of the clot material also aspirates blood from the patient. It can be advantageous to reintroduce the aspirated blood to the patient to lessen the trauma to the patient— especially where the removal procedure may comprise multiple aspiration passes that can together withdraw a significant amount of blood. However, the aspirated blood is often mixed with clot material and is therefore not suitable for reintroduction into the patient. FIGS. 19-20E illustrate various devices for filtering aspirated blood from removed clot material to reintroduce the aspirated blood into the patient without reintroducing a significant amount of clot material.

Figure 19:
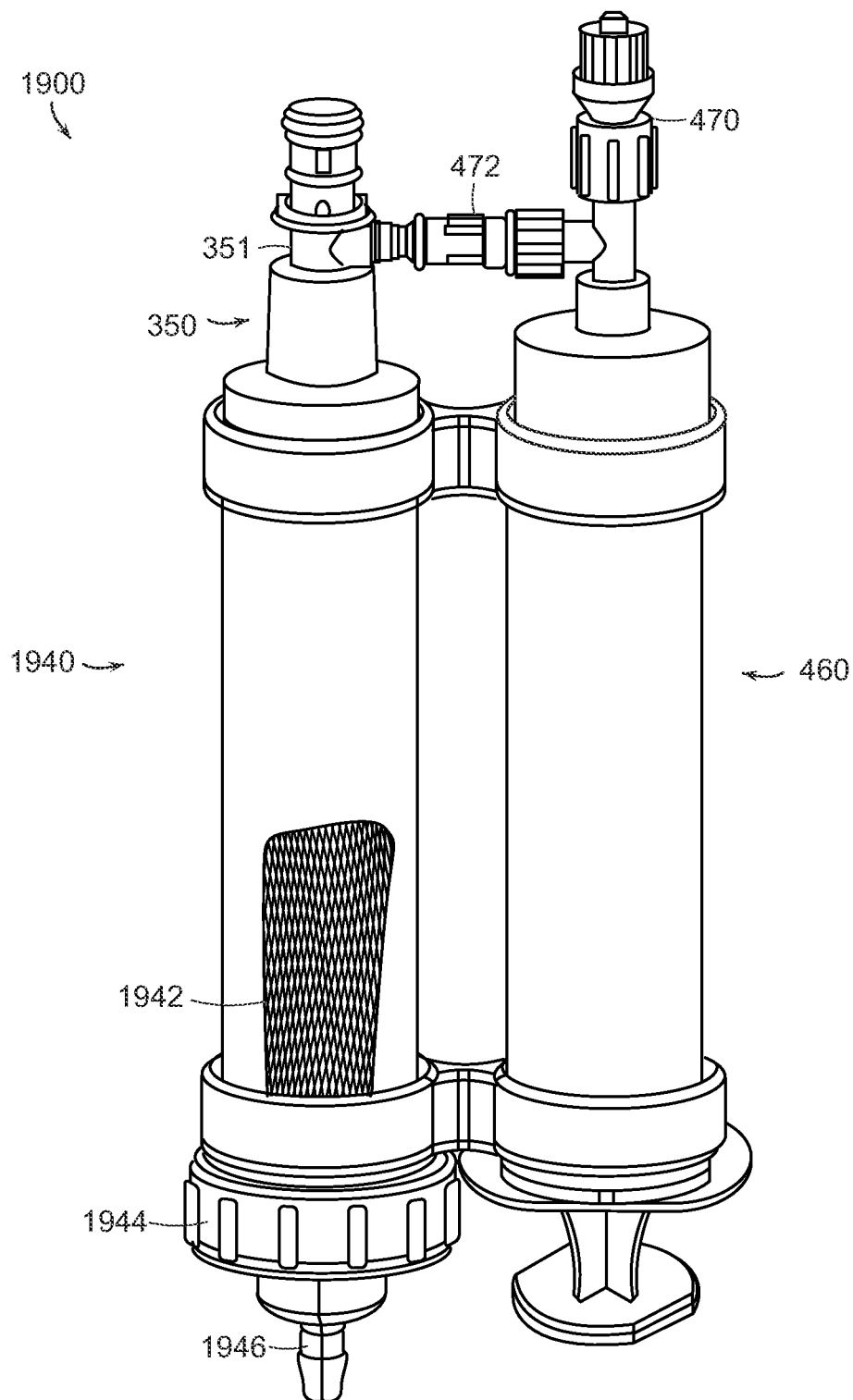
FIG. 19 is a perspective side view of a pressure source for filtering blood from aspirated clot material during a clot removal procedure configured in accordance with the present technology.

For example, FIG. 19 is a perspective side view of a pressure source 1900 for filtering blood from aspirated clot material during a clot removal procedure configured in accordance with the present technology. The pressure source 1900 is generally similar to the pressure source 400 described in detail above with reference to FIGS. 4A-4C. For example, the pressure source 1900 includes the secondary syringe 460 ("syringe 460") and the first and second one-way valves 470 and 472. However, the secondary syringe 460 is coupled to a canister 1940 rather than the primary syringe 340 (FIGS. 4A-4C). The canister 1940 includes a tip (obscured) coupled to the adaptor 350 and is configured to be removably positioned within the connector 128 of the tubing subsystem 120 (FIG. 1) to fluidly couple the canister 1940 to the tubing subsystem 120. Because the canister 1940 does not include a plunger or other component for changing a volume thereof, the syringe 460 is the only vacuum source for evacuating the canister 1940 (e.g., via repeated cycling of the secondary syringe 460).

In the illustrated embodiment, the canister 1940 further includes a filter 1942. The canister 1940 is shown as transparent in FIG. 19 for the sake of clarity. The filter 1942 is coupled to and/or covers a removable end cap 1944 having a blood separation port 1946. In operation, when blood and clot material are aspirated into the canister 1940 (e.g., via any of the methods described in detail above), the filter 1942 separates the blood from the clot material within the canister 1940. The filtered blood can be removed via the blood separation port 1946. For example, a syringe (not shown) or other device can be fluidly coupled to the blood separation port 1946 and used to draw the blood through the filter 1942 and out of the canister 1940. The filtered blood can then be reintroduced to the patient via, for example, the fluid control device 126 and/or the connector 128 of the tubing subsystem 120. Once the blood is removed from the canister 1940, the end cap 1944 can be removed from the canister 1940 (e.g., by unscrewing the end cap 1944 from the body of the canister 1940) for removing the captured clot material. In some embodiments, the filter 1942 is attached to the end cap 1944 such that removing the end cap 1944 removes the filter 1942 and permits clot material to be dumped, scooped, or otherwise removed from the canister 1940.

Figure 20C:
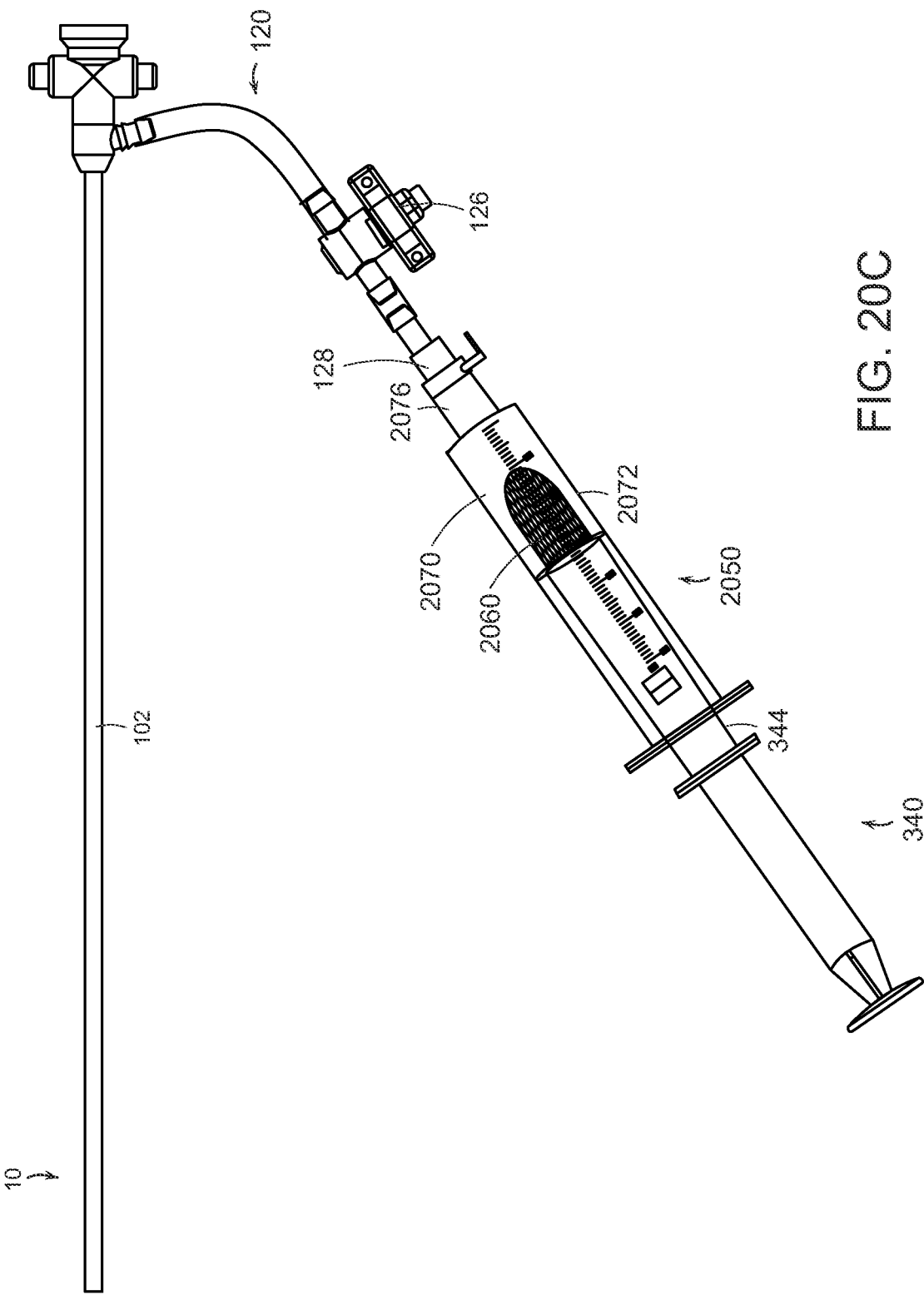
FIG. 20C is a side view of the filter device and syringe of FIG. 20B coupled to the clot removal system of FIG. 1.
Figure 20E:
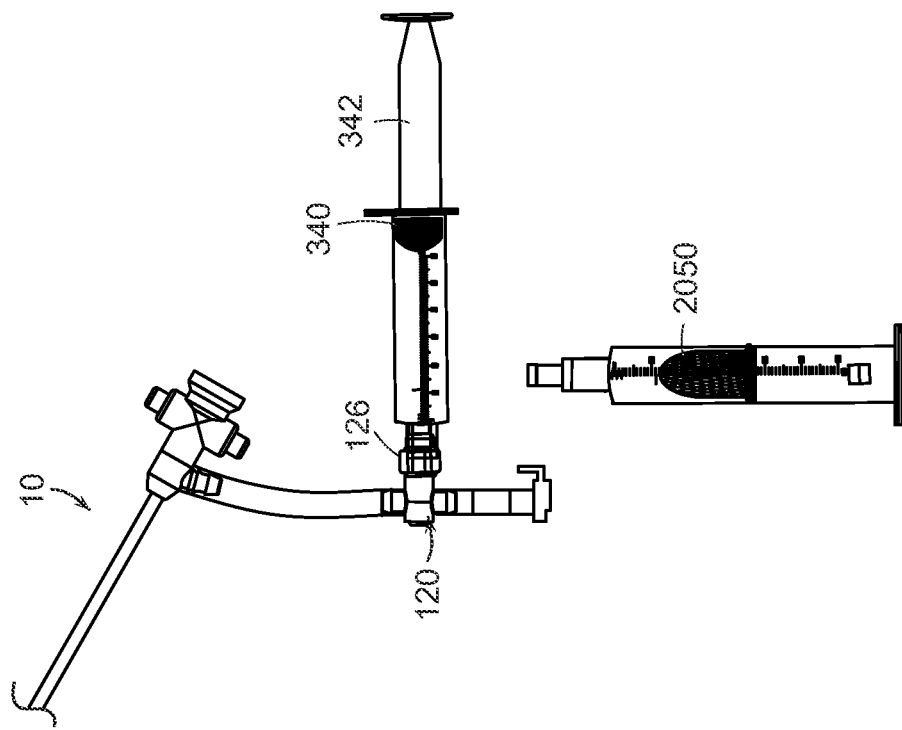
FIGS. 20D and 20E are side views of the syringe of FIG. 20A coupled to the clot removal system of FIG. 1 for reintroducing blood to a patient.

FIGS. 20A-20E illustrate a filter device 2050 for filtering blood from aspirated clot material during a clot removal procedure configured in accordance with the present technology. The filter device 2050 is configured as an in-line filter for use with, for example, one or more of the pressure sources described in detail above with reference to FIGS. 2-7. For example, FIG. 20A is a partially-exploded side view of the filter device 2050 and the pressure source 340 (FIGS. 3A-3D). In the illustrated embodiment, the filter device 2050 comprises a filter portion 2060 that is removably positionable within a barrel portion 2070. In the illustrated embodiment, the barrel portion 2070 includes a barrel 2072 that defines a chamber 2074, and a large bore tip 2076 configured to fluidly couple the chamber 2074 to external components, such as the tubing subsystem 120 (e.g., as shown in FIG. 20C). The filter portion 2060 includes a seal 2062 configured to engage (i) an interior surface of the barrel 2072 when the filter portion 2060 is positioned within the chamber 2074 of the barrel portion 2070 and (ii) an exterior surface of the syringe 340 (e.g., an exterior surface of the barrel 344) when the syringe 340 is inserted into the filter device 2050. In other embodiments, the filter portion 2060 can be permanently attached to or integrally formed with the barrel portion 2070. The filter portion 2060 further includes a filter (e.g., a mesh) 2064 configured (e.g., sized and shaped) to inhibit clot material from passing therethrough. In some embodiments, the filter 2064 can be configured to inhibit clots larger than about 100 µm (e.g., larger than about 110 µm) from passing therethrough.

FIG. 20B is a perspective side view of the syringe 340 coupled to the filter device 2050. The barrel 2072 of the barrel portion 2070 is shown as transparent in FIG. 20B (and FIGS. 20C-20E) for the sake of clarity. In the illustrated embodiment, the seal 2062 is positioned between the exterior surface of the barrel 344 of the syringe 340 and the interior surface of the barrel 2072 of the barrel portion 2070. The filter 2064 is positioned around (e.g., covers) the tip 347 of the syringe 340 to inhibit clot material from entering the barrel 344 of the syringe 340 during operation.

FIG. 20C is a side view of the filter device 2050 and syringe 340 coupled to the tubing subsystem 120 of the assembly 10. More specifically, the tip 2076 can be inserted into the connector 128 of the tubing subsystem 120 as described in detail above. When the filter device 2050 and the syringe 340 are coupled to the tubing subsystem 120, the filter device 2050 is positioned in-line (e.g., in series) with the syringe 340. In the embodiment illustrated in FIG. 20C, the plunger 342 of the syringe 340 has been withdrawn to generate negative pressure in the combined volume of the barrels 2072 and 344. As described in detail above, opening the fluid control device 126 nearly instantaneously applies the negative pressure to the catheter 102 to generate suction therein. When clot material and blood are aspirated through the catheter 102 and the tubing subsystem 120, the filter portion 2060 inhibits the clot material from entering the barrel 344 of the syringe 340. Thus, aspirated blood is collected in the barrel 344 of the syringe 340 while the aspirated clot material is collected in the barrel 2072 of the barrel portion 2070 of the filter device 2050. In this manner, clot material and blood can be separated during aspiration.

Figure 20D:
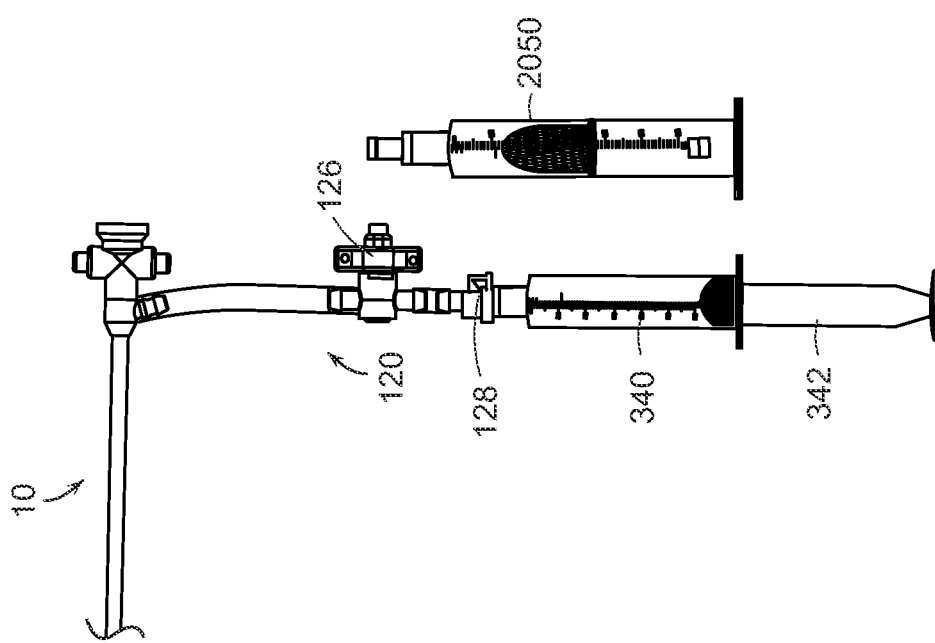

In one aspect of the present technology, separating the blood from the clot material such that the blood is within the syringe 340 permits the blood to be easily reintroduced to the patient. For example, FIGS. 20D and 20E are side views of the syringe 340 coupled to the tubing subsystem 120 of the assembly 10 for reintroducing blood to a patient. In some embodiments, as shown in FIG. 20D, the syringe 340 can be decoupled from the filter device 2050 and directly coupled to the connector 128. With the fluid control device 126 in an open position, the blood can then be reintroduced to the patient through the assembly 10 by depressing the plunger 342 of the syringe 340. In some embodiments, as shown in FIG. 20E, the syringe 340 can be decoupled from the filter device 2050 and directly coupled to a port on the fluid control device 126. With the fluid control device 126 in a closed position, the blood can then be reintroduced to the patient through the assembly 10 by depressing the plunger 342 of the syringe 340. Referring to FIG. 20A-20E together, after or before reintroducing filtered blood to the patient, the filter portion 2060 of the filter device 2050 can be removed from the barrel portion 2070 so that the collected clot material can be removed and the filter device 2050 cleaned. In some embodiments, the filter device 2050 and a coupled pressure source can be used to filter blood from clot material after—as opposed to during—an aspiration pass. For example, the filter device 2050 and coupled pressure source could be used to withdraw blood and clot material collected in the canister 1940 of the pressure source 1900 (e.g., where the canister 1940 does not include the filter 1942).

Figure 21A:
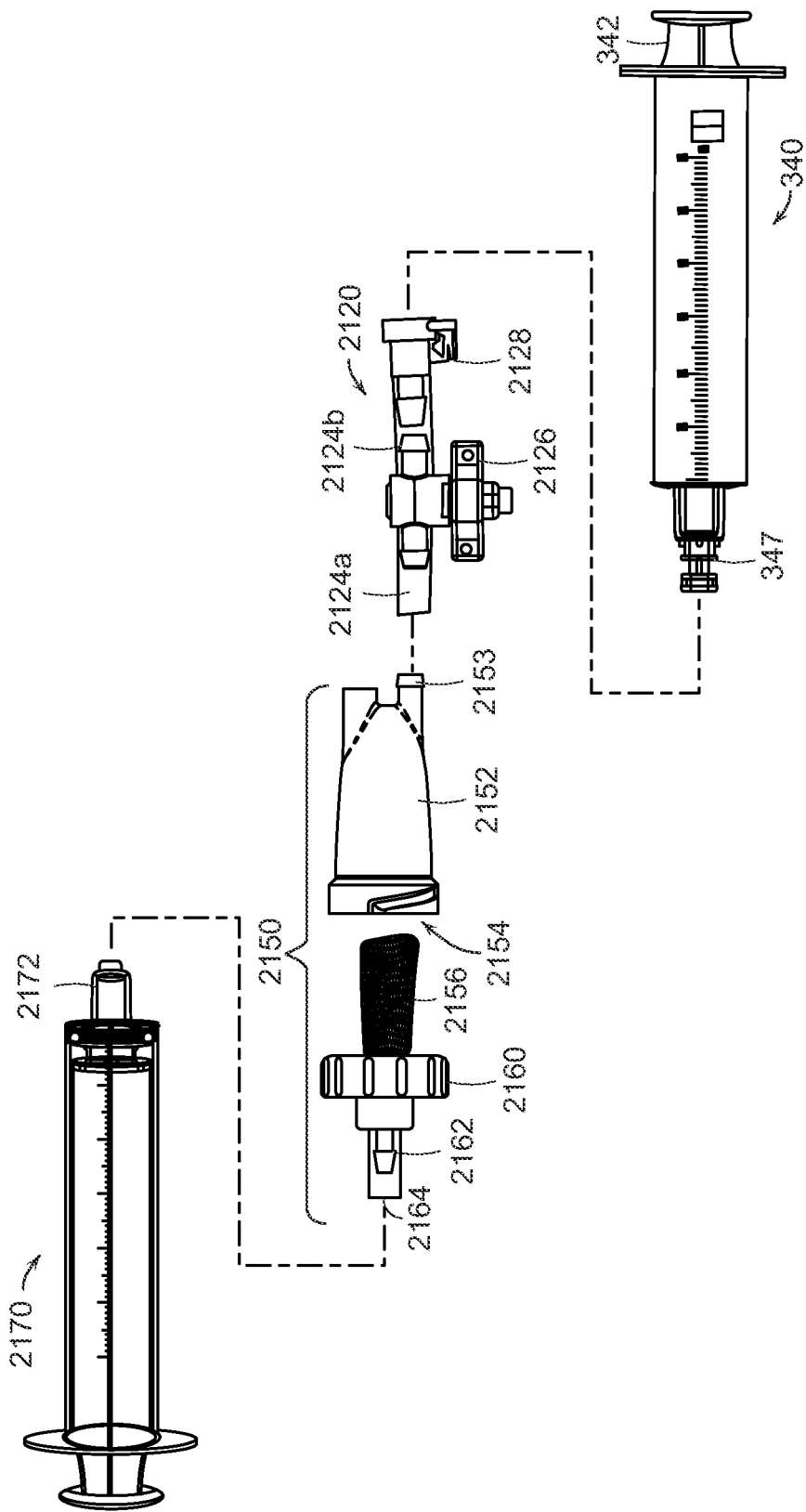
FIG. 21A is a partially-exploded side view of a filter device, a pressure source, and a reinfusion syringe configured in accordance with the present technology.
Figure 21B:
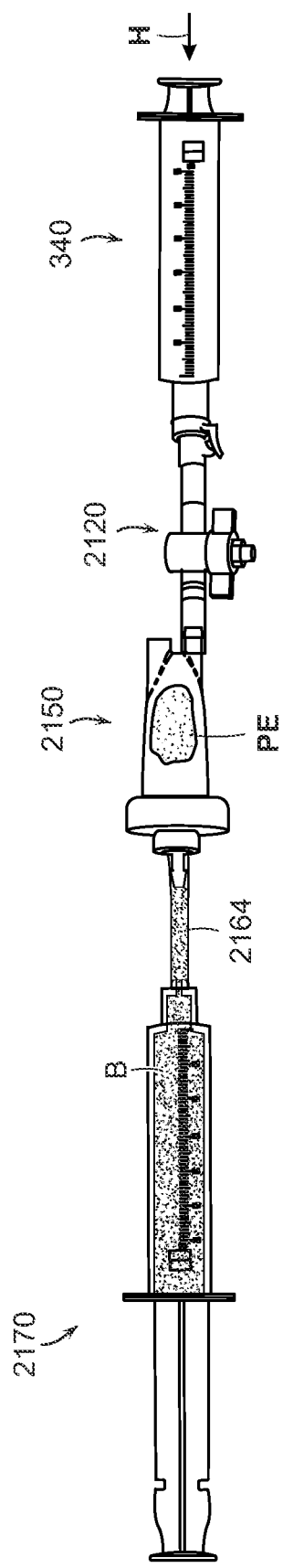
FIG. 21B is a perspective side view of the filter device of FIG. 21A coupled to the pressure source and the reinfusion syringe of FIG. 21A.

FIGS. 21A and 21B illustrate a filter device 2150 for filtering blood from aspirated clot material during a clot removal procedure configured in accordance with the present technology. The filter device 2150 is configured for use with, for example, one or more of the pressure sources described in detail above with reference to FIGS. 2-7. For example, FIG. 21A is a partially-exploded side view of the filter device 2150 and the pressure source 340 (FIGS. 3A-3D). In the illustrated embodiment, the filter device 2150 includes a housing 2152 defining a chamber 2154, a filter 2156 configured to be positioned within the housing 2152, and a cap assembly 2160 configured to be releasably coupled to the housing 2152 (e.g., via a threaded connection, snap-fit connection, etc.). In some embodiments, the filter 2156 can have a porosity of between about 50-200 microns.

The housing 2152 can include a port 2153 configured to be removably, fluidly coupled to the pressure source 340 via a tubing subsystem 2120. In the illustrated embodiment, the tubing subsystem 2120 includes tubing sections 2124 (individually labeled as a first tubing section 2124a and a second tubing section 2124b), a fluid control device 2126 (e.g., a valve, stop cock, clamp, etc.), and a connector 2128 (e.g., a large bore connector) for fluidly coupling the tubing subsystem 2120 to the pressure source 340. In the illustrated embodiment, the cap assembly 2160 includes a fluid connector 2162 (e.g., a standard Luer or large bore connector) configured to be connected to a receiving/reinfusion syringe 2170 via, for example, a tubing section 2164. In some embodiments, the cap assembly 2160 can include a valve (e.g., a one-way valve, a check valve, etc.) that provides for one-way fluid flow through filter assembly 2150.

In operation, during a clot removal procedure, the pressure source 340 can be decoupled from the connector 128 (FIG. 1) after an aspiration pass and when the pressure source 340 is full of blood and clot material. After connecting the filter device 2150 to the receiving syringe 2170, the pressure source 340 can be coupled to the filter device 2150. For example, FIG. 21B is a perspective side view of the filter device 2150 coupled to (i) the pressure source 340 via the tubing subsystem 2120 and (ii) the reinfusion syringe 2170 via the tubing section 2164. More specifically, referring to FIGS. 21A and 21B together, the tip 347 of the pressure source 340 can be coupled to the connector 2128 of the tubing subsystem 2120, and a tip 2172 of the reinfusion syringe 2170 can be coupled to the tubing section 2164. In other embodiments, the filter device 2150 can be coupled to the pressure source 340 and/or the reinfusion syringe 2170 in other manners (e.g., directly such that the all or part of the tubing subsystem 120 is omitted). Alternatively, the filter device 2150 can be directly attached to the side port 108 (FIG. 1), an IV line (not shown), or another suitable connection point for reintroducing blood to the patient, After coupling the pressure source 340 to the filter device 2150, the fluid control device 2128 can be opened to fluidly connect the pressure source 340 to the filter device 2150. Then, the operator can depress the plunger 342 of the pressure source 340 to drive the blood and clot material from the pressure source 340 into and/or through the filter device 2150. The filter 2156 of the filter device 2150 filters the blood from the clot material such that the blood flows into the reinfusion syringe 2170 and the clot material remains in the chamber 2154 of the filter device 2150. For example, as shown in FIG. 21B, blood B fills the reinfusion syringe 2170 and clot material PE remains within the chamber 2154 of the filter device 2150 after depressing the plunger 342 of the pressure source 340 in the direction indicated by the arrow H.

Next, the reinfusion syringe 2170 can be decoupled from the filter device 2150 so that the blood B can be reintroduced to the patient. For example, the reinfusion syringe 2170 could be directly coupled to a port on the fluid control device 126 (FIG. 1). The cap assembly 2160 can be decoupled from the housing 2152 of the filter device 2150 to, for example, permit an operator to remove the clot material PE collected in the housing 2152 and thereby clean and prepare the filter device 2150 for another use.

Figure 22:
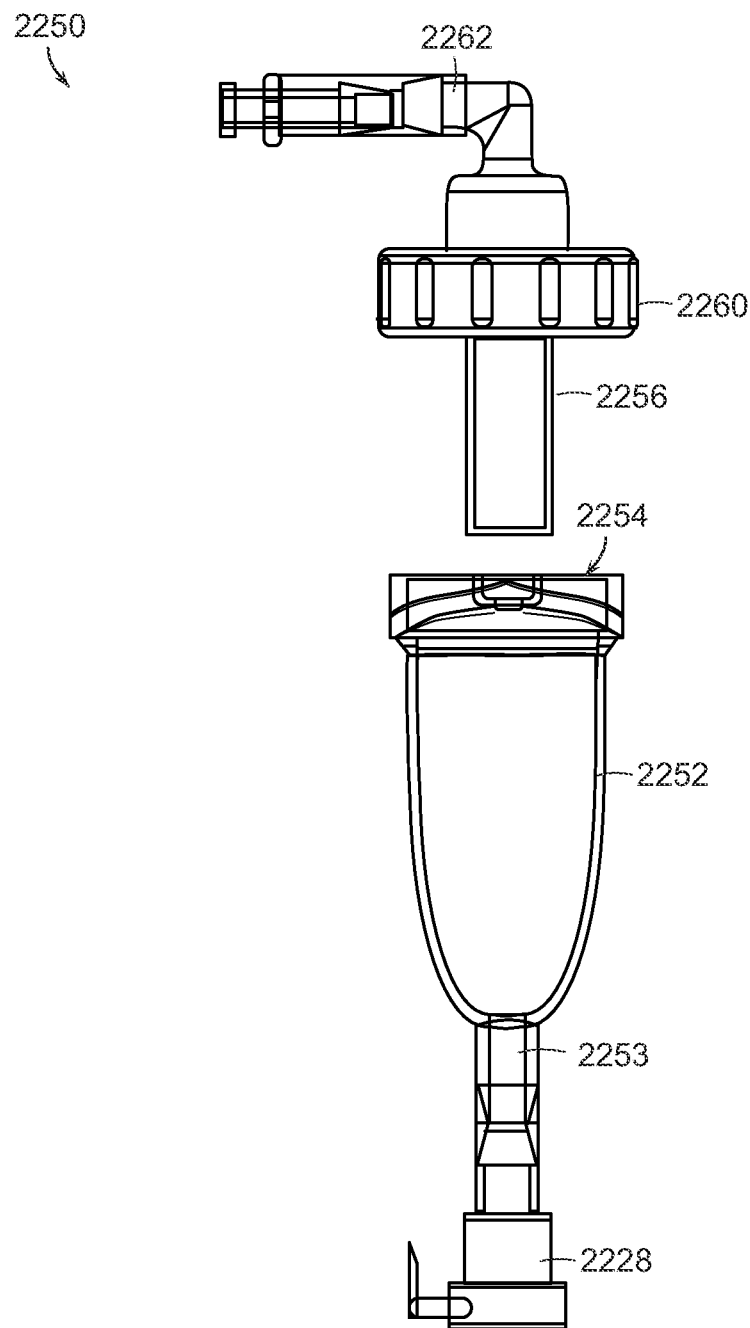
FIG. 22 is a partially-exploded side view of a filter device configured in accordance with the present technology.

FIG. 22 is a partially-exploded side view of a filter device 2250 for filtering blood from aspirated clot material during a clot removal procedure configured in accordance with the present technology. The filter device 2250 is configured for use with, for example, one or more of the pressure sources described in detail above with reference to FIGS. 2-7. In general, the filter device 2250 is generally similar to the filter device 2150 described in detail with reference to FIGS. 21A and 21B. For example, the filter device 2250 includes a housing 2252 defining a chamber 2254, a filter 2256 configured to be positioned within the housing 2252, and a cap assembly 2260 configured to be releasably coupled to the housing 2252. However, in the illustrated embodiment the filter device 2250 includes a port 2253 that is directly connected to a connector 2228 configured to be coupled to a pressure source (e.g., the pressure source 340 shown in FIGS. 3A-3D). The cap assembly 2260 includes a fluid connector 2162 (e.g., a standard Luer or large bore connector) configured to be connected to a reinfusion syringe, a sheath, an IV line, etc., (not shown). In some embodiments, the fluid connector 2262 is angled relative to the filter 2260 and/or the housing 2252. For example, the fluid connector 2262 is formed to have an approximately right angle in FIG. 22. In one aspect of the present technology, this arrangement makes the filter device more ergonomic during use.

Figure 23:
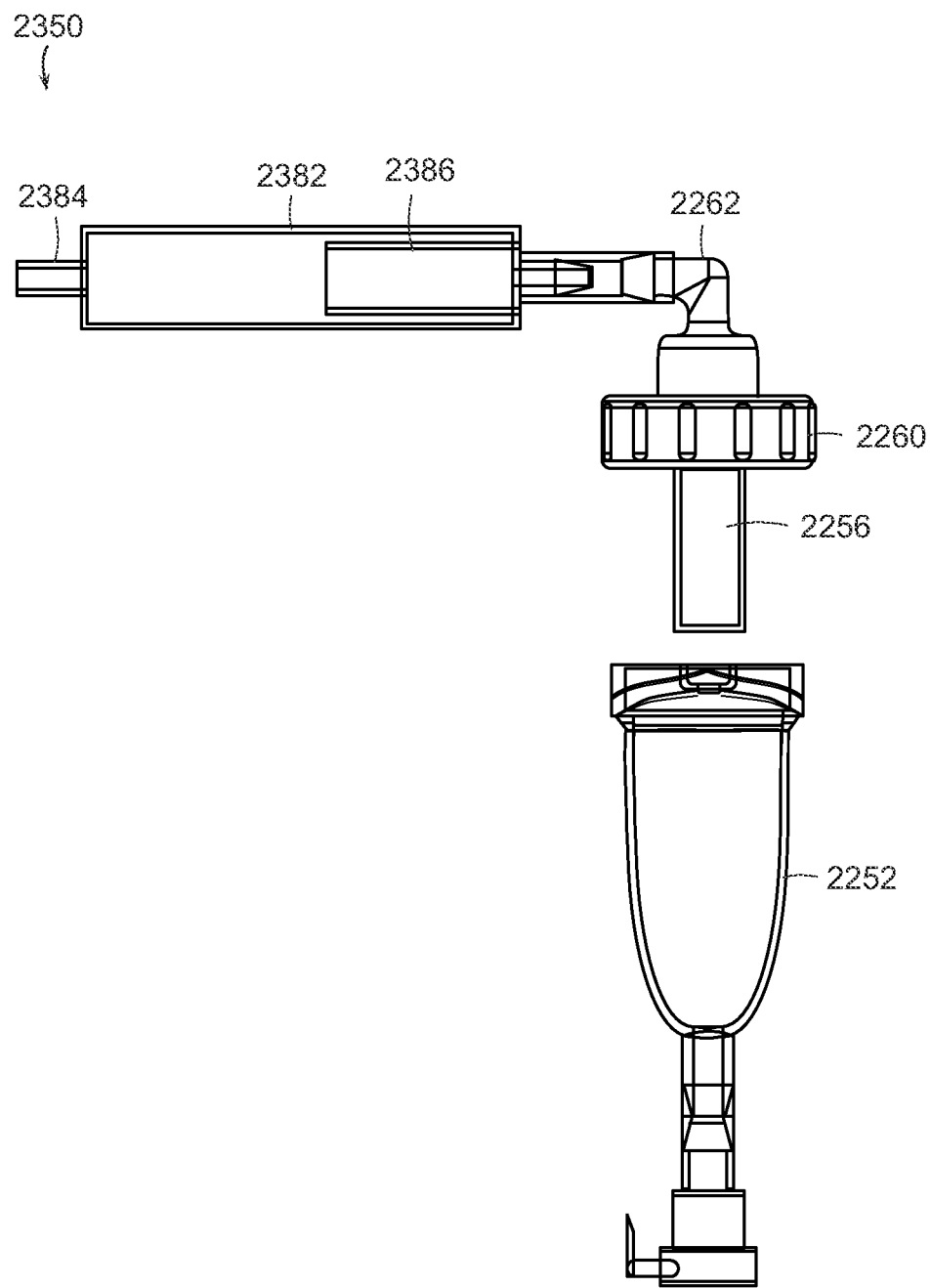
FIG. 23 is a partially-exploded side view of a filter device configured in accordance with the present technology.

FIG. 23 is a partially-exploded side view of a filter device 2350 for filtering blood from aspirated clot material during a clot removal procedure configured in accordance with the present technology. The filter device 2350 is configured for use with, for example, one or more of the pressure sources described in detail above with reference to FIGS. 2-7. The filter device 2350 is generally identical to the filter device 2250 described in detail with reference to FIG. 22—including, for example, the housing 2252 ("a first housing 2252"), the filter 2256 ("a first filter 2256"), and the cap assembly 2260 including the fluid connector 2262 ("a first fluid connector 2262"). However, in the illustrated embodiment a second housing 2382 and a second filter 2386 are fluidly connected to the fluid connector 2262. The second housing 2382 includes a second fluid connector 2384 that can be fluidly connected to a reinfusion syringe, a sheath, an IV line, etc., (not shown). The second filter 2386 is configured to provide a second stage of filtration. For example, in some embodiments the first filter 2256 has a larger porosity than the second filter 2386. For example, the first filter 2256 can have a porosity of between about 50-200 microns and the second filter 2386 can have a porosity of between about 50-170 microns.

In general, one skilled in the art will understand that the various embodiments of filter devices disclosed herein may have different components or combinations of components. For example, the filter devices 2050, 2150, 2250, and/or 2350 ("the filter devices") could be utilized with any of several different pressure sources other than the syringe 340 (e.g., those shown in FIGS. 2 and 4-7). In some embodiments, the filter devices can be formed as a component of the tubing subsystem 120 (FIG. 1). Moreover, the filter devices can include any number of filters and/or housings to provide any number of filtration stages.

VII. Examples

Several aspects of the present technology are set forth in the following examples:
[[TO ADD ONCE CLAIMS ARE FINALIZED]]

CONCLUSION

The above detailed descriptions of embodiments of the technology are not intended to be exhaustive or to limit the technology to the precise form disclosed above. Although specific embodiments of, and examples for, the technology are described above for illustrative purposes, various equivalent modifications are possible within the scope of the technology as those skilled in the relevant art will recognize. For example, although steps are presented in a given order, alternative embodiments may perform steps in a different order. The various embodiments described herein may also be combined to provide further embodiments.

From the foregoing, it will be appreciated that specific embodiments of the technology have been described herein for purposes of illustration, but well-known structures and functions have not been shown or described in detail to avoid unnecessarily obscuring the description of the embodiments of the technology. Where the context permits, singular or plural terms may also include the plural or singular term, respectively.

Moreover, unless the word "or" is expressly limited to mean only a single item exclusive from the other items in reference to a list of two or more items, then the use of "or" in such a list is to be interpreted as including (a) any single item in the list, (b) all of the items in the list, or (c) any combination of the items in the list. Additionally, the term "comprising" is used throughout to mean including at least the recited feature(s) such that any greater number of the same feature and/or additional types of other features are not precluded. It will also be appreciated that specific embodiments have been described herein for purposes of illustration, but that various modifications may be made without deviating from the technology. Further, while advantages associated with some embodiments of the technology have been described in the context of those embodiments, other embodiments may also exhibit such advantages, and not all embodiments need necessarily exhibit such advantages to fall within the scope of the technology. Accordingly, the disclosure and associated technology can encompass other embodiments not expressly shown or described herein.

We claim:

1. An aspiration system with accelerated response, comprising:
  an aspiration pump in communication with a first chamber, wherein the first chamber comprises a first barrel of a first syringe, and wherein the aspiration pump comprises a plunger of the first syringe slidably received in the first barrel;
  an aspiration catheter configured for placement into fluid communication with the first chamber by way of an aspiration tube;
  a second chamber in between the aspiration pump and the aspiration catheter, wherein the second chamber comprises a second barrel of a second syringe; and
  a valve between the second chamber and the aspiration catheter, wherein the valve is configured to be closed while negative pressure is generated in the first and second chambers, and wherein the valve is configured to be opened after the negative pressure is generated in the first and second chambers; and
  wherein upon actuation to open the valve and the negative pressure having been generated in the first and second chambers, fluid is rapidly aspirated from the aspiration catheter into the second chamber.

2. The aspiration system of claim 1 wherein:
  the valve comprises a user-actuatable stopcock valve; and
  the aspiration tube comprises a first tubing section coupled to the second chamber and one side of the stopcock valve and a second tubing section coupled to the other side of the stopcock valve.

3. The aspiration system of claim 1 wherein:
  the valve comprises a user-actuatable stopcock valve; and
  the aspiration tube comprises a first tubing section coupled to the second chamber and one side of the stopcock valve and a second tubing section coupled to the other side of the stopcock valve; and
  the second syringe further comprises a second plunger slidably received in the second barrel.

4. The aspiration system of claim 1, further comprising a one-way valve separate from the valve between the first chamber and the second chamber configured to block flow from the first chamber to the second chamber and allow flow from the second to the first chamber.

5. The aspiration system of claim 1, wherein the first syringe comprises a secondary pressure source and the second syringe comprises a primary pressure source.

6. The aspiration system of claim 5 wherein the first plunger is rotationally received in the first barrel and the second plunger is rotatably received in the second barrel.

7. The aspiration system of claim 1 wherein a negative pressure in the first chamber causes fluid flow from the second chamber to the first chamber when the valve is opened.

8. The aspiration system of claim 1 wherein the first chamber and the second chamber are configured such that both the first chamber and the second chamber can both be at a negative pressure at the same time, and wherein upon opening the valve the negative pressure in the first chamber contributes to a rapid pressure drop in the aspiration catheter.

9. The aspiration system of claim 1, further comprising a filter in the second chamber.

10. The aspiration system of claim 9 wherein the filter includes a plurality of pores sized to inhibit clot material from flowing therethrough and to permit blood to flow therethrough.

11. The aspiration system of claim 1 wherein the first chamber is fluidically coupled in serial to the second chamber.

12. An aspiration system with accelerated response, comprising:
  an aspiration pump in communication with a first chamber, wherein the first chamber comprises a first barrel of a syringe, and wherein the pump comprises a plunger of the first syringe slidably received in the first barrel;
  an aspiration catheter configured for placement into fluid communication with the first chamber by way of an aspiration tube;

a second chamber in between the aspiration pump and the aspiration catheter, wherein the second chamber comprises a second barrel; and a valve between the second chamber and the aspiration catheter, wherein the valve is configured to be closed while negative pressure is generated in the first and second chambers, and wherein the valve is configured to be opened after the negative pressure is generated in the first and second chambers;

wherein upon actuation to open the valve and the negative pressure having been generated in the first and second chambers, fluid is rapidly aspirated from the aspiration catheter into the second chamber.

13. The aspiration system of claim 12 wherein the second chamber is configured to sealingly receive the first barrel.

14. The aspiration system of claim 12, further comprising a filter in the second barrel.

15. The aspiration system of claim 12, further comprising a filter in the second chamber, wherein the filter includes a plurality of pores sized to inhibit clot material from flowing therethrough and to permit blood to flow therethrough.

16. The aspiration system of claim 12 wherein the first chamber is fluidically coupled in serial to the second chamber.

17. An aspiration system with accelerated response, comprising:

an aspiration pump in communication with a first chamber, wherein the first chamber comprises a first barrel of a syringe, and wherein the pump comprises a plunger of the first syringe slidably received in the first barrel;

an aspiration catheter configured for placement into fluid communication with the first chamber by way of an aspiration tube;

a second chamber in between the aspiration pump and the aspiration catheter, wherein the second chamber comprises a second barrel, wherein the second chamber is configured to sealingly receive the first barrel; and a valve between the second chamber and the aspiration catheter, wherein the valve is configured to be closed while negative pressure is generated in the first and second chambers, and wherein the valve is configured to be opened after the negative pressure is generated in the first and second chambers;

wherein upon actuation to open the valve and the negative pressure having been generated in the first and second chambers, fluid is rapidly aspirated from the aspiration catheter into the second chamber.

18. The aspiration system of claim 17, further comprising a filter in the second barrel.

* * * * *